(12) United States Patent
Wang et al.

(10) Patent No.: US 11,261,206 B2
(45) Date of Patent: Mar. 1, 2022

(54) OLEFIN METATHESIS CATALYSTS

(71) Applicant: Umicore AG & Co. KG, Hanau-Wolfgang (DE)

(72) Inventors: Li-sheng Wang, Azusa, CA (US); Mark S. Trimmer, Monrovia, CA (US)

(73) Assignee: Umicore AG & Co. KG

( * ) Notice: Subject to any disclaimer, the term of this patent is extended or adjusted under 35 U.S.C. 154(b) by 358 days.

(21) Appl. No.: 16/325,915

(22) PCT Filed: Aug. 17, 2017

(86) PCT No.: PCT/US2017/047339
§ 371 (c)(1),
(2) Date: Feb. 15, 2019

(87) PCT Pub. No.: WO2018/035319
PCT Pub. Date: Feb. 22, 2018

(65) Prior Publication Data
US 2021/0155648 A1    May 27, 2021

Related U.S. Application Data

(60) Provisional application No. 62/377,432, filed on Aug. 19, 2016.

(51) Int. Cl.
*C07F 15/00* (2006.01)
*B01J 31/28* (2006.01)
(Continued)

(52) U.S. Cl.
CPC ....... *C07F 15/0046* (2013.01); *B01J 31/2269* (2013.01); *B01J 31/28* (2013.01);
(Continued)

(58) Field of Classification Search
CPC .............. C07F 15/0046; B01J 31/2269; B01J 31/2273; B01J 31/2278; B01J 2231/54; B01J 2231/543; C08F 4/80
See application file for complete search history.

(56) References Cited

U.S. PATENT DOCUMENTS 4,899,005 A    2/1990  Lane et al.
5,728,785 A    3/1998  Grubbs et al.
(Continued)

FOREIGN PATENT DOCUMENTS

WO    WO-2012174502 A2    12/2012

OTHER PUBLICATIONS

Weskamp, T.; Schattenmann, W.C.; Spiegler, M.; Herrmann, W.A. Angewandte Chemie, International Edition, 1998, 37, 2490-2493. (Year: 1998).*

(Continued)

*Primary Examiner* — Rip A Lee
(74) *Attorney, Agent, or Firm* — Faegre Drinker Biddle & Reath LLP

(57) ABSTRACT

This invention relates generally to olefin metathesis catalyst compounds, to the preparation of such compounds, compositions comprising such compounds, methods of using such compounds, articles of manufacture comprising such compounds, and the use of such compounds in the metathesis of olefins and olefin compounds. The invention has utility in the fields of catalysts, organic synthesis, polymer chemistry, and industrial and fine chemicals industry.

8 Claims, 2 Drawing Sheets

(51) Int. Cl.
*B01J 31/22* (2006.01)
*C08F 4/80* (2006.01)

(52) U.S. Cl.
CPC ........ *B01J 31/2273* (2013.01); *B01J 31/2278* (2013.01); *B01J 2231/543* (2013.01); *B01J 2531/821* (2013.01); *C08F 4/80* (2013.01)

(56) References Cited

U.S. PATENT DOCUMENTS

| | | | |
|---|---|---|---|
| 6,635,768 B1 * | 10/2003 | Herrmann | B01J 31/2265 548/101 |
| 8,067,610 B2 | 11/2011 | Schrodi | |
| 8,501,973 B2 | 8/2013 | Schrodi et al. | |
| 9,776,178 B2 * | 10/2017 | Mauduit | B01J 31/2273 |
| 9,920,086 B2 * | 3/2018 | Stephan | C08F 4/00 |
| 10,159,966 B2 * | 12/2018 | Verpoort | B01J 31/2273 |
| 2006/0160974 A1 | 7/2006 | Schulte et al. | |
| 2009/0221750 A1 | 9/2009 | Tsunogae et al. | |
| 2017/0137448 A1 * | 5/2017 | Pranckevicius | C07F 15/0046 |

OTHER PUBLICATIONS

Bantreil, X.; Randall, R.A.M.; Slawin, A.M.Z.; Nolan, S.P. Organometallics 2010, 29, 3007-3011. (Year: 2010).*

Vorfalt, T.; Leuthausser, S.; Plenio, H. Angewandte Chemie Int. Ed. 2009, 48, 5191-5194. (Year: 2009).*

Love, J., et al., "Synthesis, Structure, and Activity of Enhanced Inititators for Olefin Metathesis", J. Am. Chem. Soc., 2003, vol. 125, pp. 10103-10109.

Trnka, T., et al., Synthesis and Activity of Ruthenium Alkylidene Complexes Coordinated with Phosphine and N-Heterocyclic Carbene Ligands, J. Am. Chem. Soc., 2003, vol. 125, pp. 2546-2558.

Vinh Huynh, H., et al., "Highly modular access to functionalised metal-carbenes via post-modifications of a single bromoalkyl-substituted NHC—Pd(II) complex", Chem Commun., 2013, vol. 49, pp. 4244-4246.

Volland, M., et al., "An 'Old Hydride' in a new synthesis: a convenient approach to Grubbs-type carbene complexes $(PPh_3)_2Cl_2Ru=CH—CH=CR_2$ and their hexacoordinate acetonitrile adducts", Journal of Organometallic Chemistry, 2002, vol. 641, pp. 220-226.

Weskamp, T., et al., "A Novel Class of Ruthenium Catalysts for Olefin Metathesis", Angew. Chem. Int. Ed., 1998, vol. 37, No. 18, pp. 2490-2493.

International Preliminary Report on Patentability for PCT/US2017/047339 dated Nov. 6, 2017.

Trnka, T., et al., "The Development of $L_2X_2Ru=CHR$ Olefin Metathesis Catalysts: An Organometallic Success Story", Accounts of Chemical Research, vol. 34, No. 1, (2001), pp. 18-29.

* cited by examiner

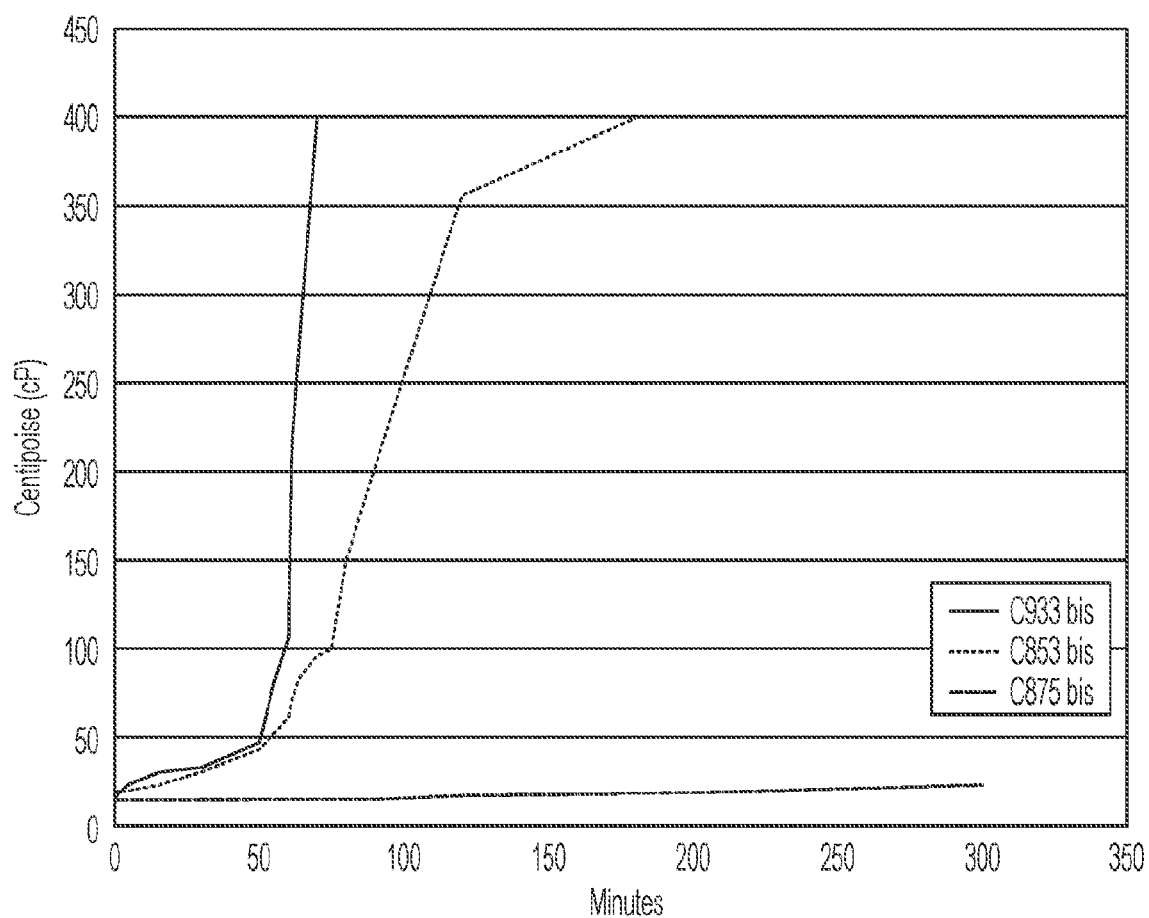

OLEFIN METATHESIS CATALYSTS

CROSS-REFERENCE TO RELATED APPLICATIONS

This application is a national stage application (under 35 U.S.C. § 371) of PCT/US2017/047339, filed Aug. 17, 2017, which claims benefit of U.S. Application No. 62/377,432, filed Aug. 19, 2016, both of which are incorporated herein by reference in their entirety.

TECHNICAL FIELD

This invention relates generally to olefin metathesis catalyst compounds, to the preparation of such compounds, compositions comprising such compounds, methods of using such compounds, articles of manufacture comprising such compounds, and the use of such compounds in the metathesis of olefins and olefin compounds. The invention has utility in the fields of catalysts, organic synthesis, polymer chemistry, and industrial and fine chemicals industry.

BACKGROUND

The technology of ruthenium metathesis catalysts has enabled the development of several research platforms including CM (cross metathesis), RCM (ring closing metathesis), ROMP (ring opening metathesis polymerization). The incorporation of NHC (N-Heterocyclic Carbene) ligands has played an essential role in the development of Ruthenium metathesis catalysts. In the past most of the attention was focused on the efficacy of ruthenium catalysts with low catalyst loading and fast/steady substrate conversion.

However, there is a need of latent olefin metathesis catalysts, which when mixed with monomers would not polymerize instantaneously, allowing for longer handling of the catalyst-monomer mixtures or even storage of the formulation for longer periods. Furthermore, commercially available catalysts suffer from considerable degradation during metathesis reactions. Latent catalysts, which generally exhibit higher thermal stabilities, could yield a catalyst with longer shelf life.

Herrmann et al. first reported Ruthenium metathesis catalysts with two NHC ligands, also referred to as bis-NHC catalysts (Weskamp, T.; Schattenmann, W. C.; Spiegler, M.; Herrmann, W. A. *Angew. Chem., Int. Ed.* 1998, 37, 2490).

During RCM reactions, these metathesis catalysts showed slow initiation at 40° C., compared to 1$^{st}$ generation Grubbs' catalysts. Grubbs et al. reported bis-NHC catalysts with aryl substituents on the nitrogen atoms of the imidazolinylidene or the imidazolylidene rings (Trnka, T. M.; Morgan, J. P.; Sanford, M. S.; Wilhelm, T. E.; Scholl, M.; Choi, T. L.; Ding, S. D.; Day, M. W.; Grubbs, R. H. *J. Am. Chem. Soc.* 2003, 125, 2546). It was noticed that these bis-NHC compounds require high thermal energy initiation, compared to the 1$^{st}$ and 2$^{nd}$ generation Grubbs' catalysts. However, there is still a need for latent catalyst metathesis catalysts and synthetic routes to make them.

SUMMARY OF THE INVENTION

To meet this need the inventors have discovered various olefin metathesis catalysts as described herein in the invention.

In one embodiment, the invention provides an olefin metathesis catalyst represented by the structure of Formula (I):

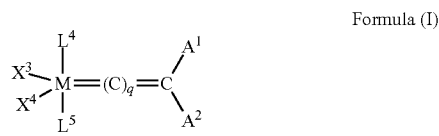

Formula (I)

wherein:
M is a Group 8 transition metal;
$L^4$ and $L^5$ are independently N-heterocyclic carbene (NHC) ligands;
q is 0 or 1;
$X^3$ and $X^4$ are independently anionic ligands; and
$A^1$ and $A^2$ are independently selected from hydrogen, hydrocarbyl, substituted hydrocarbyl, heteroatom-containing hydrocarbyl, substituted heteroatom-containing hydrocarbyl, and functional groups.

In one aspect, the invention provides a method of synthesizing the olefin metathesis catalysts of the invention.

In one aspect, the invention provides the use of the olefin metathesis catalysts of the invention in CM (cross metathesis) reactions, RCM (ring closing metathesis) reactions, ROMP (ring opening metathesis polymerization) reactions, ADMET (acyclic diene metathesis polymerization).

In another aspect, the invention provides ROMP compositions comprising at least one cyclic olefin, combined with at least one olefin metathesis catalyst of the invention. ROMP compositions of the invention may be optionally formulated with additives.

In one embodiment, the invention provides a method of making a ROMP composition comprising combining at least one cyclic olefin, as described herein, with at least one cyclic olefin metathesis catalyst of the invention. Further, the invention provides articles made with ROMP compositions of the invention.

These and other aspects of the present invention will be apparent to the skilled artisan in light of the following detailed description and examples. Furthermore, it is to be understood that none of the embodiments or examples of the invention described herein are to be interpreted as being limiting.

BRIEF DESCRIPTION OF THE DRAWING

FIG. 2 shows the Viscosity Profile of DCPD with 30% Trimer at 50° C. in latent catalyst systems.

DETAILED DESCRIPTION

Figure 1:
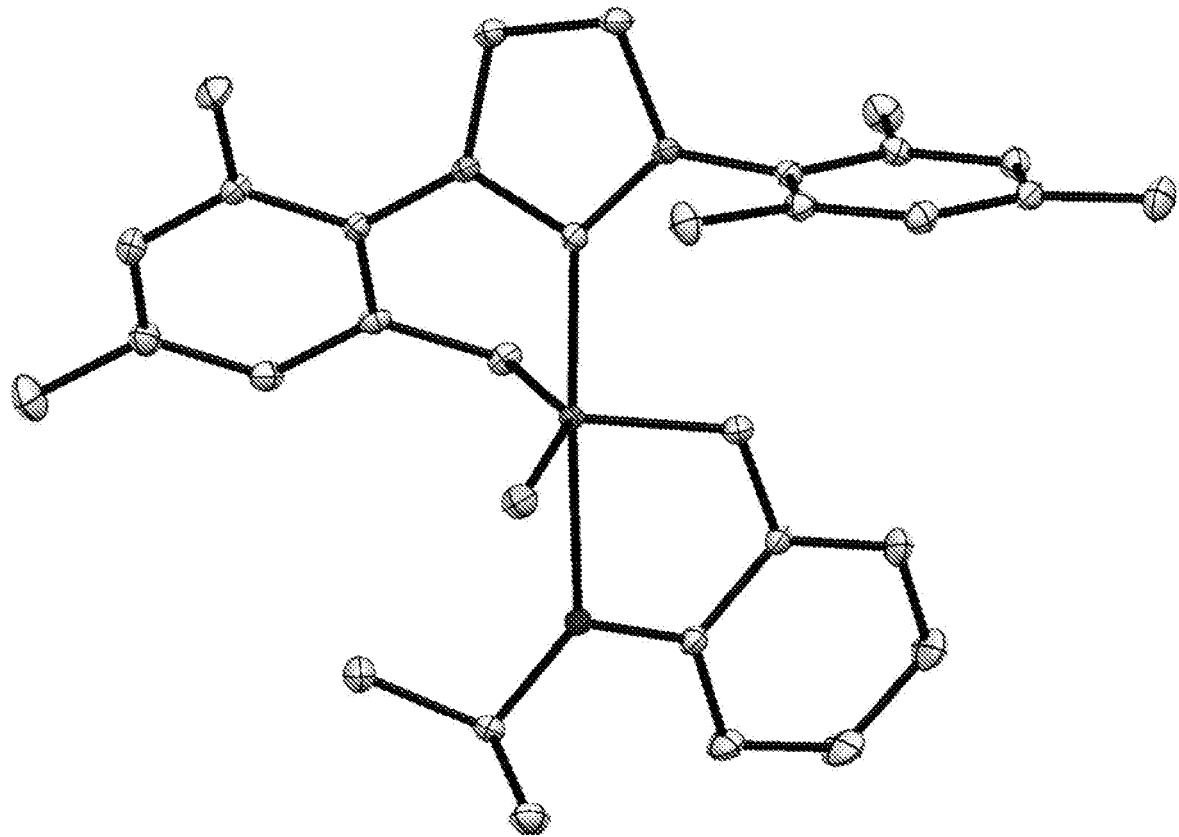
FIG. 1 shows the X-Ray Crystal structure of catalyst C590.

Unless otherwise indicated, the invention is not limited to specific reactants, substituents, catalysts, cyclic olefin catalysts, catalyst compositions, cyclic olefins, cyclic olefin compositions, ROMP compositions, reaction conditions, or the like, as such may vary. It is also to be understood that the terminology used herein is for the purpose of describing particular embodiments only and is not to be interpreted as being limiting.

As used in the specification and the appended claims, the singular forms "a," "an," and "the" include plural referents unless the context clearly dictates otherwise. Thus, for example, reference to "an α-olefin" includes a single α-olefin as well as a combination or mixture of two or more α-olefins, reference to "a substituent" encompasses a single substituent as well as two or more substituents, and the like.

As used in the specification and the appended claims, the terms "for example," "for instance," "such as," or "including" are meant to introduce examples that further clarify more general subject matter. Unless otherwise specified, these examples are provided only as an aid for understanding the invention, and are not meant to be limiting in any fashion.

In this specification and in the claims that follow, reference will be made to a number of terms, which shall be defined to have the following meanings:

The term "alkyl" as used herein refers to a linear, branched, or cyclic, saturated hydrocarbon group generally, containing 1 to 30 carbon atoms, or 1 to 24 carbon atoms, or typically, 1 to 12 carbon atoms. Examples of suitable alkyl groups include, but are not limited to, methyl (Me), ethyl (Et), n-propyl (Pr or n-Pr), isopropyl (i-Pr), n-butyl (Bu or n-Bu), isobutyl (i-Bu), t-butyl (t-Bu), octyl (Oct), decyl, and the like, as well as cycloalkyl groups such as cyclopentyl (Cp), cyclohexyl (Cy) and the like. The term "lower alkyl" refers to an alkyl group of 1 to 6 carbon atoms, and the specific term "cycloalkyl" refers to a cyclic alkyl group, having 4 to 8, or 5 to 7, carbon atoms. The term "substituted alkyl" refers to alkyl substituted with one or more substituent groups, as defined herein, and the terms "heteroatom-containing alkyl" and "heteroalkyl" refer to alkyl in which at least one carbon atom is replaced with a heteroatom. If not otherwise indicated, the terms "alkyl" and "lower alkyl" include linear, branched, cyclic, unsubstituted, substituted, and/or heteroatom-containing alkyl and lower alkyl, respectively.

The term "alkylene" as used herein refers to a difunctional linear, branched, or cyclic alkyl group, where "alkyl" is as defined above.

The term "alkenyl" as used herein refers to a linear, branched, or cyclic hydrocarbon group of 2 to 30 carbon atoms, containing at least one double bond. Examples of suitable alkenyl groups include, but are not limited to, ethenyl, n-propenyl, iso-propenyl, n-butenyl, iso-butenyl, octenyl, decenyl, tetradecenyl, hexadecenyl, eicosenyl, tetracosenyl, and the like. Generally alkenyl groups herein contain 2 to 12 carbon atoms. The term "lower alkenyl" refers to an alkenyl group of 2 to 6 carbon atoms, and the specific term "cycloalkenyl" refers to a cyclic alkenyl group, generally having 5 to 8 carbon atoms. The term "substituted alkenyl" refers to alkenyl substituted with one or more substituent groups, as defined herein, and the terms "heteroatom-containing alkenyl" and "heteroalkenyl" refer to alkenyl in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkenylene" as used herein refers to a difunctional linear, branched, or cyclic alkenyl group, where "alkenyl" is as defined above.

The term "alkynyl" as used herein refers to a linear or branched hydrocarbon group of 2 to 24 carbon atoms containing at least one triple bond, such as ethynyl, n-propynyl, and the like. Typically, alkynyl groups herein contain 2 to 12 carbon atoms. The term "lower alkynyl" refers to an alkynyl group of 2 to 6 carbon atoms. The term "substituted alkynyl" refers to alkynyl substituted with one or more substituent groups, as defined herein, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The term "alkoxy" as used herein refers to an alkyl group bound through a single, terminal ether linkage; that is, an "alkoxy" group may be represented as —O-alkyl where alkyl is as defined above. A "lower alkoxy" group refers to an alkoxy group containing 1 to 6 carbon atoms. Analogously, "alkenyloxy" and "lower alkenyloxy" respectively refer to an alkenyl and lower alkenyl group bound through a single, terminal ether linkage, and "alkynyloxy" and "lower alkynyloxy" respectively refer to an alkynyl and lower alkynyl group bound through a single, terminal ether linkage.

The term "aryl" as used herein, and unless otherwise specified, refers to an aromatic group containing a single aromatic ring or multiple aromatic rings that are fused together, directly linked, or indirectly linked, such that the different aromatic rings are bound to a common group such as a methylene or ethylene moiety; or refers to a "heteroaryl" which refers to a "heteroatom containing aryl" in which at least one carbon atom of the aryl group is replaced with a heteroatom. Generally, aryl groups contain 5 to 24 carbon atoms, and typically, aryl groups contain 5 to 14 carbon atoms. Exemplary aryl groups contain one aromatic ring or two fused or linked aromatic rings, e.g., phenyl (Ph), naphthyl, biphenyl, diphenylether, diphenylamine, benzophenone, and the like. "Substituted aryl" or "substituted heteroaryl" refers to an aryl moiety substituted with one or more substituent groups, as defined herein. Examples of suitable substituted phenyl groups include, but are not limited to: mesityl or Mes (2,4,6-trimethylphenyl), IPP (2-isopropylphenyl) and DIPP (2,6-diisopropylphenyl).

The term "aryloxy" as used herein refers to an aryl group bound through a single, terminal ether linkage, wherein "aryl" is as defined above. An "aryloxy" group may be represented as —O-aryl where aryl is as defined above. Aryloxy groups contain 5 to 24 carbon atoms, or 5 to 14 carbon atoms. Examples of aryloxy groups include, without limitation, phenoxy, o-halo-phenoxy, m-halo-phenoxy, p-halo-phenoxy, o-methoxy-phenoxy, m-methoxy-phenoxy, p-methoxy-phenoxy, 2,4-dimethoxy-phenoxy, 3,4,5-trimethoxy-phenoxy, and the like.

The term "alkaryl" refers to an aryl group with an alkyl substituent, and the term "aralkyl" refers to an alkyl group with an aryl substituent, wherein "aryl" and "alkyl" are as defined above. Alkaryl and aralkyl groups contain 6 to 24 carbon atoms, or 6 to 16 carbon atoms. Alkaryl groups include, without limitation, p-methylphenyl, 2,4-dimethylphenyl, p-cyclohexylphenyl, 2,7-dimethylnaphthyl, 7-cyclooctylnaphthyl, 3-ethyl-cyclopenta-1,4-diene, and the like. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclo hexylmethyl, 4-benzylcyclohexylmethyl, and the like. The terms "alkaryloxy" and "aralkyloxy" refer to substituents of the formula —OR wherein R is alkaryl or aralkyl, respectively, as just defined.

The term "acyl" refers to substituents having the formula —(CO)-alkyl, —(CO)-aryl, —(CO)-aralkyl, —(CO)-alkaryl, —(CO)-alkenyl, or —(CO)-alkynyl, and the term "acyloxy" refers to substituents having the formula —O(CO)-alkyl, —O(CO)-aryl, —O(CO)-aralkyl, —O(CO)-alkaryl, —O(CO)-alkenyl, —O(CO)-alkynyl wherein "alkyl," "aryl," "aralkyl," "alkaryl," "alkenyl," and "alkynyl" are as defined above.

The terms "cyclic" and "ring" refer to alicyclic or aromatic groups that may or may not be substituted and/or heteroatom containing, and that may be monocyclic, bicyclic, or polycyclic. The term "alicyclic" is used in the conventional sense to refer to an aliphatic cyclic moiety, as opposed to an aromatic cyclic moiety, and may be monocyclic, bicyclic, or polycyclic.

The terms "halo" and "halogen" and "halide" are used in the conventional sense to refer to a chloro, bromo, fluoro, or iodo substituent.

"Hydrocarbyl" refers to univalent hydrocarbyl radicals containing 1 to about 30 carbon atoms, or 1 to about 24 carbon atoms, or 1 to about 12 carbon atoms, including linear, branched, cyclic, saturated, and unsaturated species, such as alkyl groups, alkenyl groups, alkynyl groups, aryl groups, and the like. The term "lower hydrocarbyl" intends a hydrocarbyl group of 1 to 6 carbon atoms, or 1 to 4 carbon atoms, and the term "hydrocarbylene" refers to a divalent hydrocarbyl moiety containing 1 to about 30 carbon atoms, or 1 to about 24 carbon atoms, or 1 to about 12 carbon atoms, including linear, branched, cyclic, saturated, and unsaturated species. The term "lower hydrocarbylene" refers to a hydrocarbylene group of 1 to 6 carbon atoms. "Substituted hydrocarbyl" refers to hydrocarbyl substituted with one or more substituent groups, and the terms "heteroatom-containing hydrocarbyl" and "heterohydrocarbyl" refer to hydrocarbyl in which at least one carbon atom is replaced with a heteroatom. Similarly, "substituted hydrocarbylene" refers to hydrocarbylene substituted with one or more substituent groups, and the terms "heteroatom-containing hydrocarbylene" and "heterohydrocarbylene" refer to hydrocarbylene in which at least one carbon atom is replaced with a heteroatom. Unless otherwise indicated, the term "hydrocarbyl" and "hydrocarbylene" are to be interpreted as including substituted and/or heteroatom-containing hydrocarbyl and heteroatom-containing hydrocarbylene moieties, respectively.

The term "heteroatom-containing" as in a "heteroatom-containing hydrocarbyl group" refers to a hydrocarbon molecule or a hydrocarbyl molecular fragment in which one or more carbon atoms is replaced with an atom other than carbon, e.g., nitrogen, oxygen, sulfur, phosphorus, or silicon, typically nitrogen, oxygen, or sulfur. Similarly, the term "heteroalkyl" refers to an alkyl substituent that is heteroatom-containing, the term "heterocyclic" refers to a cyclic substituent that is heteroatom-containing, the terms "heteroaryl" and "heteroaromatic" respectively refer to "aryl" and "aromatic" substituents that are heteroatom-containing, and the like. It should be noted that a "heterocyclic" group or compound may or may not be aromatic, and further that "heterocycles" may be monocyclic, bicyclic, or polycyclic as described above with respect to the term "aryl." Examples of heteroalkyl groups include without limitation alkoxyaryl, alkylsulfanyl-substituted alkyl, N-alkylated amino alkyl, and the like. Examples of heteroaryl substituents include without limitation pyrrolyl, pyrrolidinyl, pyridinyl, quinolinyl, indolyl, pyrimidinyl, imidazolyl, 1,2,4-triazolyl, tetrazolyl, etc., and examples of heteroatom-containing alicyclic groups include without limitation pyrrolidino, morpholino, piperazino, piperidino, etc.

By "substituted" as in "substituted hydrocarbyl," "substituted alkyl," "substituted aryl," and the like, as alluded to in some of the aforementioned definitions, is meant that in the hydrocarbyl, alkyl, aryl, or other moiety, at least one hydrogen atom bound to a carbon, or other atom, is replaced with one or more non-hydrogen substituents. Examples of such substituents include, without limitation: halo (X), hydroxyl (—OH), sulfhydryl (—SH), $C_1$-$C_{24}$ alkoxy (—O-alkyl), $C_2$-$C_{24}$ alkenyloxy (—O-alkenyl), $C_2$-$C_{24}$ alkynyloxy (—O-alkynyl), $C_5$-$C_{24}$ aryloxy (—O-aryl), $C_6$-$C_{24}$ aralkyloxy (aralkyl-O—), $C_6$-$C_{24}$ alkaryloxy (alkylaryl-O—), $C_2$-$C_{24}$ alkylcarbonyl (—CO-alkyl), $C_6$-$C_{24}$ arylcarbonyl (—CO-aryl), $C_2$-$C_{24}$ alkylcarbonyloxy (—O—CO-alkyl), $C_6$-$C_{24}$ arylcarbonyloxy (—O—CO-aryl), $C_2$-$C_{24}$ alkoxycarbonyl (—CO—O-alkyl), $C_6$-$C_{24}$ aryloxycarbonyl (—CO—O-aryl), halocarbonyl (—CO—X), $C_2$-$C_{24}$ alkylcarbonato (—O—CO—O-alkyl), $C_6$-$C_{24}$ arylcarbonato (—O—CO—O-aryl), carboxylic acid (—COOH), carbamoyl (—CO—$NH_2$), mono-($C_1$-$C_{24}$ alkyl)-substituted carbamoyl (—CO—NH($C_1$-$C_{24}$ alkyl)), di-($C_1$-$C_{24}$ alkyl)-substituted carbamoyl (—CO—N($C_1$-$C_{24}$ alkyl)$_2$), mono-($C_1$-$C_{24}$ haloalkyl)-substituted carbamoyl (—CO—NH($C_1$-$C_{24}$ haloalkyl)), di-($C_1$-$C_{24}$ haloalkyl)-substituted carbamoyl (—CO—N($C_1$-$C_{24}$ haloalkyl)$_2$), mono-($C_5$-$C_{24}$ aryl)-substituted carbamoyl (—CO—NH—($C_5$-$C_{24}$ aryl)), di-($C_5$-$C_{24}$ aryl)-substituted carbamoyl (—CO—N($C_5$-$C_{24}$ aryl)$_2$), N—($C_1$-$C_{24}$ alkyl) ($C_5$-$C_{24}$ aryl)-substituted carbamoyl (—(CO)—N($C_1$-$C_{24}$ alkyl)($C_5$-$C_{24}$ aryl)), thioether (RS—, where R includes without limitation $C_1$-$C_{24}$ alkyl, $C_5$-$C_{24}$ aryl, $C_6$-$C_{24}$ alkaryl, $C_6$-$C_{24}$ aralkyl, etc.), disulfide (R—S—S—, where R includes without limitation $C_1$-$C_{24}$ alkyl, $C_5$-$C_{24}$ aryl, $C_6$-$C_{24}$ alkaryl, $C_6$-$C_{24}$ aralkyl, etc.), thiocarbamoyl (—(CS)—$NH_2$), mono-($C_1$-$C_{24}$ alkyl)-substituted thiocarbamoyl (—(CS)—NH($C_1$-$C_{24}$ alkyl)), di-($C_1$-$C_{24}$ alkyl)-substituted thiocarbamoyl (—(CS)—N($C_1$-$C_{24}$ alkyl)$_2$), mono-($C_5$-$C_{24}$ aryl)-substituted thiocarbamoyl (—(CS)—NH—($C_5$-$C_{24}$ aryl)), di-($C_5$-$C_{24}$ aryl)-substituted thiocarbamoyl (—(CS)—N($C_5$-$C_{24}$ aryl)$_2$), N—($C_1$-$C_{24}$ alkyl)($C_5$-$C_{24}$ aryl)-substituted thiocarbamoyl (—(CS)—N($C_1$-$C_{24}$ alkyl)($C_5$-$C_{24}$ aryl)), carbamido (—NH—(CO)—$NH_2$), cyano (—C≡N), cyanato (—O—C≡N), thiocyanato (—S—C≡N), isocyanate (—N=C=O), thioisocyanate (—N=C=S), formyl (—(CO)—H), thioformyl (—(CS)—H), amino (—$NH_2$), mono-($C_1$-$C_{24}$ alkyl)-substituted amino (—NH($C_1$-$C_{24}$ alkyl)), di-($C_1$-$C_{24}$ alkyl)-substituted amino (—N($C_1$-$C_{24}$ alkyl)$_2$), mono-($C_5$-$C_{24}$ aryl)-substituted amino (—NH($C_5$-$C_{24}$ aryl)), di-($C_5$-$C_{24}$ aryl)-substituted amino (—N($C_5$-$C_{24}$ aryl)$_2$), —N—($C_1$-$C_{24}$ alkyl)($C_5$-$C_{24}$ aryl), $C_1$-$C_{24}$ alkylamido (—NH—(CO)—($C_1$-$C_{24}$ alkyl)), $C_5$-$C_{24}$ arylamido (—NH—(CO)—$C_5$-$C_{24}$ aryl), imino (—CR=NH where, R includes without limitation hydrogen, $C_1$-$C_{24}$ alkyl, $C_5$-$C_{24}$ aryl, $C_6$-$C_{24}$ alkaryl, $C_6$-$C_{24}$ aralkyl, etc.), $C_1$-$C_{24}$ alkylimino (—CR=N($C_1$-$C_{24}$ alkyl), where R includes without limitation hydrogen, $C_1$-$C_{24}$ alkyl, $C_5$-$C_{24}$ aryl, $C_6$-$C_{24}$ alkaryl, $C_6$-$C_{24}$ aralkyl), arylimino (—CR=N ($C_5$-$C_{24}$ aryl), where R includes without limitation hydrogen, $C_1$-$C_{20}$ alkyl, $C_5$-$C_{24}$ aryl, $C_6$-$C_{24}$ alkaryl, $C_6$-$C_{24}$ aralkyl), nitro (—$NO_2$), nitroso (—NO), nitrate (—$NO_3$), sulfo (—$SO_2$—OH), $C_1$-$C_{24}$ alkylsulfanyl (—S-alkyl; also termed "alkylthio"), $C_5$-$C_{24}$ arylsulfanyl (—S-aryl; also termed "arylthio"), $C_1$-$C_{24}$ alkylsulfinyl (—(SO)—($C_1$-$C_{24}$ alkyl)), $C_5$-$C_{24}$ arylsulfinyl (—(SO)—($C_5$-$C_{24}$ aryl)), $C_1$-$C_{24}$ alkylsulfonyl (—$SO_2$—($C_1$-$C_{24}$ alkyl)), $C_1$-$C_{24}$ monoalkylaminosulfonyl (—$SO_2$—N(H) ($C_1$-$C_{24}$ alkyl)), $C_1$-$C_{24}$ dialkylaminosulfonyl (—$SO_2$—N($C_1$-$C_{24}$ alkyl)$_2$), $C_5$-$C_{24}$ arylsulfonyl (—$SO_2$—($C_5$-$C_{24}$ aryl)), boryl (—$BH_2$), borono (—$B(OH)_2$), boronato (—$B(OR)_2$ where R includes without limitation $C_1$-$C_{24}$ alkyl or other hydrocarbyl), phosphono (—P(O)(OH)$_2$), phospho (—$PO_2$), phosphino (—$PH_2$), silyl (—$SiR_3$, wherein R is hydrogen or hydrocarbyl), silyloxy (—O-silyl), styrenyl, hydrocarbyl moieties include without limitation $C_1$-$C_{24}$ alkyl, $C_1$-$C_{12}$ alkyl, $C_1$-$C_6$ alkyl groups, $C_2$-$C_{24}$ alkenyl, $C_2$-$C_{12}$ alkenyl, $C_2$-$C_6$ alkenyl, $C_2$-$C_{24}$ alkynyl, $C_2$-$C_{12}$ alkynyl, $C_2$-$C_6$ alkynyl, $C_5$-$C_{24}$ aryl, $C_5$-$C_{14}$ aryl, $C_6$-$C_{24}$ alkaryl, $C_6$-$C_{16}$ alkaryl, $C_6$-$C_{24}$ aralkyl, $C_6$-$C_{16}$ aralkyl.

By "functionalized" as in "functionalized hydrocarbyl," "functionalized alkyl," "functionalized olefin," "functionalized cyclic olefin," and the like, is meant that in the hydrocarbyl, alkyl, olefin, cyclic olefin, or other moiety, at least one hydrogen atom bound to a carbon (or other) atom is replaced with one or more functional groups such as those described hereinabove. The term "functional group" is meant to include any functional species that is suitable for the uses described herein.

The term "nil" as used herein means nonexistent.

In addition, the aforementioned functional groups may, if a particular group permits, be further substituted with one or more additional functional groups or with one or more hydrocarbyl moieties such as those specifically mentioned above. Analogously, the above-mentioned hydrocarbyl moieties may be further substituted with one or more functional groups or additional hydrocarbyl moieties as noted above.

The term "internal olefin" as used herein means an olefin wherein each of the olefinic carbons is substituted by at least one non-hydrogen substituent. The internal olefin may be di-substituted, tri-substituted, or tetra-substituted. The "internal olefin" may have an E-configuration or a Z-configuration.

The term "terminal olefin" as used herein means an olefin wherein one of the olefinic carbons is substituted by at least one non-hydrogen substituent. The terminal olefin may be di-substituted or mono-substituted.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

Substituents and functional groups may be protected in cases where the substituent and/or the functional group interfere with the metathesis catalyst, or the reaction conditions, and any of the protecting groups commonly used in the art may be employed. Acceptable protecting groups may be found, for example, in Greene et al., Greene's Protective Groups in Organic Synthesis, 4th Ed. (New York: Wiley, 2007).

Olefin Metathesis Catalysts

In one embodiment, the invention provides an olefin metathesis catalyst represented by the structure of Formula (I):

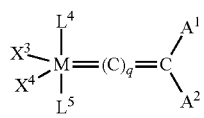

Formula (I)

wherein:

M is a Group 8 transition metal;

$L^4$ and $L^5$ are independently N-heterocyclic carbene (NHC) ligands;

q is 0 or 1;

$X^3$ and $X^4$ are independently anionic ligands; and $A^1$ and $A^2$ are independently selected from hydrogen, hydrocarbyl, substituted hydrocarbyl, heteroatom-containing hydrocarbyl, substituted heteroatom-containing hydrocarbyl, and functional groups.

In one embodiment, the invention provides, an olefin metathesis catalyst represented by the structure of Formula (I), wherein:

M is a Ru or Os;

q is 0 or 1;

$X^3$ is Cl, F, Br or I;

$X^4$ is Cl, F, Br or I;

$L^4$ and $L^5$ are independently diaminocarbene ligands selected from:

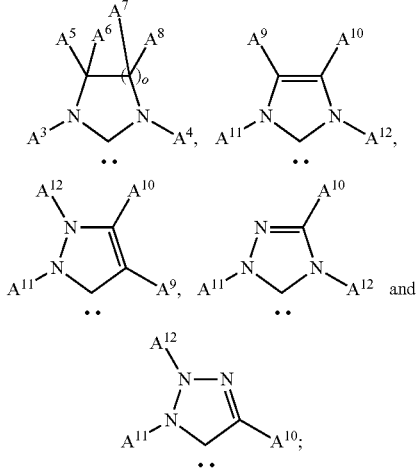

o is 1 or 2;

$A^3$, $A^4$, $A^{11}$ and $A^{12}$ are independently unsubstituted $C_5$-$C_{24}$ aryl or $C_5$-$C_{24}$ aryl substituted with at least one substituent selected from halo (X), hydroxyl (—OH), sulfhydryl (—SH), $C_1$-$C_{24}$ alkoxy (—O-alkyl), $C_2$-$C_{24}$ alkenyloxy (—O-alkenyl), $C_2$-$C_{24}$ alkynyloxy (-alkynyl), $C_5$-$C_{24}$ aryloxy (—O-aryl), $C_6$-$C_{24}$ aralkyloxy (aralkyl-O—), $C_6$-$C_{24}$ alkaryloxy (alkylaryl-O—), $C_2$-$C_{24}$ alkylcarbonyl (—CO-alkyl), $C_6$-$C_{24}$ arylcarbonyl (—CO-aryl), $C_2$-$C_{24}$ alkylcarbonyloxy (—O—CO— alkyl), $C_6$-$C_{24}$ arylcarbonyloxy (—O—CO-aryl), $C_2$-$C_{24}$ alkoxycarbonyl (—CO—O-alkyl), $C_6$-$C_{24}$ aryloxycarbonyl (—CO—O-aryl), halocarbonyl (—CO—X), $C_2$-$C_{24}$ alkylcarbonato (—O—CO—O-alkyl), $C_6$-$C_{24}$ arylcarbonato (—O—CO—O-aryl), carboxylic acid (—COOH), carbamoyl (—CO—$NH_2$), mono-($C_1$-$C_{24}$ alkyl)-substituted carbamoyl (—CO—NH($C_1$-$C_{24}$ alkyl)), di-($C_1$-$C_{24}$ alkyl)-substituted carbamoyl (—CO—N($C_1$-$C_{24}$ alkyl)$_2$), mono-($C_1$-$C_{24}$ haloalkyl)-substituted carbamoyl (—CO—NH($C_1$-$C_{24}$ haloalkyl)), di-($C_1$-$C_{24}$ haloalkyl)-substituted carbamoyl (—CO—N($C_1$-$C_{24}$ haloalkyl)$_2$), mono-($C_5$-$C_{24}$ aryl)-substituted carbamoyl (—CO—NH—($C_5$-$C_{24}$ aryl)), di-($C_5$-$C_{24}$ aryl)-substituted carbamoyl (—CO—N($C_5$-$C_{24}$ aryl)$_2$), N—($C_1$-$C_{24}$ alkyl) ($C_5$-$C_{24}$ aryl)-substituted carbamoyl (—(CO)—N($C_1$-$C_{24}$ alkyl)($C_5$-$C_{24}$ aryl)), thioether (RS—, where R includes without limitation $C_1$-$C_{24}$ alkyl, $C_5$-$C_{24}$ aryl, $C_6$-$C_{24}$ alkaryl, $C_6$-$C_{24}$ aralkyl, etc.), disulfide (R—S—S—, where R includes without limitation $C_1$-$C_{24}$ alkyl, $C_5$-$C_{24}$ aryl, $C_6$-$C_{24}$ alkaryl, $C_6$-$C_{24}$ aralkyl, etc.), thiocarbamoyl (—(CS)—$NH_2$), mono-($C_1$-$C_{24}$ alkyl)-substituted thiocarbamoyl (—(CS)—NH($C_1$-$C_{24}$ alkyl)), di-($C_1$-$C_{24}$ alkyl)-substituted thiocarbamoyl (—(CS)—N($C_1$-$C_{24}$ alkyl)$_2$), mono-($C_5$-$C_{24}$ aryl)-substituted thiocarbamoyl (—(CS)—NH—($C_5$-$C_{24}$ aryl)), di-($C_5$-$C_{24}$ aryl)-substituted thiocarbamoyl (—(CS)—N($C_5$-$C_{24}$ aryl)$_2$), N—($C_1$-$C_{24}$ alkyl)($C_5$-$C_{24}$ aryl)-substituted thiocarbamoyl (—(CS)—N($C_1$-$C_{24}$ alkyl)($C_5$-$C_{24}$ aryl)), carbamido (—NH—(CO)—NH$_2$), cyano (—C≡N), cyanato (—O—C≡N), thiocyanato (—S—C≡N), isocyanate (—N=C=O), thioisocyanate (—N=C=S), formyl (—(CO)—H), thioformyl (—(CS)—H), amino (—NH$_2$), mono-($C_1$-$C_{24}$ alkyl)-substituted amino (—NH($C_1$-$C_{24}$ alkyl)), di-($C_1$-$C_{24}$ alkyl)-substituted amino (—N($C_1$-$C_{24}$ alkyl)$_2$), mono-($C_5$-$C_{24}$ aryl)-substituted amino (—NH($C_1$-$C_{24}$ aryl)), di-($C_1$-$C_{24}$ aryl)-substituted amino (—N($C_5$-$C_{24}$ aryl)$_2$), —N—($C_1$-$C_{24}$ alkyl)($C_5$-$C_{24}$ aryl), $C_1$-$C_{24}$ alkylamido (—NH—(CO)—($C_1$-$C_{24}$ alkyl)), $C_5$-$C_{24}$ arylamido (—NH—(CO)—$C_5$-$C_{24}$ aryl), imino (—CR=NH where, R includes without limitation hydrogen, $C_1$-$C_{24}$ alkyl, $C_5$-$C_{24}$ aryl, $C_6$-$C_{24}$ alkaryl, $C_6$-$C_{24}$ aralkyl, etc.), $C_1$-$C_{24}$ alkylimino (—CR=N($C_1$-$C_{24}$ alkyl), where R includes without limitation hydrogen, $C_1$-$C_{24}$ alkyl, $C_5$-$C_{24}$ aryl, $C_6$-$C_{24}$ alkaryl, $C_6$-$C_{24}$ aralkyl), arylimino (—CR=N ($C_5$-$C_{24}$ aryl), where R includes without limitation hydrogen, $C_1$-$C_{20}$ alkyl, $C_5$-$C_{24}$ aryl, $C_6$-$C_{24}$ alkaryl, $C_6$-$C_{24}$ aralkyl), nitro (—NO$_2$), nitroso (—NO), nitrate (—NO$_3$), sulfo (—SO$_2$—OH), $C_1$-$C_{24}$ alkylsulfanyl (—S-alkyl; also termed "alkylthio"), $C_5$-$C_{24}$ arylsulfanyl (—S-aryl; also termed "arylthio"), $C_1$-$C_{24}$ alkylsulfinyl (—(SO)—($C_1$-$C_{24}$ alkyl)), $C_5$-$C_{24}$ arylsulfinyl (—(SO)—($C_5$-$C_{24}$ aryl)), $C_1$-$C_{24}$ alkylsulfonyl (—SO$_2$—($C_1$-$C_{24}$ alkyl)), $C_1$-$C_{24}$ monoalkylaminosulfonyl (—SO$_2$—N(H) ($C_1$-$C_{24}$ alkyl)), $C_1$-$C_{24}$ dialkylaminosulfonyl (—SO$_2$—N($C_1$-$C_{24}$ alkyl)$_2$), $C_5$-$C_{24}$ arylsulfonyl (—SO$_2$—($C_5$-$C_{24}$ aryl)), boryl (—BH$_2$), borono (—B(OH)$_2$), boronato (—B(OR)$_2$ where R includes without limitation $C_1$-$C_{24}$ alkyl or other hydrocarbyl), phosphono (—P(O)(OH)$_2$), phospho (—PO$_2$), phosphino (—PH$_2$), silyl (—SiR$_3$, wherein R is hydrogen or hydrocarbyl), silyloxy (—O-silyl), styrenyl, $C_1$-$C_{24}$ alkyl, $C_2$-$C_{24}$ alkenyl, $C_2$-$C_{24}$ alkynyl, $C_5$-$C_{24}$ aryl, $C_6$-$C_{24}$ alkaryl, and $C_6$-$C_{24}$ aralkyl;

$A^5$, $A^6$, $A^7$, $A^8$, $A^9$ and $A^{10}$ are independently hydrogen, halo (X), hydroxyl (—OH), sulfhydryl (—SH), $C_1$-$C_{24}$ alkoxy (—O-alkyl), $C_2$-$C_{24}$ alkenyloxy (—O-alkenyl), $C_2$-$C_{24}$ alkynyloxy (—O-alkynyl), $C_5$-$C_{24}$ aryloxy (—O-aryl), $C_6$-$C_{24}$ aralkyloxy (aralkyl-O—), $C_6$-$C_{24}$ alkaryloxy (alkylaryl-O—), $C_2$-$C_{24}$ alkylcarbonyl (—CO-alkyl), $C_6$-$C_{24}$ arylcarbonyl (—CO-aryl), $C_2$-$C_{24}$ alkylcarbonyloxy (—O—CO-alkyl), $C_6$-$C_{24}$ arylcarbonyloxy (—O—CO-aryl), $C_2$-$C_{24}$ alkoxycarbonyl (—CO—O-alkyl), $C_6$-$C_{24}$ aryloxycarbonyl (—CO—O-aryl), halocarbonyl (—CO—X), $C_2$-$C_{24}$ alkylcarbonato (—O—CO—O-alkyl), $C_6$-$C_{24}$ arylcarbonato (—O—CO—O-aryl), carboxylic acid (—COOH), carbamoyl (—CO—NH$_2$), mono-($C_1$-$C_{24}$ alkyl)-substituted carbamoyl (—CO—NH($C_1$-$C_{24}$ alkyl)), di-($C_1$-$C_{24}$ alkyl)-substituted carbamoyl (—CO—N($C_1$-$C_{24}$ alkyl)$_2$), mono-($C_1$-$C_{24}$ haloalkyl)-substituted carbamoyl (—CO—NH($C_1$-$C_{24}$ haloalkyl)), di-($C_1$-$C_{24}$ haloalkyl)-substituted carbamoyl (—CO—N($C_1$-$C_{24}$ haloalkyl)$_2$), mono-($C_5$-$C_{24}$ aryl)-substituted carbamoyl (—CO—NH—($C_1$-$C_{24}$ aryl)), di-($C_5$-$C_{24}$ aryl)-substituted carbamoyl (—CO—N ($C_1$-$C_{24}$ aryl)$_2$), N—($C_1$-$C_{24}$ alkyl)($C_5$-$C_{24}$ aryl)-substituted carbamoyl (—(CO)—N($C_1$-$C_{24}$ alkyl)($C_5$-$C_{24}$ aryl)), thioether (RS—, where R includes without limitation $C_1$-$C_{24}$ alkyl, $C_5$-$C_{24}$ aryl, $C_6$-$C_{24}$ alkaryl, $C_6$-$C_{24}$ aralkyl, etc.), disulfide (R—S—S—, where R includes without limitation $C_1$-$C_{24}$ alkyl, $C_5$-$C_{24}$ aryl, $C_6$-$C_{24}$ alkaryl, $C_6$-$C_{24}$ aralkyl, etc.), thiocarbamoyl (—(CS)—NH$_2$), mono-($C_1$-$C_{24}$ alkyl)-substituted thiocarbamoyl (—(CS)—NH($C_1$-$C_{24}$ alkyl)), di-($C_1$-$C_{24}$ alkyl)-substituted thiocarbamoyl (—(CS)—N($C_1$-$C_{24}$ alkyl)$_2$), mono-($C_5$-$C_{24}$ aryl)-substituted thiocarbamoyl (—(CS)—NH—($C_5$-$C_{24}$ aryl)), di-($C_5$-$C_{24}$ aryl)-substituted thiocarbamoyl (—(CS)—N($C_5$-$C_{24}$ aryl)$_2$), N—($C_1$-$C_{24}$ alkyl)($C_5$-$C_{24}$ aryl)-substituted thiocarbamoyl (—(CS)—N ($C_1$-$C_{24}$ alkyl)($C_5$-$C_{24}$ aryl)), carbamido (—NH—(CO)—NH$_2$), cyano (—C≡N), cyanato (—O—C≡N), thiocyanato (—S—C≡N), isocyanate (—N=C=O), thioisocyanate (—N=C=S), formyl (—(CO)—H), thioformyl (—(CS)—H), amino (—NH$_2$), mono-($C_1$-$C_{24}$ alkyl)-substituted amino (—NH($C_1$-$C_{24}$ alkyl)), di-($C_1$-$C_{24}$ alkyl)-substituted amino (—N($C_1$-$C_{24}$ alkyl)$_2$), mono-($C_5$-$C_{24}$ aryl)-substituted amino (—NH($C_5$-$C_{24}$ aryl)), di-($C_5$-$C_{24}$ aryl)-substituted amino (—N($C_5$-$C_{24}$ aryl)$_2$), —N—($C_1$-$C_{24}$ alkyl)($C_5$-$C_{24}$ aryl), $C_1$-$C_{24}$ alkylamido (—NH—(CO)—($C_1$-$C_{24}$ alkyl)), $C_5$-$C_{24}$ arylamido (—NH—(CO)—$C_5$-$C_{24}$ aryl), imino (—CR=NH where, R includes without limitation hydrogen, $C_1$-$C_{24}$ alkyl, $C_5$-$C_{24}$ aryl, $C_6$-$C_{24}$ alkaryl, $C_6$-$C_{24}$ aralkyl, etc.), $C_1$-$C_{24}$ alkylimino (—CR=N($C_1$-$C_{24}$ alkyl), where R includes without limitation hydrogen, $C_1$-$C_{24}$ alkyl, $C_5$-$C_{24}$ aryl, $C_6$-$C_{24}$ alkaryl, $C_6$-$C_{24}$ aralkyl), arylimino (—CR=N ($C_5$-$C_{24}$ aryl), where R includes without limitation hydrogen, $C_1$-$C_{20}$ alkyl, $C_5$-$C_{24}$ aryl, $C_6$-$C_{24}$ alkaryl, $C_6$-$C_{24}$ aralkyl), nitro (—NO$_2$), nitroso (—NO), nitrate (—NO$_3$), sulfo (—SO$_2$—OH), $C_1$-$C_{24}$ alkylsulfanyl (—S-alkyl; also termed "alkylthio"), $C_5$-$C_{24}$ arylsulfanyl (—S-aryl; also termed "arylthio"), $C_1$-$C_{24}$ alkylsulfinyl (—(SO)—($C_1$-$C_{24}$ alkyl)), $C_5$-$C_{24}$ arylsulfinyl (—(SO)—($C_5$-$C_{24}$ aryl)), $C_1$-$C_{24}$ alkylsulfonyl (—SO$_2$—($C_1$-$C_{24}$ alkyl)), $C_1$-$C_{24}$ monoalkylaminosulfonyl (—SO$_2$—N(H) ($C_1$-$C_{24}$ alkyl)), $C_1$-$C_{24}$ dialkylaminosulfonyl (—SO$_2$—N($C_1$-$C_{24}$ alkyl)$_2$), $C_5$-$C_{24}$ arylsulfonyl (—SO$_2$—($C_5$-$C_{24}$ aryl)), boryl (—BH$_2$), borono (—B(OH)$_2$), boronato (—B(OR)$_2$ where R includes without limitation $C_1$-$C_{24}$ alkyl or other hydrocarbyl), phosphono (—P(O)(OH)$_2$), phospho (—PO$_2$), phosphino (—PH$_2$), silyl (—SiR$_3$, wherein R is hydrogen or hydrocarbyl), silyloxy (—O-silyl), styrenyl, hydrocarbyl moieties include without limitation $C_1$-$C_{24}$ alkyl, $C_1$-$C_{12}$ alkyl, $C_1$-$C_6$ alkyl groups, $C_2$-$C_{24}$ alkenyl, $C_2$-$C_{12}$ alkenyl, $C_2$-$C_6$ alkenyl, $C_2$-$C_{24}$ alkynyl, $C_2$-$C_{12}$ alkynyl, $C_2$-$C_6$ alkynyl, $C_5$-$C_{24}$ aryl, $C_5$-$C_{14}$ aryl, $C_6$-$C_{24}$ alkaryl, $C_6$-$C_{16}$ alkaryl, $C_6$-$C_{24}$ aralkyl, $C_6$-$C_{16}$ aralkyl;

$A^1$ is hydrogen; and $A^2$ is hydrocarbyl, substituted hydrocarbyl, heteroatom-containing hydrocarbyl, substituted heteroatom-containing hydrocarbyl, halo (X), hydroxyl (—OH), sulfhydryl (—SH), $C_1$-$C_{24}$ alkoxy (—O-alkyl), $C_2$-$C_{24}$ alkenyloxy (—O-alkenyl), $C_2$-$C_{24}$ alkynyloxy (—O-alkynyl), $C_5$-$C_{24}$ aryloxy (—O-aryl), $C_6$-$C_{24}$ aralkyloxy (aralkyl-O—), $C_6$-$C_{24}$ alkaryloxy (alkylaryl-O—), $C_2$-$C_{24}$ alkylcarbonyl (—CO-alkyl), $C_6$-$C_{24}$ arylcarbonyl (—CO-aryl), $C_2$-$C_{24}$ alkylcarbonyloxy (—O—CO-alkyl), $C_6$-$C_{24}$ arylcarbonyloxy (—O—CO-aryl), $C_2$-$C_{24}$ alkoxycarbonyl (—CO—O-alkyl), $C_6$-$C_{24}$ aryloxycarbonyl (—CO—O-aryl), halocarbonyl (—CO—X), $C_2$-$C_{24}$ alkylcarbonato (—O—CO—O-alkyl), $C_6$-$C_{24}$ arylcarbonato (—O—CO—O-aryl), carboxylic acid (—COOH), carbamoyl (—CO—NH$_2$), mono-($C_1$-$C_{24}$ alkyl)-substituted carbamoyl (—CO—NH($C_1$-$C_{24}$ alkyl)), di-($C_1$-$C_{24}$ alkyl)-substituted carbamoyl (—CO—N($C_1$-$C_{24}$ alkyl)$_2$), mono-($C_1$-$C_{24}$ haloalkyl)-substituted carbamoyl (—CO—NH($C_1$-$C_{24}$ haloalkyl)), di-($C_1$-$C_{24}$ haloalkyl)-substituted carbamoyl (—CO—N($C_1$-$C_{24}$ haloalkyl)$_2$), mono-($C_5$-$C_{24}$ aryl)-substituted carbamoyl (—CO—NH—($C_5$-$C_{24}$ aryl)), di-($C_5$-$C_{24}$ aryl)-substituted carbamoyl (—CO—N ($C_5$-$C_{24}$ aryl)$_2$), N—($C_1$-$C_{24}$ alkyl)($C_5$-$C_{24}$ aryl)-substituted carbamoyl (—(CO)—N($C_1$-$C_{24}$ alkyl)($C_5$-$C_{24}$ aryl)), thioether (RS—, where R includes without limitation $C_1$-$C_{24}$ alkyl, $C_5$-$C_{24}$ aryl, $C_6$-$C_{24}$ alkaryl, $C_6$-$C_{24}$ aralkyl, etc.), disulfide (R—S—S—, where R includes without limitation $C_1$-$C_{24}$ alkyl, $C_5$-$C_{24}$ aryl, $C_6$-$C_{24}$ alkaryl, $C_6$-$C_{24}$ aralkyl, etc.), thiocarbamoyl (—(CS)—$NH_2$), mono-($C_1$-$C_{24}$ alkyl)-substituted thiocarbamoyl (—(CS)—NH($C_1$-$C_{24}$ alkyl)), di-($C_1$-$C_{24}$ alkyl)-substituted thiocarbamoyl (—(CS)—N($C_1$-$C_{24}$ alkyl)$_2$), mono-($C_5$-$C_{24}$ aryl)-substituted thiocarbamoyl (—(CS)—NH—($C_5$-$C_{24}$ aryl)), di-($C_5$-$C_{24}$ aryl)-substituted thiocarbamoyl (—(CS)—N($C_5$-$C_{24}$ aryl)$_2$), N—($C_1$-$C_{24}$ alkyl)($C_5$-$C_{24}$ aryl)-substituted thiocarbamoyl (—(CS)—N($C_1$-$C_{24}$ alkyl)($C_5$-$C_{24}$ aryl)), carbamido (—NH—(CO)—$NH_2$), cyano (—C≡N), cyanato (—O—C≡N), thiocyanato (—S—C≡N), isocyanate (—N=C=O), thioisocyanate (—N=C=S), formyl (—(CO)—H), thioformyl (—(CS)—H), amino (—$NH_2$), mono-($C_1$-$C_{24}$ alkyl)-substituted amino (—NH($C_1$-$C_{24}$ alkyl)), di-($C_1$-$C_{24}$ alkyl)-substituted amino (—N($C_1$-$C_{24}$ alkyl)$_2$), mono-($C_5$-$C_{24}$ aryl)-substituted amino (—NH($C_5$-$C_{24}$ aryl)), di-($C_5$-$C_{24}$ aryl)-substituted amino (—N($C_5$-$C_{24}$ aryl)$_2$), —N—($C_1$-$C_{24}$ alkyl)($C_5$-$C_{24}$ aryl), $C_1$-$C_{24}$ alkylamido (—NH—(CO)—($C_1$-$C_{24}$ alkyl)), $C_5$-$C_{24}$ arylamido (—NH—(CO)—$C_5$-$C_{24}$ aryl), imino (—CR=NH where, R includes without limitation hydrogen, $C_1$-$C_{24}$ alkyl, $C_5$-$C_{24}$ aryl, $C_6$-$C_{24}$ alkaryl, $C_6$-$C_{24}$ aralkyl, etc.), $C_1$-$C_{24}$ alkylimino (—CR=N($C_1$-$C_{24}$ alkyl), where R includes without limitation hydrogen, $C_1$-$C_{24}$ alkyl, $C_5$-$C_{24}$ aryl, $C_6$-$C_{24}$ alkaryl, $C_6$-$C_{24}$ aralkyl), arylimino (—CR=N ($C_5$-$C_{24}$ aryl), where R includes without limitation hydrogen, $C_1$-$C_{20}$ alkyl, $C_5$-$C_{24}$ aryl, $C_6$-$C_{24}$ alkaryl, $C_6$-$C_{24}$ aralkyl), nitro (—$NO_2$), nitroso (—NO), nitrate (—$NO_3$), sulfo (—$SO_2$—OH), $C_1$-$C_{24}$ alkylsulfanyl (—S-alkyl; also termed "alkylthio"), $C_5$-$C_{24}$ arylsulfanyl (—S-aryl; also termed "arylthio"), $C_1$-$C_{24}$ alkylsulfinyl (—(SO)—($C_1$-$C_{24}$ alkyl)), $C_5$-$C_{24}$ arylsulfinyl (—(SO)—($C_5$-$C_{24}$ aryl)), $C_1$-$C_{24}$ alkylsulfonyl (—$SO_2$—($C_1$-$C_{24}$ alkyl)), $C_1$-$C_{24}$ monoalkylaminosulfonyl (—$SO_2$—N(H) ($C_1$-$C_{24}$ alkyl)), $C_1$-$C_{24}$ dialkylaminosulfonyl (—$SO_2$—N($C_1$-$C_{24}$ alkyl)$_2$), $C_5$-$C_{24}$ arylsulfonyl (—$SO_2$—($C_5$-$C_{24}$ aryl)), boryl (—$BH_2$), borono (—$B(OH)_2$), boronato (—$B(OR)_2$ where R includes without limitation $C_1$-$C_{24}$ alkyl or other hydrocarbyl), phosphono (—P(O)(OH)$_2$), phospho (—$PO_2$), phosphino (—$PH_2$), silyl (—$SiR_3$, wherein R is hydrogen or hydrocarbyl), silyloxy (—O-silyl), styrenyl, $C_1$-$C_{24}$ alkyl, $C_2$-$C_{24}$ alkenyl, $C_2$-$C_{24}$ alkynyl, $C_5$-$C_{24}$ aryl, $C_6$-$C_{24}$ alkaryl, and $C_6$-$C_{24}$ aralkyl.

In one embodiment, the invention provides, an olefin metathesis catalyst represented by the structure of Formula (I), wherein:

M is a Ru;
q is 0;
$X^3$ is Cl;
$X^4$ is Cl;
$L^4$ and $L^5$ are independently diaminocarbene ligands:

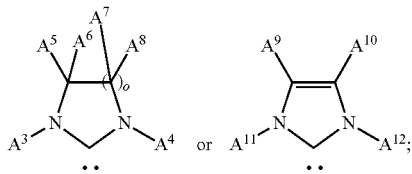

$A^3$, $A^4$, $A^{11}$ and $A^{12}$ are independently unsubstituted phenyl or phenyl substituted with at least one substituent selected from halo (X), hydroxyl (—OH), $C_1$-$C_{24}$ alkoxy (—O-alkyl), $C_5$-$C_{24}$ aryloxy (—O-aryl), $C_6$-$C_{24}$ aralkyloxy (aralkyl-O—), $C_6$-$C_{24}$ alkaryloxy (alkylaryl-O—), $C_2$-$C_{24}$ alkylcarbonyl (—CO-alkyl), $C_6$-$C_{24}$ arylcarbonyl (—CO-aryl), $C_2$-$C_{24}$ alkylcarbonyloxy (—O—CO— alkyl), $C_6$-$C_{24}$ arylcarbonyloxy (—O—CO-aryl), $C_2$-$C_{24}$ alkoxycarbonyl (—CO—O-alkyl), $C_6$-$C_{24}$ aryloxycarbonyl (—CO—O-aryl), carboxylic acid (—COOH), carbamoyl (—CO—$NH_2$), mono-($C_1$-$C_{24}$ alkyl)-substituted carbamoyl (—CO—NH($C_1$-$C_{24}$ alkyl)), di-($C_1$-$C_{24}$ alkyl)-substituted carbamoyl (—CO—N($C_1$-$C_{24}$ alkyl)$_2$), thioether (RS—, where R includes without limitation $C_1$-$C_{24}$ alkyl, $C_5$-$C_{24}$ aryl, $C_6$-$C_{24}$ alkaryl, $C_6$-$C_{24}$ aralkyl, etc.), thiocarbamoyl (—(CS)—$NH_2$), mono-($C_1$-$C_{24}$ alkyl)-substituted thiocarbamoyl (—(CS)—NH($C_1$-$C_{24}$ alkyl)), di-($C_1$-$C_{24}$ alkyl)-substituted thiocarbamoyl (—(CS)—N($C_1$-$C_{24}$ alkyl)$_2$), carbamido (—NH—(CO)—$NH_2$), cyano (—C≡N), cyanato (—O—C≡N), amino (—$NH_2$), mono-($C_1$-$C_{24}$ alkyl)-substituted amino (—NH($C_1$-$C_{24}$ alkyl)), di-($C_1$-$C_{24}$ alkyl)-substituted amino (—N($C_1$-$C_{24}$ alkyl)$_2$), mono-($C_5$-$C_{24}$ aryl)-substituted amino (—NH($C_5$-$C_{24}$ aryl)), di-($C_5$-$C_{24}$ aryl)-substituted amino (—N($C_5$-$C_{24}$ aryl)$_2$), —N—($C_1$-$C_{24}$ alkyl)($C_5$-$C_{24}$ aryl), $C_1$-$C_{24}$ alkylamido (—NH—(CO)—($C_1$-$C_{24}$ alkyl)), $C_5$-$C_{24}$ arylamido (—NH—(CO)—$C_5$-$C_{24}$ aryl), nitro (—$NO_2$), nitroso (—NO), nitrate (—$NO_3$), sulfo (—$SO_2$—OH), $C_1$-$C_6$ alkyl, $C_2$-$C_6$ alkenyl, $C_2$-$C_6$ alkynyl, $C_5$-$C_{10}$ aryl, $C_6$-$C_{16}$ alkaryl, and $C_6$-$C_{16}$ aralkyl;

$A^5$, $A^6$, $A^7$, $A^8$, $A^9$ and $A^{10}$ are independently hydrogen, halo (X), hydroxyl (—OH), $C_1$-$C_{24}$ alkoxy (—O-alkyl), $C_5$-$C_{24}$ aryloxy (—O-aryl), $C_6$-$C_{24}$ aralkyloxy (aralkyl-O—), $C_6$-$C_{24}$ alkaryloxy (alkylaryl-O—), $C_2$-$C_{24}$ alkylcarbonyl (—CO-alkyl), $C_6$-$C_{24}$ arylcarbonyl (—CO-aryl), $C_2$-$C_{24}$ alkylcarbonyloxy (—O—CO-alkyl), $C_6$-$C_{24}$ arylcarbonyloxy (—O—CO-aryl), $C_2$-$C_{24}$ alkoxycarbonyl (—CO—O-alkyl), $C_6$-$C_{24}$ aryloxycarbonyl (—CO—O-aryl), carboxylic acid (—COOH), carbamoyl (—CO—$NH_2$), mono-($C_1$-$C_{24}$ alkyl)-substituted carbamoyl (—CO—NH($C_1$-$C_{24}$ alkyl)), di-($C_1$-$C_{24}$ alkyl)-substituted carbamoyl (—CO—N($C_1$-$C_{24}$ alkyl)$_2$), thioether (RS—, where R includes without limitation $C_1$-$C_{24}$ alkyl, $C_5$-$C_{24}$ aryl, $C_6$-$C_{24}$ alkaryl, $C_6$-$C_{24}$ aralkyl, etc.), thiocarbamoyl (—(CS)—$NH_2$), mono-($C_1$-$C_{24}$ alkyl)-substituted thiocarbamoyl (—(CS)—NH($C_1$-$C_{24}$ alkyl)), di-($C_1$-$C_{24}$ alkyl)-substituted thiocarbamoyl (—(CS)—N($C_1$-$C_{24}$ alkyl)$_2$), carbamido (—NH—(CO)—$NH_2$), cyano (—C≡N), cyanato (—O—C≡N), amino (—$NH_2$), mono-($C_1$-$C_{24}$ alkyl)-substituted amino (—NH($C_1$-$C_{24}$ alkyl)), di-($C_1$-$C_{24}$ alkyl)-substituted amino (—N($C_1$-$C_{24}$ alkyl)$_2$), mono-($C_5$-$C_{24}$ aryl)-substituted amino (—NH($C_5$-$C_{24}$ aryl)), di-($C_5$-$C_{24}$ aryl)-substituted amino (—N($C_5$-$C_{24}$ aryl)$_2$), —N—($C_1$-$C_{24}$ alkyl)($C_5$-$C_{24}$ aryl), $C_1$-$C_{24}$ alkylamido (—NH—(CO)—($C_1$-$C_{24}$ alkyl)), $C_5$-$C_{24}$ arylamido (—NH—(CO)—$C_5$-$C_{24}$ aryl), nitro (—$NO_2$), nitroso (—NO), nitrate (—$NO_3$), sulfo (—$SO_2$—OH), $C_1$-$C_6$ alkyl, $C_2$-$C_6$ alkenyl, $C_2$-$C_6$ alkynyl, $C_5$-$C_{10}$ aryl, $C_6$-$C_{16}$ alkaryl, and $C_6$-$C_{16}$ aralkyl;

o is 1;
$A^1$ is hydrogen; and
$A^2$ is hydrocarbyl, substituted with at least one substituent selected from: halo (X), hydroxyl (—OH), $C_1$-$C_{24}$ alkoxy (—O-alkyl), $C_5$-$C_{24}$ aryloxy (—O-aryl), $C_6$-$C_{24}$ aralkyloxy (aralkyl-O—), $C_6$-$C_{24}$ alkaryloxy (alkylaryl-O—), $C_2$-$C_{24}$ alkylcarbonyl (—CO-alkyl), $C_6$-$C_{24}$ arylcarbonyl (—CO-aryl), $C_2$-$C_{24}$ alkylcarbonyloxy (—O—CO-alkyl), $C_6$-$C_{24}$ arylcarbonyloxy (—O—CO-aryl), $C_2$-$C_{24}$ alkoxycarbonyl (—CO—O-alkyl), $C_6$-$C_{24}$ aryloxycarbonyl (—CO—O-aryl), carboxylic acid (—COOH), carbamoyl (—CO—$NH_2$), mono-($C_1$-$C_{24}$ alkyl)-substituted carbamoyl (—CO—NH($C_1$-$C_{24}$ alkyl)), di-($C_1$-$C_{24}$ alkyl)-substituted carbamoyl (—CO—N($C_1$-$C_{24}$ alkyl)$_2$), thioether (RS—, where R includes without limitation $C_1$-$C_{24}$ alkyl, $C_5$-$C_{24}$ aryl, $C_6$-$C_{24}$ alkaryl, $C_6$-$C_{24}$ aralkyl, etc.), thiocarbamoyl (—(CS)—NH$_2$), mono-($C_1$-$C_{24}$ alkyl)-substituted thiocarbamoyl (—(CS)—NH($C_1$-$C_{24}$ alkyl)), di-($C_1$-$C_{24}$ alkyl)-substituted thiocarbamoyl (—(CS)—N($C_1$-$C_{24}$ alkyl)$_2$), carbamido (—NH—(CO)—NH$_2$), cyano (—C≡N), cyanato (—O—C≡N), amino (—NH$_2$), mono-($C_1$-$C_{24}$ alkyl)-substituted amino (—NH($C_1$-$C_{24}$ alkyl)), di-($C_1$-$C_{24}$ alkyl)-substituted amino (—N($C_1$-$C_{24}$ alkyl)$_2$), mono-($C_1$-$C_{24}$ aryl)-substituted amino (—NH($C_5$-$C_{24}$ aryl)), di-($C_1$-$C_{24}$ aryl)-substituted amino (—N($C_1$-$C_{24}$ aryl)$_2$), —N—($C_1$-$C_{24}$ alkyl)($C_5$-$C_{24}$ aryl), $C_1$-$C_{24}$ alkylamido (—NH—(CO)—($C_1$-$C_{24}$ alkyl)), $C_5$-$C_{24}$ arylamido (—NH—(CO)—$C_5$-$C_{24}$ aryl), nitro (—NO$_2$), nitroso (—NO), nitrate (—NO$_3$), sulfo (—SO$_2$—OH), $C_1$-$C_6$ alkyl, $C_2$-$C_6$ alkenyl, $C_2$-$C_6$ alkynyl, $C_5$-$C_{10}$ aryl, $C_6$-$C_{16}$ alkaryl, and $C_6$-$C_{16}$ aralkyl.

In one embodiment, the invention provides, an olefin metathesis catalyst represented by the structure of Formula (I), wherein:

M is a Ru;
q is 0;
$X^3$ is Cl;
$X^4$ is Cl;
$L^4$ and $L^5$ are independently diaminocarbene ligands selected from:

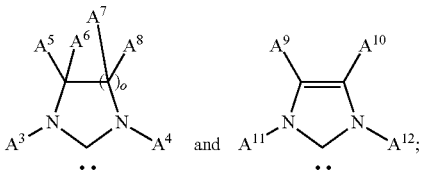

$A^3$, $A^4$, $A^{11}$ and $A^{12}$ are independently unsubstituted phenyl; phenyl substituted with at least one substituent selected from halo and $C_1$-$C_6$ alkyl; unsubstituted $C_5$-$C_{10}$ cycloalkyl; or $C_5$-$C_{10}$ cycloalkyl substituted with at least one substituent selected from halo and $C_1$-$C_6$ alkyl;

$A^5$, $A^6$, $A^7$, $A^8$, $A^9$ and $A^{10}$ are independently hydrogen, $C_1$-$C_6$ alkyl or $C_5$-$C_{10}$ aryl;

o is 1;

$A^1$ is hydrogen; and $A^2$ is $C_1$-$C_6$ alkyl substituted with at least one substituent selected from: halo, —OH, —O—($C_1$-$C_6$ alkyl), —O—($C_5$-$C_{10}$ aryl), —($C_6$-$C_{16}$ aralkyl)-O—, ($C_6$-$C_{16}$ alkylaryl)-O—, —CO—($C_1$-$C_6$ alkyl), —CO—($C_5$-$C_{10}$ aryl), —O—CO—($C_1$-$C_6$ alkyl), —O—CO—($C_5$-$C_{10}$ aryl), —CO—O—($C_1$-$C_6$ alkyl), —CO—O—($C_5$-$C_{10}$ aryl), —COOH, —CO—NH$_2$, CO—NH($C_1$-$C_6$ alkyl), —CO—N($C_1$-$C_6$ alkyl)$_2$, —S—($C_1$-$C_6$ alkyl), —(CS)—NH$_2$, —(CS)—NH($C_1$-$C_6$ alkyl), —(CS)—N($C_1$-$C_6$ alkyl)$_2$, —NH—(CO)—NH$_2$, —C≡N, —O—C≡N, —NH$_2$, —NH($C_1$-$C_6$ alkyl), —N($C_1$-$C_6$ alkyl)$_2$, —NH($C_5$-$C_{10}$ aryl), —N($C_5$-$C_{10}$ aryl)$_2$, —N—($C_1$-$C_6$ alkyl)($C_5$-$C_{10}$ aryl), —NH—(CO)—($C_1$-$C_6$ alkyl), —NH—(CO)—($C_5$-$C_{10}$ aryl), —NO$_2$, —NO, —NO$_3$, —SO$_2$—OH, $C_1$-$C_6$ alkyl, $C_2$-$C_6$ alkenyl, $C_2$-$C_6$ alkynyl, $C_5$-$C_{10}$ aryl, $C_6$-$C_{16}$ alkaryl, and $C_6$-$C_{16}$ aralkyl;

$C_2$-$C_6$ alkenyl substituted with at least one substituent selected from: halo, —OH, —O—($C_1$-$C_6$ alkyl), —O—($C_5$-$C_{10}$ aryl), —($C_6$-$C_{16}$ aralkyl)-O—, ($C_6$-$C_{16}$ alkylaryl)-O—, —CO—($C_1$-$C_6$ alkyl), —CO—($C_5$-$C_{10}$ aryl), —O—CO—($C_1$-$C_6$ alkyl), —O—CO—($C_5$-$C_{10}$ aryl), —CO—O—($C_1$-$C_6$ alkyl), —CO—O—($C_5$-$C_{10}$ aryl), —COOH, —CO—NH$_2$, CO—NH($C_1$-$C_6$ alkyl), —CO—N($C_1$-$C_6$ alkyl)$_2$, —S—($C_1$-$C_6$ alkyl), —(CS)—NH$_2$, —(CS)—NH($C_1$-$C_6$ alkyl), —(CS)—N($C_1$-$C_6$ alkyl)$_2$, —NH—(CO)—NH$_2$, —C≡N, —O—C≡N, —NH$_2$, —NH($C_1$-$C_6$ alkyl), —N($C_1$-$C_6$ alkyl)$_2$, —NH($C_5$-$C_{10}$ aryl), —N($C_5$-$C_{10}$ aryl)$_2$, —N—($C_1$-$C_6$ alkyl)($C_5$-$C_{10}$ aryl), —NH—(CO)—($C_1$-$C_6$ alkyl), —NH—(CO)—($C_5$-$C_{10}$ aryl), —NO$_2$, —NO, —NO$_3$, —SO$_2$—OH, $C_1$-$C_6$ alkyl, $C_2$-$C_6$ alkenyl, $C_2$-$C_6$ alkynyl, $C_5$-$C_{10}$ aryl, $C_6$-$C_{16}$ alkaryl, and $C_6$-$C_{16}$ aralkyl; or $C_5$-$C_{10}$ aryl substituted with at least one substituent selected from: halo, —OH, —O—($C_1$-$C_6$ alkyl), —O—($C_5$-$C_{10}$ aryl), —($C_6$-$C_{16}$ aralkyl)-O—, ($C_6$-$C_{16}$ alkylaryl)-O—, —CO—($C_1$-$C_6$ alkyl), —CO—($C_5$-$C_{10}$ aryl), —O—CO—($C_1$-$C_6$ alkyl), —O—CO—($C_5$-$C_{10}$ aryl), —CO—O—($C_1$-$C_6$ alkyl), —CO—O—($C_5$-$C_{10}$ aryl), —COOH, —CO—NH$_2$, CO—NH($C_1$-$C_6$ alkyl), —CO—N($C_1$-$C_6$ alkyl)$_2$, —S—($C_1$-$C_6$ alkyl), —(CS)—NH$_2$, —(CS)—NH($C_1$-$C_6$ alkyl), —(CS)—N($C_1$-$C_6$ alkyl)$_2$, —NH—(CO)—NH$_2$, —C≡N, —O—C≡N, —NH$_2$, —NH($C_1$-$C_6$ alkyl), —N($C_1$-$C_6$ alkyl)$_2$, —NH($C_5$-$C_{10}$ aryl), —N($C_5$-$C_{10}$ aryl)$_2$, —N—($C_1$-$C_6$ alkyl)($C_5$-$C_{10}$ aryl), —NH—(CO)—($C_1$-$C_6$ alkyl), —NH—(CO)—($C_5$-$C_{10}$ aryl), —NO$_2$, —NO, —NO$_3$, —SO$_2$—OH, $C_1$-$C_6$ alkyl, $C_2$-$C_6$ alkenyl, $C_2$-$C_6$ alkynyl, $C_5$-$C_{10}$ aryl, $C_6$-$C_{16}$ alkaryl, and $C_6$-$C_{16}$ aralkyl.

In one embodiment, the invention provides, an olefin metathesis catalyst represented by the structure of Formula (I), wherein:

M is a Ru;
q is 0;
$X^3$ is Cl;
$X^4$ is Cl;
$L^4$ and $L^5$ are independently:

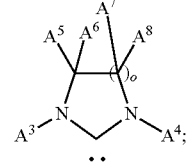

$A^3$ and $A^4$ are independently unsubstituted phenyl; phenyl substituted with at least one substituent selected from halo and $C_1$-$C_6$ alkyl; unsubstituted $C_5$-$C_{10}$ cycloalkyl; or $C_5$-$C_{10}$ cycloalkyl substituted with at least one substituent selected from halo and $C_1$-$C_6$ alkyl;

$A^5$, $A^6$, $A^7$, $A^8$, $A^9$ and $A^{10}$ are independently hydrogen, $C_1$-$C_6$ alkyl or $C_5$-$C_{10}$ aryl;

$A^5$, $A^6$, $A^7$ and $A^8$ are independently hydrogen, $C_1$-$C_6$ alkyl or $C_5$-$C_{10}$ aryl;

o is 1;

$A^1$ is hydrogen; and $A^2$ is phenyl, $C_1$-$C_3$ alkyl, or $C_2$-$C_4$ alkenyl, and $A^2$ is substituted with at least one substituent selected from: $C_1$-$C_6$ alkoxy (—O-alkyl), $C_2$-$C_{24}$ alkylcarbonyloxy (—O—CO-alkyl) and $C_1$-$C_6$ alkyl groups.

In one embodiment, the invention provides, an olefin metathesis catalyst represented by the structure of Formula (I), wherein:

M is a Ru;
q is 0;
$X^3$ is Cl;
$X^4$ is Cl;

$L^4$ and $L^5$ are independently:

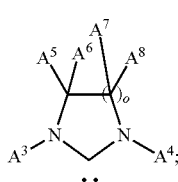

$A^5$, $A^6$, $A^7$, $A^8$ are independently hydrogen;
$A^1$ is hydrogen;
$A^2$ is phenyl, vinyl, or $C_1$-$C_3$ alkyl and each $A^2$ is substituted with at least one substituent selected from: $C_1$-$C_6$ alkoxy (—O-alkyl), $C_2$-$C_{24}$ alkylcarbonyloxy (—O—CO-alkyl) and $C_1$-$C_6$ alkyl groups;
o is 1; and
$A^3$ and $A^4$ are each phenyl independently substituted with three moieties selected from $C_1$-$C_6$ alkyl.

In one embodiment, the invention provides, an olefin metathesis catalyst represented by the structure of Formula (I), wherein:
M is a Ru;
q is 0;
$X^3$ is Cl;
$X^4$ is Cl;
$L^4$ and L are independently:

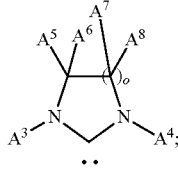

$A^5$, $A^6$, $A^7$, $A^8$ are independently hydrogen,
$A^1$ is hydrogen;
$A^2$ is —$CH_2$—OC(O)$CH_3$, —CH=C($CH_3$)$_2$ or 2-phenyl iso-propoxy;
o is 1; and
$A^3$ and $A^4$ are each mesityl.

In one embodiment, the invention provides, an olefin metathesis catalyst represented by the structure of Formula (I), selected from:

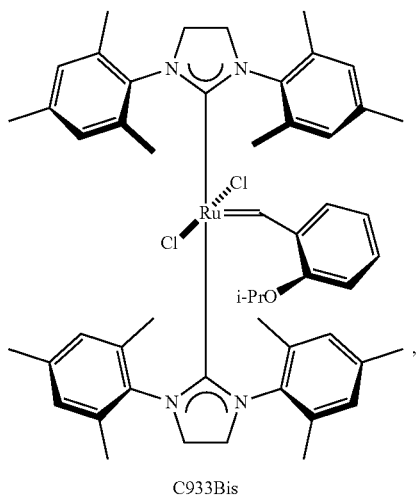

C933Bis

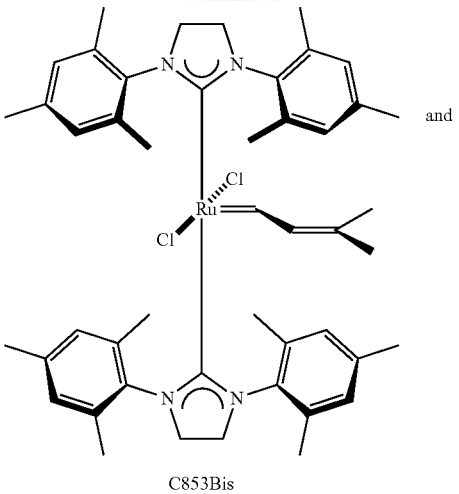

C853Bis and

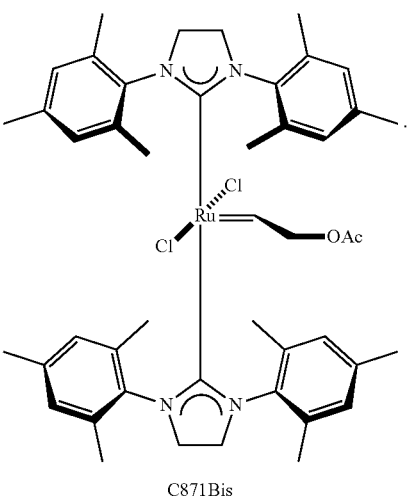

C871Bis

The present invention concerns also processes for preparing the olefin metathesis catalysts represented by Formula (I). The olefin metathesis catalysts according to the invention can be prepared analogously to conventional methods as understood by the person of skill in the art of synthetic organic chemistry. For example, synthetic Scheme 1 set forth below, illustrates how the olefin metathesis catalysts according to the invention can be made.

Scheme 1

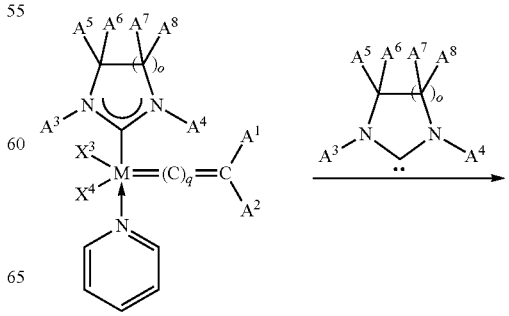

-continued

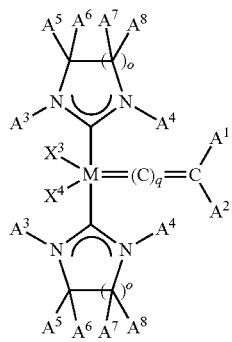

In one embodiment, the reaction in synthetic Scheme 1, takes place under $N_2$ at room temperature or at high temperature in dichloromethane or toluene. Once the reaction is completed, the mixture is cooled to room temperature, the solvent is removed under high vacuum, and the residue is purified by chromatography and then recrystallized to afford the olefin metathesis catalyst.

At this stage, those skilled in the art will appreciate that additional compounds that fall under the scope of the invention may be prepared by performing various common chemical reactions. Details of certain specific chemical transformations are provided in the examples.

The olefin metathesis catalysts of the invention, may be utilized in olefin metathesis reactions according to techniques known in the art. For example, the olefin metathesis catalysts are typically added to a resin composition as a solid, a solution, or as a suspension. When the olefin metathesis catalysts are added to a resin composition as a suspension, the olefin metathesis catalysts are suspended in a dispersing carrier such as mineral oil, paraffin oil, soybean oil, tri-isopropylbenzene, or any hydrophobic liquid which has a sufficiently high viscosity so as to permit effective dispersion of the catalyst(s), and which is sufficiently inert and which has a sufficiently high boiling point so that is does not act as a low-boiling impurity in the olefin metathesis reaction. It will be appreciated that the amount of catalyst that is used (i.e., the "catalyst loading") in the reaction is dependent upon a variety of factors such as the identity of the reactants and the reaction conditions that are employed. It is therefore understood that catalyst loading may be optimally and independently chosen for each reaction. In general, however, the catalyst will be present in an amount that ranges from a low of about 0.1 ppm, 1 ppm, or 5 ppm, to a high of about 10 ppm, 15 ppm, 25 ppm, 50 ppm, 100 ppm, 200 ppm, 500 ppm, or 1000 ppm relative to the amount of an olefinic substrate (e.g., cyclic olefins).

The catalyst will generally be present in an amount that ranges from a low of about 0.00001 mol %, 0.0001 mol %, or 0.0005 mol %, to a high of about 0.001 mol %, 0.0015 mol %, 0.0025 mol %, 0.005 mol %, 0.01 mol %, 0.02 mol %, 0.05 mol %, or 0.1 mol % relative to the olefinic substrate (e.g., cyclic olefins).

When expressed as the molar ratio of monomer to catalyst, the catalyst (the "monomer to catalyst ratio"), loading will generally be present in an amount that ranges from a low of about 10,000,000:1, 1,000,000:1, 500,000:1 or 200,00:1, to a high of about 100,000:1 60,000:1, 50,000:1, 45,000;1, 40,000:1, 30,000:1, 20,000:1, 10,000:1, 5,000:1, or 1,000:1.

Metathesis Conditions

Any set of conditions suitable for performing the cross-metathesis reaction may be utilized in the present invention. The cross-metathesis reactions utilized herein, may be homo-metathesis reactions or hetero-metathesis reactions. The term "homo-metathesis" as used herein, refers to a cross-metathesis reaction between a first olefin reactant and a second olefin reactant, wherein the first olefin reactant and the second olefin reactant are the same. The product formed from a "homo-metathesis" reaction comprises an internal C=C double bond, wherein the C=C double bond comprises one carbon atom from the C=C double bond of the first olefin reactant and one carbon atom from the C=C double bond of the second olefin reactant. As known by one of skill in the art, the internal C=C double bond of the homo-metathesis product may have either a Z-configuration or and E-configuration or a cis-configuration or a trans-configuration. Those of ordinary skill in the art would understand the meaning of terms "cis-configuration" or "trans-configuration" or "Z-configuration" or "E-configuration" as used within the context of the invention. Preferably, as provided herein, the internal C=C double bond of the homo-metathesis product is in the Z-configuration.

The term "hetero-metathesis" as used herein, refers to a cross-metathesis reaction between a first olefin reactant and a second olefin reactant, wherein the first olefin reactant and the second olefin reactant are different. The product formed from a "hetero-metathesis" reaction comprises an internal C=C double bond, wherein the C=C double bond comprises one carbon atom from the C=C double bond of the first olefin reactant and one carbon atom from the C=C double bond of the second olefin reactant. As known by one of skill in the art, the internal C=C double bond of the hetero-metathesis product may have either a Z-configuration or and E-configuration or a cis-configuration or a trans-configuration. Those of ordinary skill in the art would understand the meaning of terms "cis-configuration" or "trans-configuration" or "Z-configuration" or "E-configuration" as used within the context of the invention. Preferably, as provided herein, the internal C=C double bond of the hetero-metathesis product is in the Z-configuration.

According to the invention, the first olefin reactant and the second olefin reactant selected for the cross-metathesis reaction can both be reactant terminal olefins, both can be reactant internal olefins, or one can be a reactant terminal olefin and the other can be a reactant internal olefin, where the term reactant terminal olefin and reactant internal olefin are described herein. Moreover, those of ordinary skill in the art would understand the meaning of the terms terminal olefin and internal olefin. In one example, if two reactant terminal olefins are subjected to metathesis conditions, the two reactant terminal olefins may be the same or different. In another example, if two reactant internal olefins are subjected to metathesis conditions, the two reactant internal olefins may be the same or different. In another example, if a reactant terminal olefin and a reactant internal olefin are subjected to metathesis conditions, the reactant terminal olefin may be a single reactant terminal olefin or mixture of different reactant terminal olefins, and the reactant internal olefin may be a single reactant internal olefin or a mixture of different reactant internal olefins.

The cross-metathesis reaction may be performed in the presence or absence of solvent. Any solvent that does not interfere with the metathesis catalyst or the cross-metathesis reaction and/or the dihydroxylation reaction may be used in the present invention. An example of solvents for use in the cross-metathesis reaction include, without limitation, tetrahydrofuran (TF), dioxane, diethyl ether ($Et_2O$), dichloromethane ($CH_2Cl_2$), ethyl acetate (EtOAc) or mixtures thereof.

The cross-metathesis reaction may be optionally performed under inert gas purge (e.g., argon purge, nitrogen purge, helium purge), under vacuum (vacuum conditions), for example static vacuum (static vacuum conditions) or dynamic vacuum (dynamic vacuum conditions). In one embodiment, the cross-metathesis reaction is performed under vacuum. In one embodiment, the cross-metathesis reaction is performed under static vacuum. Preferably, the cross-metathesis reaction is performed under static vacuum. In another example, any inhibitory bi-products (e.g., ethylene, or any bi-product that inhibits dihydroxylation) may be removed from a cross-metathesis mixture during a cross-metathesis reaction or subsequent to performing a cross-metathesis reaction using any known technique including without limitation inert gas purge (e.g., argon purge, nitrogen purge, helium purge), under vacuum (vacuum conditions), for example static vacuum (static vacuum conditions) or dynamic vacuum (dynamic vacuum conditions).

Olefin Reactant Comprising a Reactant Terminal Olefin

In one example an olefin reactant comprising a reactant terminal olefin may be represented by the structure of Formula (III):

Formula (III)

wherein:

$D^1$ and $D^2$ are independently selected from nil, $CH_2$, O, or S; and $E^1$ and $E^2$ are independently selected from hydrogen, hydrocarbyl (e.g., $C_1$-$C_{20}$ alkyl, $C_5$-$C_{20}$ aryl, $C_5$-$C_{30}$ aralkyl, or $C_5$-$C_{30}$ alkaryl), substituted hydrocarbyl (e.g., substituted $C_1$-$C_{20}$ alkyl, $C_5$-$C_{20}$ aryl, $C_5$-$C_{30}$ aralkyl, or $C_5$-$C_{30}$ alkaryl), heteroatom-containing hydrocarbyl (e.g., $C_1$-$C_{20}$ heteroalkyl, $C_5$-$C_{20}$ heteroaryl, heteroatom-containing $C_5$-$C_{30}$ aralkyl, or heteroatom-containing $C_5$-$C_{30}$ alkaryl), and substituted heteroatom-containing hydrocarbyl (e.g., substituted $C_1$-$C_{20}$ heteroalkyl, $C_5$-$C_2o$ heteroaryl, heteroatom-containing $C_5$-$C_{30}$ aralkyl, or heteroatom-containing $C_5$-$C_{30}$ alkaryl) and, if substituted hydrocarbyl or substituted heteroatom-containing hydrocarbyl, wherein the substituents may be functional groups ("Fn") such as halo, hydroxyl, sulfhydryl, $C_1$-$C_{24}$ alkoxy, $C_5$-$C_{24}$ aryloxy, $C_6$-$C_{24}$ aralkyloxy, $C_6$-$C_{24}$ alkaryloxy, acyl (including $C_2$-$C_{24}$ alkylcarbonyl (—CO-alkyl) and $C_6$-$C_{24}$ arylcarbonyl (—CO-aryl)), acyloxy (—O-acyl, including $C_2$-$C_{24}$ alkylcarbonyloxy (—O—CO-alkyl) and $C_6$-$C_{24}$ arylcarbonyloxy (—O—CO-aryl)), $C_2$-$C_{24}$ alkoxycarbonyl (—(CO)—O-alkyl), $C_6$-$C_{24}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{24}$ arylcarbonato (—O—(CO)—O-aryl), carboxy (—COOH), carboxylato (—COO—), carbamoyl (—(CO)—$NH_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)$_2$), mono-($C_1$-$C_{24}$ haloalkyl)-substituted carbamoyl (—(CO)—NH($C_1$-$C_{24}$ haloalkyl)), di-($C_1$-$C_{24}$ haloalkyl)-substituted carbamoyl (—(CO)—N($C_1$-$C_{24}$ haloalkyl)$_2$), mono-($C_5$-$C_{24}$ aryl)-substituted carbamoyl (—(CO)—NH-aryl), di-($C_5$-$C_{24}$ aryl)-substituted carbamoyl (—(CO)—N($C_5$-$C_{24}$ aryl)$_2$), di-N—($C_1$-$C_{24}$ alkyl), N—($C_5$-$C_{24}$ aryl)-substituted carbamoyl (—(CO)—N($C_1$-$C_{24}$ alkyl) ($C_5$-$C_{24}$ aryl), thiocarbamoyl (—(CS)—$NH_2$), mono-($C_1$-$C_{24}$ alkyl)-substituted thiocarbamoyl (—(CS)—NH($C_1$-$C_{24}$ alkyl)), di-($C_1$-$C_{24}$ alkyl)-substituted thiocarbamoyl (—(CS)—N($C_1$-$C_{24}$ alkyl)$_2$), mono-($C_5$-$C_{24}$ aryl)-substituted thiocarbamoyl (—(CS)—NH-aryl), di-($C_5$-$C_{24}$ aryl)-substituted thiocarbamoyl (—(CS)—N($C_5$-$C_{24}$ aryl)$_2$), di-N—($C_1$-$C_{24}$ alkyl), N—($C_5$-$C_{24}$ aryl)-substituted thiocarbamoyl (—(CS)—N($C_1$-$C_{24}$ alkyl)($C_5$-$C_{24}$ aryl), carbamido (—NH—(CO)—$NH_2$), cyano (—C≡N), cyanato (—O—C≡N), thiocyanato (—S—C≡N), isocyanate (—N=C=O), thioisocyanate (—N=C=S), formyl (—(CO)—H), thioformyl (—(CS)—H), amino (—$NH_2$), mono-($C_1$-$C_{24}$ alkyl)-substituted amino (—NH($C_1$-$C_{24}$ alkyl), di-($C_1$-$C_{24}$ alkyl)-substituted amino (—N($C_1$-$C_{24}$ alkyl)$_2$), mono-($C_5$-$C_{24}$ aryl)-substituted amino (—NH($C_5$-$C_{24}$ aryl), di-($C_5$-$C_{24}$ aryl)-substituted amino (—N($C_5$-$C_{24}$ aryl)$_2$), $C_2$-$C_{24}$ alkylamido (—NH—(CO)-alkyl), $C_6$-$C_{24}$ arylamido (—NH—(CO)-aryl), imino (—CR=NH where R includes without limitation hydrogen, $C_1$-$C_{24}$ alkyl, $C_5$-$C_{24}$ aryl, $C_6$-$C_{24}$ alkaryl, $C_6$-$C_{24}$ aralkyl, etc.), $C_2$-$C_{20}$ alkylimino (—CR=N(alkyl), where R includes without limitation hydrogen, $C_1$-$C_{24}$ alkyl, $C_5$-$C_{24}$ aryl, $C_6$-$C_{24}$ alkaryl, $C_6$-$C_{24}$ aralkyl, etc.), arylimino (—CR=N(aryl), where R includes without limitation hydrogen, $C_1$-$C_2o$ alkyl, $C_5$-$C_{24}$ aryl, $C_6$-$C_{24}$ alkaryl, $C_6$-$C_{24}$ aralkyl, etc.), nitro (—$NO_2$), nitroso (—NO), sulfo (—$SO_2$—OH), sulfonato (—$SO_2$—O—), $C_1$-$C_{24}$ alkylsulfanyl (—S-alkyl; also termed "alkylthio"), $C_5$-$C_{24}$ arylsulfanyl (—S-aryl; also termed "arylthio"), $C_1$-$C_{24}$ alkylsulfinyl (—(SO)-alkyl), $C_5$-$C_{24}$ arylsulfinyl (—(SO)-aryl), $C_1$-$C_{24}$ alkylsulfonyl (—$SO_2$-alkyl), $C_1$-$C_{24}$ monoalkylaminosulfonyl (—$SO_2$—N(H) alkyl), $C_1$-$C_{24}$ dialkylaminosulfonyl (—$SO_2$—N(alkyl)$_2$), $C_5$-$C_{24}$ arylsulfonyl (—$SO_2$-aryl), boryl (—$BH_2$), borono (—B(OH)$_2$), boronato (—B(OR)$_2$ where R is alkyl or aryl), phosphono (—P(O)(OH)$_2$), phosphonato (—P(O)(O$^-$)$_2$), phosphinato (—P(O)(O$^-$)), phospho (—$PO_2$), and phosphino (—$PH_2$); and the hydrocarbyl moieties $C_1$-$C_{24}$ alkyl (preferably $C_1$-$C_{12}$ alkyl, more preferably $C_1$-$C_6$ alkyl), $C_5$-$C_{24}$ aryl (preferably $C_5$-$C_{14}$ aryl), $C_6$-$C_{24}$ alkaryl (preferably $C_6$-$C_{16}$ alkaryl), and $C_6$-$C_{24}$ aralkyl (preferably $C_6$-$C_{16}$ aralkyl); and where if $E^1$ and $E^2$ are the same, then Di and $D^2$ must be different, and if Di and $D^2$ are the same then $E^1$ and $E^2$ must be different.

Moreover, in one embodiment, for an olefin reactant comprising a reactant terminal olefin represented by the structure of Formula (III), the functional groups may be selected from electron withdrawing groups. Examples of electron withdrawing groups of various embodiments may include, but are not limited to, aldehyde (—COH), ketone (—COR), acyl (—COR), carbonyl (—CO), carboxylic acid (—COOH), ester (—COOR), ester (—OCOR), sulfonamide (—$NRSO_2Ar$), carbamate (—$NCO_2R$), epoxide (e.g., epoxybutadiene), halides (—Cl, —F, —Br, —I), fluoromethyl (—$CF_n$), fluoroaryl (e.g., —$C_6F_5$, p-$CF_3C_6H_4$), cyano (—CN), sulfoxide (—SOR), sulfonyl (—$SO_2R$), sulfonic acid (—$SO_3H$), phthalamide, 1, 2° and 3° ammonium (—$NR_3^+$), or nitro (—$NO_2$), wherein n is 1, 2, or 3, and R is a hydrogen, methyl, substituted $C_2$-$C_6$ alkyl, unsubstituted $C_2$-$C_6$ alkyl, substituted aryl, or unsubstituted aryl. Examples of electron withdrawing groups of various embodiments include ester (—OCOR), sulfonamide (—$NRSO_2Ar$), carbamate (—$NCO_2R$), sulfonyl (—$SO_2R$), fluoromethyl (—$CF_n$), fluroaryl (e.g., —$C_6F_5$, p-$CF_3C_6H_4$), epoxide (e.g., epoxybutadiene), or cyano (—CN), wherein n is 1, 2, or 3, and R is a hydrogen, methyl, substituted $C_2$-$C_6$ alkyl, unsubstituted $C_2$-$C_6$ alkyl, substituted aryl, or unsubstituted aryl. Examples of electron withdrawing groups of various embodiments include ester (—COOR), ketone (—COR), aldehyde (—COH), halides (—Cl, —F, —Br, —I), carboxylic acid (—COOH), sulfonic acid (—SO$_3$H), 1, 2° and 3° ammonium (—NR$_3^+$), nitro (—NO$_2$), or phthalamide.

Another example an olefin reactant comprising a reactant terminal olefin may be represented by the structure of Formula (IV):

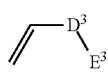

Formula (IV)

wherein:

$D^3$ is selected from nil, CH$_2$, O, or S; and $E^3$ is selected from hydrogen, hydrocarbyl (e.g., $C_1$-$C_{20}$ alkyl, $C_5$-$C_2$ aryl, $C_5$-$C_{30}$ aralkyl, or $C_5$-$C_{30}$ alkaryl), substituted hydrocarbyl (e.g., substituted $C_1$-$C_2$ alkyl, $C_5$-$C_2$ aryl, $C_5$-$C_{30}$ aralkyl, or $C_5$-$C_{30}$ alkaryl), heteroatom-containing hydrocarbyl (e.g., $C_1$-$C_{20}$ heteroalkyl, $C_5$-$C_{20}$ heteroaryl, heteroatom-containing $C_5$-$C_{30}$ aralkyl, or heteroatom-containing $C_5$-$C_{30}$ alkaryl), and substituted heteroatom-containing hydrocarbyl (e.g., substituted $C_1$-$C_{20}$ heteroalkyl, $C_5$-$C_{20}$ heteroaryl, heteroatom-containing $C_5$-$C_{30}$ aralkyl, or heteroatom-containing $C_5$-$C_{30}$ alkaryl) and, if substituted hydrocarbyl or substituted heteroatom-containing hydrocarbyl, wherein the substituents may be functional groups ("Fn") such as halo, hydroxyl, sulfhydryl, $C_1$-$C_{24}$ alkoxy, $C_5$-$C_{24}$ aryloxy, $C_6$-$C_{24}$ aralkyloxy, $C_6$-$C_{24}$ alkaryloxy, acyl (including $C_2$-$C_{24}$ alkylcarbonyl (—CO—alkyl) and $C_6$-$C_{24}$ arylcarbonyl (—CO-aryl)), acyloxy (—O-acyl, including $C_2$-$C_{24}$ alkylcarbonyloxy (—O—CO-alkyl) and $C_6$-$C_{24}$ arylcarbonyloxy (—O—CO-aryl)), $C_2$-$C_{24}$ alkoxycarbonyl (—(CO)—O— alkyl), $C_6$-$C_{24}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{24}$ arylcarbonato (—O—(CO)—O-aryl), carboxy (—COOH), carboxylato (—COO—), carbamoyl (—(CO)—NH$_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)$_2$), mono-($C_1$-$C_{24}$ haloalkyl)-substituted carbamoyl (—(CO)—NH($C_1$-$C_{24}$ haloalkyl)), di-($C_1$-$C_{24}$ haloalkyl)-substituted carbamoyl (—(CO)—N($C_1$-$C_{24}$ haloalkyl)$_2$), mono-($C_5$-$C_{24}$ aryl)-substituted carbamoyl (—(CO)—NH-aryl), di-($C_5$-$C_{24}$ aryl)-substituted carbamoyl (—(CO)—N($C_5$-$C_{24}$ aryl)$_2$), di-N—($C_1$-$C_{24}$ alkyl), N—($C_5$-$C_{24}$ aryl)-substituted carbamoyl (—(CO)—N($C_1$-$C_{24}$ alkyl)($C_5$-$C_{24}$ aryl), thiocarbamoyl (—(CS)—NH$_2$), mono-($C_1$-$C_{24}$ alkyl)-substituted thiocarbamoyl (—(CS)—NH($C_1$-$C_{24}$ alkyl)), di-($C_1$-$C_{24}$ alkyl)-substituted thiocarbamoyl (—(CS)—N($C_1$-$C_{24}$ alkyl)$_2$), mono-($C_5$-$C_{24}$ aryl)-substituted thiocarbamoyl (—(CS)—NH-aryl), di-($C_5$-$C_{24}$ aryl)-substituted thiocarbamoyl (—(CS)—N($C_5$-$C_{24}$ aryl)$_2$), di-N—($C_1$-$C_{24}$ alkyl), N—($C_5$-$C_{24}$ aryl)-substituted thiocarbamoyl (—(CS)—N($C_1$-$C_{24}$ alkyl)($C_5$-$C_{24}$ aryl), carbamido (—NH—(CO)—NH$_2$), cyano (—C≡N), cyanato (—O—C≡N), thiocyanato (—S—C≡N), isocyanate (—N=C=O), thioisocyanate (—N=C=S), formyl (—(CO)—H), thioformyl (—(CS)—H), amino (—NH$_2$), mono-($C_1$-$C_{24}$ alkyl)-substituted amino (—NH($C_1$-$C_{24}$ alkyl), di-($C_1$-$C_{24}$ alkyl)-substituted amino (—N($C_1$-$C_{24}$ alkyl)$_2$), mono-($C_5$-$C_{24}$ aryl)-substituted amino (—NH($C_5$-$C_{24}$ aryl), di-($C_5$-$C_{24}$ aryl)-substituted amino (—N($C_5$-$C_{24}$ aryl)$_2$), $C_2$-$C_{24}$ alkylamido (—NH—(CO)-alkyl), $C_6$-$C_{24}$ arylamido (—NH—(CO)-aryl), imino (—CR=NH where R includes without limitation hydrogen, $C_1$-$C_{24}$ alkyl, $C_5$-$C_{24}$ aryl, $C_6$-$C_{24}$ alkaryl, $C_6$-$C_{24}$ aralkyl, etc.), $C_2$-$C_{20}$ alkylimino (—CR=N (alkyl), where R includes without limitation hydrogen, $C_1$-$C_{24}$ alkyl, $C_5$-$C_{24}$ aryl, $C_6$-$C_{24}$ alkaryl, $C_6$-$C_{24}$ aralkyl, etc.), arylimino (—CR=N(aryl), where R includes without limitation hydrogen, $C_1$-$C_{20}$ alkyl, $C_5$-$C_{24}$ aryl, $C_6$-$C_{24}$ alkaryl, $C_6$-$C_{24}$ aralkyl, etc.), nitro (—NO$_2$), nitroso (—NO), sulfo (—SO$_2$—OH), sulfonato (—SO$_2$—O—), $C_1$-$C_{24}$ alkylsulfanyl (—S-alkyl; also termed "alkylthio"), $C_5$-$C_{24}$ arylsulfanyl (—S-aryl; also termed "arylthio"), $C_1$-$C_{24}$ alkylsulfinyl (—(SO)-alkyl), $C_5$-$C_{24}$ arylsulfinyl (—(SO)-aryl), $C_1$-$C_{24}$ alkylsulfonyl (—SO$_2$-alkyl), $C_1$-$C_{24}$ monoalkylaminosulfonyl (—SO$_2$—N(H) alkyl), $C_1$-$C_{24}$ dialkylaminosulfonyl (—SO$_2$—N(alkyl)$_2$), $C_5$-$C_{24}$ arylsulfonyl (—SO$_2$-aryl), boryl (—BH$_2$), borono (—B(OH)$_2$), boronato (—B(OR)$_2$ where R is alkyl or aryl), phosphono (—P(O)(OH)$_2$), phosphonato (—P(O)(O$^-$)$_2$), phosphinato (—P(O)(O$^-$)), phospho (—PO$_2$), and phosphino (—PH$_2$); and the hydrocarbyl moieties $C_1$-$C_{24}$ alkyl (preferably $C_1$-$C_{12}$ alkyl, more preferably $C_1$-$C_6$ alkyl), $C_5$-$C_{24}$ aryl (preferably $C_5$-$C_{14}$ aryl), $C_6$-$C_{24}$ alkaryl (preferably $C_6$-$C_{16}$ alkaryl), and $C_6$-$C_{24}$ aralkyl (preferably $C_6$-$C_{16}$ aralkyl); and where if $E^3$ is hydrogen then $D^3$ cannot be nil.

Moreover, in one embodiment, for an olefin reactant comprising a reactant terminal olefin represented by the structure of Formula (IV), the functional groups may be selected from electron withdrawing groups. Examples of electron withdrawing groups of various embodiments may include, but are not limited to, aldehyde (—COH), ketone (—COR), acyl (—COR), carbonyl (—CO), carboxylic acid (—COOH), ester (—COOR), ester (—OCOR), sulfonamide (—NRSO$_2$Ar), carbamate (—NC$_2$R), epoxide (e.g., epoxybutadiene), halides (—Cl, —F, —Br, —I), fluoromethyl (—CF$_n$), fluroaryl (e.g., —C$_6$F$_5$, p-CF$_3$C$_6$H$_4$), cyano (—CN), sulfoxide (—SOR), sulfonyl (—S$_2$R), sulfonic acid (—SO$_3$H), phthalamide, 1, 2° and 3° ammonium (—NR$_3^+$), or nitro (—NO$_2$), wherein n is 1, 2, or 3, and R is a hydrogen, methyl, substituted $C_2$-$C_6$ alkyl, unsubstituted $C_2$-$C_6$ alkyl, substituted aryl, or unsubstituted aryl. Examples of electron withdrawing groups of various embodiments include ester (—OCOR), sulfonamide (—NRSO$_2$Ar), carbamate (—NCO$_2$R), sulfonyl (—SO$_2$R), fluoromethyl (—CF$_n$), fluroaryl (e.g., —C$_6$F$_5$, p-CF$_3$C$_6$H$_4$), epoxide (e.g., epoxybutadiene), or cyano (—CN), wherein n is 1, 2, or 3, and R is a hydrogen, methyl, substituted $C_2$-$C_6$ alkyl, unsubstituted $C_2$-$C_6$ alkyl, substituted aryl, or unsubstituted aryl. Examples of electron withdrawing groups of various embodiments include ester (—COOR), ketone (—COR), aldehyde (—COH), halides (—Cl, —F, —Br, —I), carboxylic acid (—COOH), sulfonic acid (—SO$_3$H), 1, 2° and 3° ammonium (—NR$_3^+$), nitro (—NO$_2$), or phthalamide.

In another embodiment of the invention, an olefin reactant comprising a reactant terminal olefin may be represented by the structure of Formula (IV), wherein: $D^3$ is CH$_2$ or substituted heteroatom-containing hydrocarbyl; and $E^3$ is a functional group ("Fn") such as: acyloxy (—O-acyl, including $C_2$-$C_{24}$ alkylcarbonyloxy (—O—CO-alkyl) and $C_6$-$C_{24}$ arylcarbonyloxy (—O—CO-aryl)), $C_2$-$C_{24}$ alkylcarbonato (—O—(CO)—O-alkyl), $C_6$-$C_{24}$ arylcarbonato (—O—(CO)—O-aryl), carbamido (—NH—(CO)—NH$_2$), —NH—(CO)—NHR, —NH—(CO)—NR$^2$, $C_2$-$C_{24}$ alkylamido (—NH—(CO)-alkyl), $C_6$-$C_{24}$ arylamido (—NH—(CO)-aryl), nitro (—NO$_2$), nitroso (—NO), sulfo (—SO$_2$—OH), sulfonato (—SO₂—O—), C₁-C₂₄ alkylsulfinyl (—(SO)-alkyl), C₅-C₂₄ arylsulfinyl (—(SO)-aryl), C₁-C₂₄ alkylsulfonyl (—SO₂-alkyl), C₁-C₂₄ monoalkylaminosulfonyl (—SO₂—N(H) alkyl), C₁-C₂₄ dialkylaminosulfonyl (—SO₂—N(alkyl)₂), C₅-C₂₄ arylsulfonyl (—SO₂-aryl), phosphono (—P(O)(OH)₂), phosphonato (—P(O)(O⁻)₂), phosphinato (—P(O)(O⁻)), phospho (—PO₂), —O—P(O)(OR)₂, (wherein R is C₁-C₂₄ alkyl, (C₅-C₂₄ aryl), C₆-C₂₄ alkaryl, C₆-C₂₄ aralkyl), or an electron withdrawing group such as: ester (—OCOR), sulfonamide (—NRSO₂Ar), carbamate (—NCO₂R), sulfoxide (—SOR), sulfonyl (—SO₂R), sulfonic acid (—SO₃H), phthalamide, or nitro (—NO₂), wherein R is a hydrogen, methyl, substituted C₂-C₆ alkyl, unsubstituted C₂-C₆ alkyl, substituted aryl, or unsubstituted aryl.

In another embodiment of the invention, an olefin reactant comprising a reactant terminal olefin may be represented by the structure of Formula (IV), wherein: $D^3$ is $CH_2$; and $E^3$ is an electron withdrawing group such as: ester (—OCOR), sulfonamide (—NRSO₂Ar), carbamate (—NCO₂R), sulfonyl (—SO₂R), sulfonic acid (—SO₃H), phthalamide, or nitro (—NO₂), wherein R is a hydrogen, methyl, substituted C₂-C₆ alkyl, unsubstituted C₂-C₆ alkyl, substituted aryl, or unsubstituted aryl.

One or more olefin reactants comprising a reactant terminal olefin may be used with the invention described herein, wherein the one or more olefin reactants comprising a reactant terminal olefin may be the same or different.

Olefin Reactant Comprising a Reactant Internal Olefin

One or more olefin reactants comprising a reactant internal olefin may be used with the invention described herein, wherein the one or more olefin reactants comprising a reactant internal olefin may be the same or different.

In the one or more olefin reactants comprising a reactant internal olefin, the reactant internal olefin may be in the Z- or E-configuration. In one embodiment, in the one or more olefin reactants comprising a reactant internal olefin, the reactant internal olefin is in the Z-configuration. In one embodiment, in the one or more olefin reactants comprising a reactant internal olefin, the reactant internal olefin is in the E-configuration.

In one example an olefin reactant comprising a reactant internal olefin may be represented by the structure of Formula (V):

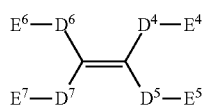

Formula (V)

wherein:

$D^4$, $D^5$, $D^6$, and $D^7$ are independently selected from nil, $CH_2$, O, or S; and $E^4$, $E^5$, $E^6$, and $E^7$ are independently selected from hydrogen, hydrocarbyl (e.g., C₁-C₂₀ alkyl, C₅-C₂₀ aryl, C₅-C₃₀ aralkyl, or C₅-C₃₀ alkaryl), substituted hydrocarbyl (e.g., substituted C₁-C₂₀ alkyl, C₅-C₂₀ aryl, C₅-C₃₀ aralkyl, or C₅-C₃₀ alkaryl), heteroatom-containing hydrocarbyl (e.g., C₁-C₂₀ heteroalkyl, C₅-C₂₀ heteroaryl, heteroatom-containing C₅-C₃₀ aralkyl, or heteroatom-containing C₅-C₃₀ alkaryl), and substituted heteroatom-containing hydrocarbyl (e.g., substituted C₁-C₂₀ heteroalkyl, C₅-C₂₀ heteroaryl, heteroatom-containing C₅-C₃₀ aralkyl, or heteroatom-containing C₅-C₃₀ alkaryl) and, if substituted hydrocarbyl or substituted heteroatom-containing hydrocarbyl, wherein the substituents may be functional groups ("Fn") such as halo, hydroxyl, sulfhydryl, C₁-C₂₄ alkoxy, C₅-C₂₄ aryloxy, C₆-C₂₄ aralkyloxy, C₆-C₂₄ alkaryloxy, acyl (including C₂-C₂₄ alkylcarbonyl (—CO-alkyl) and C₆-C₂₄ arylcarbonyl (—CO-aryl)), acyloxy (—O-acyl, including C₂-C₂₄ alkylcarbonyloxy (—O—CO-alkyl) and C₆-C₂₄ arylcarbonyloxy (—O—CO-aryl)), C₂-C₂₄ alkoxycarbonyl (—(CO)—O-alkyl), C₆-C₂₄ aryloxycarbonyl (—(CO)—O-aryl), halocarbonyl (—CO)—X where X is halo), C₂-C₂₄ alkylcarbonato (—O—(CO)—O-alkyl), C₆-C₂₄ arylcarbonato (—O—(CO)—O-aryl), carboxy (—COOH), carboxylato (—COO—), carbamoyl (—(CO)—NH₂), mono-(C₁-C₂₄ alkyl)-substituted carbamoyl (—(CO)—NH(C₁-C₂₄ alkyl)), di-(C₁-C₂₄ alkyl)-substituted carbamoyl (—(CO)—N(C₁-C₂₄ alkyl)₂), mono-(C₁-C₂₄ haloalkyl)-substituted carbamoyl (—(CO)—NH(C₁-C₂₄ haloalkyl)), di-(C₁-C₂₄ haloalkyl)-substituted carbamoyl (—(CO)—N(C₁-C₂₄ haloalkyl)₂), mono-(C₅-C₂₄ aryl)-substituted carbamoyl (—(CO)—NH-aryl), di-(C₅-C₂₄ aryl)-substituted carbamoyl (—(CO)—N(C₅-C₂₄ aryl)₂), di-N—(C₁-C₂₄ alkyl), N—(C₅-C₂₄ aryl)-substituted carbamoyl (—(CO)—N(C₁-C₂₄ alkyl) (C₅-C₂₄ aryl), thiocarbamoyl (—(CS)—NH₂), mono-(C₁-C₂₄ alkyl)-substituted thiocarbamoyl (—(CS)—NH(C₁-C₂₄ alkyl)), di-(C₁-C₂₄ alkyl)-substituted thiocarbamoyl (—(CS)—N(C₁-C₂₄ alkyl)₂), mono-(C₅-C₂₄ aryl)-substituted thiocarbamoyl (—(CS)—NH-aryl), di-(C₅-C₂₄ aryl)-substituted thiocarbamoyl (—(CS)—N(C₅-C₂₄ aryl)₂), di-N—(C₁-C₂₄ alkyl), N—(C₅-C₂₄ aryl)-substituted thiocarbamoyl (—(CS)—N(C₁-C₂₄ alkyl)(C₅-C₂₄ aryl), carbamido (—NH—(CO)—NH₂), cyano (—C≡N), cyanato (—O—C≡N), thiocyanato (—S—C≡N), isocyanate (—N=C=O), thioisocyanate (—N=C=S), formyl (—(CO)—H), thioformyl (—(CS)—H), amino (—NH₂), mono-(C₁-C₂₄ alkyl)-substituted amino (—NH(C₁-C₂₄ alkyl), di-(C₁-C₂₄ alkyl)-substituted amino (—N(C₁-C₂₄ alkyl)₂), mono-(C₅-C₂₄ aryl)-substituted amino (—NH(C₅-C₂₄ aryl), di-(C₅-C₂₄ aryl)-substituted amino (—N(C₅-C₂₄ aryl)₂), C₂-C₂₄ alkylamido (—NH—(CO)-alkyl), C₆-C₂₄ arylamido (—NH—(CO)-aryl), imino (—CR=NH where R includes without limitation hydrogen, C₁-C₂₄ alkyl, C₅-C₂₄ aryl, C₆-C₂₄ alkaryl, C₆-C₂₄ aralkyl, etc.), C₂-C₂₀ alkylimino (—CR=N (alkyl), where R includes without limitation hydrogen, C₁-C₂₄ alkyl, C₅-C₂₄ aryl, C₆-C₂₄ alkaryl, C₆-C₂₄ aralkyl, etc.), arylimino (—CR=N(aryl), where R includes without limitation hydrogen, C₁-C₂₀ alkyl, C₅-C₂₄ aryl, C₆-C₂₄ alkaryl, C₆-C₂₄ aralkyl, etc.), nitro (—NO₂), nitroso (—NO), sulfo (—SO₂—OH), sulfonato (—SO₂—O—), C₁-C₂₄ alkylsulfanyl (—S-alkyl; also termed "alkylthio"), C₅-C₂₄ arylsulfanyl (—S-aryl; also termed "arylthio"), C₁-C₂₄ alkylsulfinyl (—(SO)-alkyl), C₅-C₂₄ arylsulfinyl (—(SO)-aryl), C₁-C₂₄ alkylsulfonyl (—SO₂-alkyl), C₁-C₂₄ monoalkylaminosulfonyl (—SO₂—N(H) alkyl), C₁-C₂₄ dialkylaminosulfonyl (—SO₂—N(alkyl)₂), C₅-C₂₄ arylsulfonyl (—SO₂-aryl), boryl (—BH₂), borono (—B(OH)₂), boronato (—B(OR)₂ where R is alkyl or aryl), phosphono (—P(O)(OH)₂), phosphonato (—P(O)(O⁻)₂), phosphinato (—P(O)(O⁻)), phospho (—PO₂), and phosphino (—PH₂); and the hydrocarbyl moieties C₁-C₂₄ alkyl (preferably C—C₁₂ alkyl, more preferably C₁-C₆ alkyl), C₅-C₂₄ aryl (preferably C₅-C₁₄ aryl), C₆-C₂₄ alkaryl (preferably C₆-C₁₆ alkaryl), and C₆-C₂₄ aralkyl (preferably C₆-C₁₆ aralkyl); and where if $E^4$ and $E^5$ are the same, then $D^4$ and $D^5$ must be different, and if $D^4$ and $D^5$ are the same then $E^4$ and $E^5$ must be different, and where if $E^6$ and $E^7$ are the same, then $D^6$ and $D^7$ must be different, and if $D^6$ and $D^7$ are the same then $E^6$ and $E^7$ must be different.

Moreover, in one embodiment, for an olefin reactant comprising a reactant internal olefin represented by the structure of Formula (V), the functional groups may be selected from electron withdrawing groups. Examples of electron withdrawing groups of various embodiments may include, but are not limited to, aldehyde (—COH), ketone (—COR), acyl (—COR), carbonyl (—CO), carboxylic acid (—COOH), ester (—COOR), ester (—OCOR), sulfonamide (—NRSO$_2$Ar), carbamate (—NCO$_2$R), epoxide (e.g., epoxybutadiene), halides (—Cl, —F, —Br, —I), fluoromethyl (—CF$_n$), fluroaryl (e.g., —C$_6$F$_5$, p-CF$_3$C$_6$H$_4$), cyano (—CN), sulfoxide (—SOR), sulfonyl (—SO$_2$R), sulfonic acid (—SO$_3$H), phthalamide, 1, 2° and 3° ammonium (—NR$_3^+$), or nitro (—NO$_2$), wherein n is 1, 2, or 3, and R is a hydrogen, methyl, substituted C$_2$-C$_6$ alkyl, unsubstituted C$_2$-C$_6$ alkyl, substituted aryl, or unsubstituted aryl. Examples of electron withdrawing groups of various embodiments include ester (—OCOR), sulfonamide (—NRSO$_2$Ar), carbamate (—NCO$_2$R), sulfonyl (—SO$_2$R), fluoromethyl (—CF$_n$), fluroaryl (e.g., —C$_6$F$_5$, p-CF$_3$C$_6$H$_4$), epoxide (e.g., epoxybutadiene), or cyano (—CN), wherein n is 1, 2, or 3, and R is a hydrogen, methyl, substituted C$_2$-C$_6$ alkyl, unsubstituted C$_2$-C$_6$ alkyl, substituted aryl, or unsubstituted aryl. Examples of electron withdrawing groups of various embodiments include ester (—COOR), ketone (—COR), aldehyde (—COH), halides (—Cl, —F, —Br, —I), carboxylic acid (—COOH), sulfonic acid (—SO$_3$H), 1, 2° and 3° ammonium (—NR$_3^+$), nitro (—NO$_2$), or phthalamide.

In one example an olefin reactant comprising a reactant internal olefin may be represented by the structure of Formula (VI):

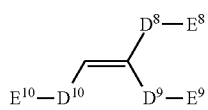

Formula (VI)

wherein:

$D^8$, $D^9$, and $D^{10}$ are independently selected from nil, CH$_2$, O, or S; and $E^8$, $E^9$, and $E^{10}$ are independently selected from hydrogen, hydrocarbyl (e.g., C$_1$-C$_{20}$ alkyl, C$_5$-C$_{20}$ aryl, C$_5$-C$_{30}$ aralkyl, or C$_5$-C$_{30}$ alkaryl), substituted hydrocarbyl (e.g., substituted C$_1$-C$_{20}$ alkyl, C$_5$-C$_{20}$ aryl, C$_5$-C$_{30}$ aralkyl, or C$_5$-C$_{30}$ alkaryl), heteroatom-containing hydrocarbyl (e.g., C$_1$-C$_{20}$ heteroalkyl, C$_5$-C$_{20}$ heteroaryl, heteroatom-containing C$_5$-C$_{30}$ aralkyl, or heteroatom-containing C$_5$-C$_{30}$ alkaryl), and substituted heteroatom-containing hydrocarbyl (e.g., substituted C$_1$-C$_{20}$ heteroalkyl, C$_5$-C$_{20}$ heteroaryl, heteroatom-containing C$_5$-C$_{30}$ aralkyl, or heteroatom-containing C$_5$-C$_{30}$ alkaryl) and, if substituted hydrocarbyl or substituted heteroatom-containing hydrocarbyl, wherein the substituents may be functional groups ("Fn") such as halo, hydroxyl, sulfhydryl, C$_1$-C$_{24}$ alkoxy, C$_5$-C$_{24}$ aryloxy, C$_6$-C$_{24}$ aralkyloxy, C$_6$-C$_{24}$ alkaryloxy, acyl (including C$_2$-C$_{24}$ alkylcarbonyl (—CO-alkyl) and C$_6$-C$_{24}$ arylcarbonyl (—CO-aryl)), acyloxy (—O-acyl, including C$_2$-C$_{24}$ alkylcarbonyloxy (—O—CO-alkyl) and C$_6$-C$_{24}$ arylcarbonyloxy (—O—CO-aryl)), C$_2$-C$_{24}$ alkoxycarbonyl (—(CO)—O-alkyl), C$_6$-C$_{24}$ aryloxycarbonyl (—(CO)—O-aryl), halocarbonyl (—CO)—X where X is halo), C$_2$-C$_{24}$ alkylcarbonato (—O—(CO)—O-alkyl), C$_6$-C$_{24}$ arylcarbonato (—O—(CO)—O-aryl), carboxy (—COOH), carboxylato (—COO—), carbamoyl (—(CO)—NH$_2$), mono-(C$_1$-C$_{24}$ alkyl)-substituted carbamoyl (—(CO)—NH(C$_1$-C$_{24}$ alkyl)), di-(C$_1$-C$_{24}$ alkyl)-substituted carbamoyl (—(CO)—N(C$_1$-C$_{24}$ alkyl)$_2$), mono-(C$_1$-C$_{24}$ haloalkyl)-substituted carbamoyl (—(CO)—NH(C$_1$-C$_{24}$ haloalkyl)), di-(C$_1$-C$_{24}$ haloalkyl)-substituted carbamoyl (—(CO)—N(C$_1$-C$_{24}$ haloalkyl)$_2$), mono-(C$_5$-C$_{24}$ aryl)-substituted carbamoyl (—(CO)—NH-aryl), di-(C$_5$-C$_{24}$ aryl)-substituted carbamoyl (—(CO)—N(C$_5$-C$_{24}$ aryl)$_2$), di-N—(C$_1$-C$_{24}$ alkyl), N—(C$_5$-C$_{24}$ aryl)-substituted carbamoyl (—(CO)—N(C$_1$-C$_{24}$ alkyl) (C$_5$-C$_{24}$ aryl), thiocarbamoyl (—(CS)—NH$_2$), mono-(C$_1$-C$_{24}$ alkyl)-substituted thiocarbamoyl (—(CS)—NH(C$_1$-C$_{24}$ alkyl)), di-(C$_1$-C$_{24}$ alkyl)-substituted thiocarbamoyl (—(CS)—N(C$_1$-C$_{24}$ alkyl)$_2$), mono-(C$_5$-C$_{24}$ aryl)-substituted thiocarbamoyl (—(CS)—NH-aryl), di-(C$_5$-C$_{24}$ aryl)-substituted thiocarbamoyl (—(CS)—N(C$_5$-C$_{24}$ aryl)$_2$), di-N—(C$_1$-C$_{24}$ alkyl), N—(C$_5$-C$_{24}$ aryl)-substituted thiocarbamoyl (—(CS)—N(C$_1$-C$_{24}$ alkyl)(C$_5$-C$_{24}$ aryl), carbamido (—NH—(CO)—NH$_2$), cyano (—C≡N), cyanato (—O—C≡N), thiocyanato (—S—C≡N), isocyanate (—N═C═O), thioisocyanate (—N═C═S), formyl (—(CO)—H), thioformyl (—(CS)—H), amino (—NH$_2$), mono-(C$_1$-C$_{24}$ alkyl)-substituted amino (—NH(C$_1$-C$_{24}$ alkyl), di-(C$_1$-C$_{24}$ alkyl)-substituted amino (—N(C$_1$-C$_{24}$ alkyl)$_2$), mono-(C$_5$-C$_{24}$ aryl)-substituted amino (—NH(C$_5$-C$_{24}$ aryl), di-(C$_5$-C$_{24}$ aryl)-substituted amino (—N(C$_5$-C$_{24}$ aryl)$_2$), C$_2$-C$_{24}$ alkylamido (—NH—(CO)-alkyl), C$_6$-C$_{24}$ arylamido (—NH—(CO)-aryl), imino (—CR═NH where R includes without limitation hydrogen, C$_1$-C$_{24}$ alkyl, C$_5$-C$_{24}$ aryl, C$_6$-C$_{24}$ alkaryl, C$_6$-C$_{24}$ aralkyl, etc.), C$_2$-C$_{20}$ alkylimino (—CR═N (alkyl), where R includes without limitation hydrogen, C$_1$-C$_{24}$ alkyl, C$_5$-C$_{24}$ aryl, C$_6$-C$_{24}$ alkaryl, C$_6$-C$_{24}$ aralkyl, etc.), arylimino (—CR═N(aryl), where R includes without limitation hydrogen, C$_1$-C$_{20}$ alkyl, C$_5$-C$_{24}$ aryl, C$_6$-C$_{24}$ alkaryl, C$_6$-C$_{24}$ aralkyl, etc.), nitro (—NO$_2$), nitroso (—NO), sulfo (—SO$_2$—OH), sulfonato (—SO$_2$—O—), C$_1$-C$_{24}$ alkylsulfanyl (—S-alkyl; also termed "alkylthio"), C$_5$-C$_{24}$ arylsulfanyl (—S-aryl; also termed "arylthio"), C$_1$-C$_{24}$ alkylsulfinyl (—(SO)-alkyl), C$_5$-C$_{24}$ arylsulfinyl (—(SO)-aryl), C$_1$-C$_{24}$ alkylsulfonyl (—SO$_2$-alkyl), C$_1$-C$_{24}$ monoalkylaminosulfonyl (—SO$_2$—N(H) alkyl), C$_1$-C$_{24}$ dialkylaminosulfonyl (—SO$_2$—N(alkyl)$_2$), C$_5$-C$_{24}$ arylsulfonyl (—SO$_2$-aryl), boryl (—BH$_2$), borono (—B (OH)$_2$), boronato (—B(OR)$_2$ where R is alkyl or aryl), phosphono (—P(O)(OH)$_2$), phosphonato (—P(O)(O$^-$)$_2$), phosphinato (—P(O)(O$^-$)), phospho (—PO$_2$), and phosphino (—PH$_2$); and the hydrocarbyl moieties C$_1$-C$_{24}$ alkyl (preferably C$_1$-C$_{12}$ alkyl, more preferably C$_1$-C$_6$ alkyl), C$_5$-C$_{24}$ aryl (preferably C$_5$-C$_{14}$ aryl), C$_6$-C$_{24}$ alkaryl (preferably C$_6$-C$_{16}$ alkaryl), and C$_6$-C$_{24}$ aralkyl (preferably C$_6$-C$_{16}$ aralkyl); and where if $E^8$ and $E^9$ are the same, then $D^8$ and $D^9$ must be different, and if $D^8$ and $D^9$ are the same then $E^8$ and $E^9$ must be different; and where if $E^{10}$ is hydrogen, then $D^{10}$ cannot be nil.

Moreover, in one embodiment, for an olefin reactant comprising a reactant internal olefin represented by the structure of Formula (VI), the functional groups may be selected from electron withdrawing groups. Examples of electron withdrawing groups of various embodiments may include, but are not limited to, aldehyde (—COH), ketone (—COR), acyl (—COR), carbonyl (—CO), carboxylic acid (—COOH), ester (—COOR), ester (—OCOR), sulfonamide (—NRSO$_2$Ar), carbamate (—NCO$_2$R), epoxide (e.g., epoxybutadiene), halides (—Cl, —F, —Br, —I), fluoromethyl (—CF$_n$), fluroaryl (e.g., —C$_6$F$_5$, p-CF$_3$C$_6$H$_4$), cyano (—CN), sulfoxide (—SOR), sulfonyl (—SO$_2$R), sulfonic acid (—SO$_3$H), phthalamide, 1, 2° and 3° ammonium (—NR$_3^+$), or nitro (—NO$_2$), wherein n is 1, 2, or 3, and R is a hydrogen, methyl, substituted C$_2$-C$_6$ alkyl, unsubstituted C$_2$-C$_6$ alkyl, substituted aryl, or unsubstituted aryl. Examples of electron withdrawing groups of various embodiments include ester (—OCOR), sulfonamide (—NRSO$_2$Ar), carbamate (—NCO$_2$R), sulfonyl (—SO$_2$R), fluoromethyl (—CF$_n$), fluroaryl (e.g., —C$_6$F$_5$, p-CF$_3$C$_6$H$_4$), epoxide (e.g., epoxybutadiene), or cyano (—CN), wherein n is 1, 2, or 3, and R is a hydrogen, methyl, substituted C$_2$-C$_6$ alkyl, unsubstituted C$_2$-C$_6$ alkyl, substituted aryl, or unsubstituted aryl. Examples of electron withdrawing groups of various embodiments include ester (—COOR), ketone (—COR), aldehyde (—COH), halides (—Cl, —F, —Br, —I), carboxylic acid (—COOH), sulfonic acid (—SO$_3$H), 1, 2° and 3° ammonium (—NR$_3^+$), nitro (—NO$_2$), or phthalamide.

In one example, an olefin reactant comprising a reactant internal olefin may be represented by the structure of Formula (VII):

Formula (VII)

wherein:

D$^{11}$ and D$^{12}$ are independently selected from nil, CH$_2$, O, or S; and

E$^{11}$ and E$^{12}$ are independently selected from hydrogen, hydrocarbyl (e.g., C$_1$-C$_{20}$ alkyl, C$_5$-C$_{20}$ aryl, C$_5$-C$_{30}$ aralkyl, or C$_5$-C$_{30}$ alkaryl), substituted hydrocarbyl (e.g., substituted C$_1$-C$_{20}$ alkyl, C$_5$-C$_{20}$ aryl, C$_5$-C$_{30}$ aralkyl, or C$_5$-C$_{30}$ alkaryl), heteroatom-containing hydrocarbyl (e.g., C$_1$-C$_{20}$ heteroalkyl, C$_5$-C$_{20}$ heteroaryl, heteroatom-containing C$_5$-C$_{30}$ aralkyl, or heteroatom-containing C$_5$-C$_{30}$ alkaryl), and substituted heteroatom-containing hydrocarbyl (e.g., substituted C$_1$-C$_{20}$ heteroalkyl, C$_5$-C$_{20}$ heteroaryl, heteroatom-containing C$_5$-C$_{30}$ aralkyl, or heteroatom-containing C$_5$-C$_{30}$ alkaryl) and, if substituted hydrocarbyl or substituted heteroatom-containing hydrocarbyl, wherein the substituents may be functional groups ("Fn") such as halo, hydroxyl, sulfhydryl, C$_1$-C$_{24}$ alkoxy, C$_5$-C$_{24}$ aryloxy, C$_6$-C$_{24}$ aralkyloxy, C$_6$-C$_{24}$ alkaryloxy, acyl (including C$_2$-C$_{24}$ alkylcarbonyl (—CO-alkyl) and C$_6$-C$_{24}$ arylcarbonyl (—CO-aryl)), acyloxy (—O-acyl, including C$_2$-C$_{24}$ alkylcarbonyloxy (—O—CO-alkyl) and C$_6$-C$_{24}$ arylcarbonyloxy (—O—CO-aryl)), C$_2$-C$_{24}$ alkoxycarbonyl (—(CO)—O-alkyl), C$_6$-C$_{24}$ aryloxycarbonyl (—(CO)—O-aryl), halocarbonyl (—CO)—X where X is halo), C$_2$-C$_{24}$ alkylcarbonato (—O—(CO)—O-alkyl), C$_6$-C$_{24}$ arylcarbonato (—O—(CO)—O-aryl), carboxy (—COOH), carboxylato (—COO—), carbamoyl (—(CO)—NH$_2$), mono-(C$_1$-C$_{24}$ alkyl)-substituted carbamoyl (—(CO)—NH(C$_1$-C$_{24}$ alkyl)), di-(C$_1$-C$_{24}$ alkyl)-substituted carbamoyl (—(CO)—N(C$_1$-C$_{24}$ alkyl)$_2$), mono-(C$_1$-C$_{24}$ haloalkyl)-substituted carbamoyl (—(CO)—NH(C$_1$-C$_{24}$ haloalkyl)), di-(C$_1$-C$_{24}$ haloalkyl)-substituted carbamoyl (—(CO)—N(C$_1$-C$_{24}$ haloalkyl)$_2$), mono-(C$_5$-C$_{24}$ aryl)-substituted carbamoyl (—(CO)—NH-aryl), di-(C$_5$-C$_{24}$ aryl)-substituted carbamoyl (—(CO)—N(C$_5$-C$_{24}$ aryl)$_2$), di-N—(C$_1$-C$_{24}$ alkyl), N—(C$_5$-C$_{24}$ aryl)-substituted carbamoyl (—(CO)—N(C—C$_{24}$ alkyl) (C$_5$-C$_{24}$ aryl), thiocarbamoyl (—(CS)—NH$_2$), mono-(C$_1$-C$_{24}$ alkyl)-substituted thiocarbamoyl (—(CS)—NH(C$_1$-C$_{24}$ alkyl)), di-(C$_1$-C$_{24}$ alkyl)-substituted thiocarbamoyl (—(CS)—N(C$_1$-C$_{24}$ alkyl)$_2$), mono-(C$_5$-C$_{24}$ aryl)-substituted thiocarbamoyl (—(CS)—NH-aryl), di-(C$_5$-C$_{24}$ aryl)-substituted thiocarbamoyl (—(CS)—N(C$_5$-C$_{24}$ aryl)$_2$), di-N—(C$_1$-C$_{24}$ alkyl), N—(C$_5$-C$_{24}$ aryl)-substituted thiocarbamoyl (—(CS)—N(C$_1$-C$_{24}$ alkyl)(C$_5$-C$_{24}$ aryl), carbamido (—NH—(CO)—NH$_2$), cyano (—C≡N), cyanato (—O—C≡N), thiocyanato (—S—C≡N), isocyanate (—N═C═O), thioisocyanate (—N═C═S), formyl (—(CO)—H), thioformyl (—(CS)—H), amino (—NH$_2$), mono-(C$_1$-C$_{24}$ alkyl)-substituted amino (—NH(C$_1$-C$_{24}$ alkyl), di-(C$_1$-C$_{24}$ alkyl)-substituted amino (—N(C$_1$-C$_{24}$ alkyl)$_2$), mono-(C$_5$-C$_{24}$ aryl)-substituted amino (—NH(C$_5$-C$_{24}$ aryl), di-(C$_5$-C$_{24}$ aryl)-substituted amino (—N(C$_5$-C$_{24}$ aryl)$_2$), C$_2$-C$_{24}$ alkylamido (—NH—(CO)-alkyl), C$_6$-C$_{24}$ arylamido (—NH—(CO)-aryl), imino (—CR═NH where R includes without limitation hydrogen, C$_1$-C$_{24}$ alkyl, C$_5$-C$_{24}$ aryl, C$_6$-C$_{24}$ alkaryl, C$_6$-C$_{24}$ aralkyl, etc.), C$_2$-C$_{20}$ alkylimino (—CR═N(alkyl), where R includes without limitation hydrogen, C$_1$-C$_{24}$ alkyl, C$_5$-C$_{24}$ aryl, C$_6$-C$_{24}$ alkaryl, C$_6$-C$_{24}$ aralkyl, etc.), arylimino (—CR═N(aryl), where R includes without limitation hydrogen, C$_1$-C$_{20}$ alkyl, C$_5$-C$_{24}$ aryl, C$_6$-C$_{24}$ alkaryl, C$_6$-C$_{24}$ aralkyl, etc.), nitro (—NO$_2$), nitroso (—NO), sulfo (—SO$_2$—OH), sulfonato (—SO$_2$—O—), C$_1$-C$_{24}$ alkylsulfanyl (—S-alkyl; also termed "alkylthio"), C$_5$-C$_{24}$ arylsulfanyl (—S-aryl; also termed "arylthio"), C$_1$-C$_{24}$ alkylsulfinyl (—(SO)-alkyl), C$_5$-C$_{24}$ arylsulfinyl (—(SO)-aryl), C$_1$-C$_{24}$ alkylsulfonyl (—SO$_2$-alkyl), C$_1$-C$_{24}$ monoalkylaminosulfonyl (—SO$_2$—N(H) alkyl), C$_1$-C$_{24}$ dialkylaminosulfonyl (—SO$_2$—N(alkyl)$_2$), C$_5$-C$_{24}$ arylsulfonyl (—SO$_2$-aryl), boryl (—BH$_2$), borono (—B(OH)$_2$), boronato (—B(OR)$_2$ where R is alkyl or aryl), phosphono (—P(O)(OH)$_2$), phosphonato (—P(O)(O$^-$)$_2$), phosphinato (—P(O)(O$^-$)), phospho (—PO$_2$), and phosphino (—PH$_2$); and the hydrocarbyl moieties C$_1$-C$_{24}$ alkyl (preferably C—C$_{12}$ alkyl, more preferably C$_1$-C$_6$ alkyl), C$_5$-C$_{24}$ aryl (preferably C$_5$-C$_{14}$ aryl), C$_6$-C$_{24}$ alkaryl (preferably C$_6$-C$_{16}$ alkaryl), and C$_6$-C$_{24}$ aralkyl (preferably C$_6$-C$_{16}$ aralkyl); and where if E$^{11}$ is hydrogen, then D$^{11}$ cannot be nil; and where if E$^{12}$ is hydrogen, then D$^{12}$ cannot be nil.

Moreover, in one embodiment, for an olefin reactant comprising a reactant internal olefin represented by the structure of Formula (VII), the functional groups may be selected from electron withdrawing groups. Examples of electron withdrawing groups of various embodiments may include, but are not limited to, aldehyde (—COH), ketone (—COR), acyl (—COR), carbonyl (—CO), carboxylic acid (—COOH), ester (—COOR), ester (—OCOR), sulfonamide (—NRSO$_2$Ar), carbamate (—NCO$_2$R), epoxide (e.g., epoxybutadiene), halides (—Cl, —F, —Br, —I), fluoromethyl (—CF$_n$), fluroaryl (e.g., —C$_6$F$_5$, p-CF$_3$C$_6$H$_4$), cyano (—CN), sulfoxide (—SOR), sulfonyl (—S$_2$R), sulfonic acid (—SO$_3$H), phthalamide, 1, 2° and 3° ammonium (—NR$_3^+$), or nitro (—NO$_2$), wherein n is 1, 2, or 3, and R is a hydrogen, methyl, substituted C$_2$-C$_6$ alkyl, unsubstituted C$_2$-C$_6$ alkyl, substituted aryl, or unsubstituted aryl. Examples of electron withdrawing groups of various embodiments include ester (—OCOR), sulfonamide (—NRSO$_2$Ar), carbamate (—NCO$_2$R), sulfonyl (—SO$_2$R), fluoromethyl (—CF$_n$), fluroaryl (e.g., —C$_6$F$_5$, p-CF$_3$C$_6$H$_4$), epoxide (e.g., epoxybutadiene), or cyano (—CN), wherein n is 1, 2, or 3, and R is a hydrogen, methyl, substituted C$_2$-C$_6$ alkyl, unsubstituted C$_2$-C$_6$ alkyl, substituted aryl, or unsubstituted aryl. Examples of electron withdrawing groups of various embodiments include ester (—COOR), ketone (—COR), aldehyde (—COH), halides (—Cl, —F, —Br, —I), carboxylic acid (—COOH), sulfonic acid (—SO$_3$H), 1, 2° and 3° ammonium (—NR$_3^+$), nitro (—NO$_2$), or phthalamide.

In another embodiment of the invention, an olefin reactant comprising a reactant terminal olefin may be represented by the structure of Formula (VII), wherein: $D^{11}$ and $D^{12}$ are CH$_2$; and $E^{11}$ and $E^{12}$ are independently functional groups ("Fn") such as: acyloxy (—O-acyl, including C$_2$-C$_{24}$ alkylcarbonyloxy (—O—CO-alkyl) and C$_6$-C$_{24}$ arylcarbonyloxy (—O—CO-aryl)), C$_2$-C$_{24}$ alkylcarbonato (—O—(CO)—O-alkyl), C$_6$-C$_{24}$ arylcarbonato (—O—(CO)—O-aryl), carbamido (—NH—(CO)—NH$_2$), —NH—(CO)—NHR, —NH—(CO)—NR$^2$, C$_2$-C$_{24}$ alkylamido (—NH—(CO)-alkyl), C$_6$-C$_{24}$ arylamido (—NH—(CO)-aryl), nitro (—NO$_2$), nitroso (—NO), sulfo (—SO$_2$—OH), sulfonato (—SO$_2$—O—), C$_1$-C$_{24}$ alkylsulfinyl (—(SO)-alkyl), C$_5$-C$_{24}$ arylsulfinyl (—(SO)-aryl), C$_1$-C$_{24}$ alkylsulfonyl (—SO$_2$-alkyl), C$_1$-C$_{24}$ monoalkylaminosulfonyl (—SO$_2$—N(H) alkyl), C$_1$-C$_{24}$ dialkylaminosulfonyl (—SO$_2$—N(alkyl)$_2$), C$_5$-C$_{24}$ arylsulfonyl (—SO$_2$-aryl), phosphono (—P(O)(OH)$_2$), phosphonato (—P(O)(O$^-$)$_2$), phosphinato (—P(O)(O$^-$)), phospho (—PO$_2$), —O—P(O)(OR)$_2$, (wherein R is C$_1$-C$_{24}$ alkyl, (C$_5$-C$_{24}$ aryl), C$_6$-C$_{24}$ alkaryl, C$_6$-C$_{24}$ aralkyl), or an electron withdrawing group such as: ester (—OCOR), sulfonamide (—NRSO$_2$Ar), carbamate (—NCO$_2$R), sulfoxide (—SOR), sulfonyl (—SO$_2$R), sulfonic acid (—SO$_3$H), phthalamide, or nitro (—NO$_2$), wherein: R is a hydrogen, methyl, substituted C$_2$-C$_6$ alkyl, unsubstituted C$_2$-C$_6$ alkyl, substituted aryl, or unsubstituted aryl.

In another embodiment of the invention, an olefin reactant comprising a reactant terminal olefin may be represented by the structure of Formula (VII), wherein: $D^{11}$ and $D^{12}$ are CH$_2$; and $E^{11}$ and $E^{12}$ are independently electron withdrawing groups such as: ester (—OCOR), sulfonamide (—NRSO$_2$Ar), carbamate (—NCO$_2$R), sulfonyl (—SO$_2$R), sulfonic acid (—SO$_3$H), phthalamide, or nitro (—NO$_2$), wherein: R is a hydrogen, methyl, substituted C$_2$-C$_6$ alkyl, unsubstituted C$_2$-C$_6$ alkyl, substituted aryl, or unsubstituted aryl.

In one example an olefin reactant comprising a reactant internal olefin may be represented by the structure of Formula (VIII):

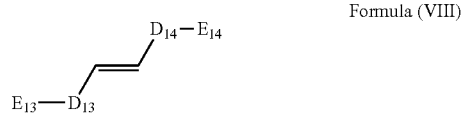

Formula (VIII)

wherein:

$D^{13}$ and $D^{14}$ are independently selected from nil, CH$_2$, O, or S; and $E^{13}$ and $E^{14}$ are independently selected from hydrogen, hydrocarbyl (e.g., C$_1$-C$_{20}$ alkyl, C$_5$-C$_{20}$ aryl, C$_5$-C$_{30}$ aralkyl, or C$_5$-C$_{30}$ alkaryl), substituted hydrocarbyl (e.g., substituted C$_1$-C$_{20}$ alkyl, C$_5$-C$_{20}$ aryl, C$_5$-C$_{30}$ aralkyl, or C$_5$-C$_{30}$ alkaryl), heteroatom-containing hydrocarbyl (e.g., C$_1$-C$_{20}$ heteroalkyl, C$_5$-C$_{20}$ heteroaryl, heteroatom-containing C$_5$-C$_{30}$ aralkyl, or heteroatom-containing C$_5$-C$_{30}$ alkaryl), and substituted heteroatom-containing hydrocarbyl (e.g., substituted C$_1$-C$_{20}$ heteroalkyl, C$_5$-C$_{20}$ heteroaryl, heteroatom-containing C$_5$-C$_{30}$ aralkyl, or heteroatom-containing C$_5$-C$_{30}$ alkaryl) and, if substituted hydrocarbyl or substituted heteroatom-containing hydrocarbyl, wherein the substituents may be functional groups ("Fn") such as halo, hydroxyl, sulfhydryl, C$_1$-C$_{24}$ alkoxy, C$_5$-C$_{24}$ aryloxy, C$_6$-C$_{24}$ aralkyloxy, C$_6$-C$_{24}$ alkaryloxy, acyl (including C$_2$-C$_{24}$ alkylcarbonyl (—CO-alkyl) and C$_6$-C$_{24}$ arylcarbonyl (—CO-aryl)), acyloxy (—O-acyl, including C$_2$-C$_{24}$ alkylcarbonyloxy (—O—CO-alkyl) and C$_6$-C$_{24}$ arylcarbonyloxy (—O—CO-aryl)), C$_2$-C$_{24}$ alkoxycarbonyl (—(CO)—O-alkyl), C$_6$-C$_{24}$ aryloxycarbonyl (—(CO)—O-aryl), halocarbonyl (—(CO)—X where X is halo), C$_2$-C$_{24}$ alkylcarbonato (—O—(CO)—O-alkyl), C$_6$-C$_{24}$ arylcarbonato (—O—(CO)—O-aryl), carboxy (—COOH), carboxylato (—COO—), carbamoyl (—(CO)—NH$_2$), mono-(C$_1$-C$_{24}$ alkyl)-substituted carbamoyl (—(CO)—NH(C$_1$-C$_{24}$ alkyl)), di-(C$_1$-C$_{24}$ alkyl)-substituted carbamoyl (—(CO)—N(C$_1$-C$_{24}$ alkyl)$_2$), mono-(C$_1$-C$_{24}$ haloalkyl)-substituted carbamoyl (—(CO)—NH(C$_1$-C$_{24}$ haloalkyl)), di-(C$_1$-C$_{24}$ haloalkyl)-substituted carbamoyl (—(CO)—N(C$_1$-C$_{24}$ haloalkyl)$_2$), mono-(C$_5$-C$_{24}$ aryl)-substituted carbamoyl (—(CO)—NH-aryl), di-(C$_5$-C$_{24}$ aryl)-substituted carbamoyl (—(CO)—N(C$_5$-C$_{24}$ aryl)$_2$), di-N—(C$_1$-C$_{24}$ alkyl), N—(C$_5$-C$_{24}$ aryl)-substituted carbamoyl (—(CO)—N(C$_1$-C$_{24}$ alkyl) (C$_5$-C$_{24}$ aryl), thiocarbamoyl (—(CS)—NH$_2$), mono-(C$_1$-C$_{24}$ alkyl)-substituted thiocarbamoyl (—(CS)—NH(C$_1$-C$_{24}$ alkyl)), di-(C$_1$-C$_{24}$ alkyl)-substituted thiocarbamoyl (—(CS)—N(C$_1$-C$_{24}$ alkyl)$_2$), mono-(C$_5$-C$_{24}$ aryl)-substituted thiocarbamoyl (—(CS)—NH-aryl), di-(C$_5$-C$_{24}$ aryl)-substituted thiocarbamoyl (—(CS)—N(C$_5$-C$_{24}$ aryl)$_2$), di-N—(C$_1$-C$_{24}$ alkyl), N—(C$_5$-C$_{24}$ aryl)-substituted thiocarbamoyl (—(CS)—N(C$_1$-C$_{24}$ alkyl)(C$_5$-C$_{24}$ aryl), carbamido (—NH—(CO)—NH$_2$), cyano (—C≡N), cyanato (—O—C≡N), thiocyanato (—S—C≡N), isocyanate (—N=C=O), thioisocyanate (—N=C=S), formyl (—(CO)—H), thioformyl (—(CS)—H), amino (—NH$_2$), mono-(C$_1$-C$_{24}$ alkyl)-substituted amino (—NH(C$_1$-C$_{24}$ alkyl), di-(C$_1$-C$_{24}$ alkyl)-substituted amino (—N(C$_1$-C$_{24}$ alkyl)$_2$), mono-(C$_5$-C$_{24}$ aryl)-substituted amino (—NH(C$_5$-C$_{24}$ aryl), di-(C$_5$-C$_{24}$ aryl)-substituted amino (—N(C$_5$-C$_{24}$ aryl)$_2$), C$_2$-C$_{24}$ alkylamido (—NH—(CO)-alkyl), C$_6$-C$_{24}$ arylamido (—NH—(CO)-aryl), imino (—CR=NH where R includes without limitation hydrogen, C$_1$-C$_{24}$ alkyl, C$_5$-C$_{24}$ aryl, C$_6$-C$_{24}$ alkaryl, C$_6$-C$_{24}$ aralkyl, etc.), C$_2$-C$_{20}$ alkylimino (—CR=N(alkyl), where R includes without limitation hydrogen, C$_1$-C$_{24}$ alkyl, C$_5$-C$_{24}$ aryl, C$_6$-C$_{24}$ alkaryl, C$_6$-C$_{24}$ aralkyl, etc.), arylimino (—CR=N(aryl), where R includes without limitation hydrogen, C$_1$-C$_{20}$ alkyl, C$_5$-C$_{24}$ aryl, C$_6$-C$_{24}$ alkaryl, C$_6$-C$_{24}$ aralkyl, etc.), nitro (—NO$_2$), nitroso (—NO), sulfo (—SO$_2$—OH), sulfonato (—SO$_2$—O—), C$_1$-C$_{24}$ alkylsulfanyl (—S-alkyl; also termed "alkylthio"), C$_5$-C$_{24}$ arylsulfanyl (—S-aryl; also termed "arylthio"), C$_1$-C$_{24}$ alkylsulfinyl (—(SO)-alkyl), C$_5$-C$_{24}$ arylsulfinyl (—(SO)-aryl), C$_1$-C$_{24}$ alkylsulfonyl (—SO$_2$-alkyl), C$_1$-C$_{24}$ monoalkylaminosulfonyl (—SO$_2$—N(H) alkyl), C$_1$-C$_{24}$ dialkylaminosulfonyl (—SO$_2$—N(alkyl)$_2$), C$_5$-C$_{24}$ arylsulfonyl (—SO$_2$-aryl), boryl (—BH$_2$), borono (—B(OH)$_2$), boronato (—B(OR)$_2$ where R is alkyl or aryl), phosphono (—P(O)(OH)$_2$), phosphonato (—P(O)(O$^-$)$_2$), phosphinato (—P(O)(O$^-$)), phospho (—PO$_2$), and phosphino (—PH$_2$); and the hydrocarbyl moieties C$_1$-C$_{24}$ alkyl (preferably C$_1$-C$_{12}$ alkyl, more preferably C$_1$-C$_6$ alkyl), C$_5$-C$_{24}$ aryl (preferably C$_5$-C$_{14}$ aryl), C$_6$-C$_{24}$ alkaryl (preferably C$_6$-C$_{16}$ alkaryl), and C$_6$-C$_{24}$ aralkyl (preferably C$_6$-C$_{16}$ aralkyl); and where if $E^{13}$ is hydrogen, then $D^{13}$ cannot be nil; and where if $E^{14}$ is hydrogen, then $D^{14}$ cannot be nil.

Moreover, in one embodiment, for an olefin reactant comprising a reactant internal olefin represented by the structure of Formula (VIII), the functional groups may be selected from electron withdrawing groups. Examples of electron withdrawing groups of various embodiments may include, but are not limited to, aldehyde (—COH), ketone (—COR), acyl (—COR), carbonyl (—CO), carboxylic acid (—COOH), ester (—COOR), ester (—OCOR), sulfonamide (—NRS$_2$Ar), carbamate (—NCO$_2$R), epoxide (e.g., epoxybutadiene), halides (—Cl, —F, —Br, —I), fluoromethyl (—CF$_n$), fluroaryl (e.g., —C$_6$F$_5$, p-CF$_3$C$_6$H$_4$), cyano (—CN), sulfoxide (—SOR), sulfonyl (—S$_2$R), sulfonic acid (—SO$_3$H), phthalamide, 1°, 2° and 3° ammonium (—NR$_3^+$), or nitro (—NO$_2$), wherein n is 1, 2, or 3, and R is a hydrogen, methyl, substituted C$_2$-C$_6$ alkyl, unsubstituted C$_2$-C$_6$ alkyl, substituted aryl, or unsubstituted aryl. Examples of electron withdrawing groups of various embodiments include ester (—OCOR), sulfonamide (—NRSO$_2$Ar), carbamate (—NCO$_2$R), sulfonyl (—SO$_2$R), fluoromethyl (—CF$_n$), fluroaryl (e.g., —C$_6$F$_5$, p-CF$_3$C$_6$H$_4$), epoxide (e.g., epoxybutadiene), or cyano (—CN), wherein n is 1, 2, or 3, and R is a hydrogen, methyl, substituted C$_2$-C$_6$ alkyl, unsubstituted C$_2$-C$_6$ alkyl, substituted aryl, or unsubstituted aryl. Examples of electron withdrawing groups of various embodiments include ester (—COOR), ketone (—COR), aldehyde (—COH), halides (—Cl, —F, —Br, —I), carboxylic acid (—COOH), sulfonic acid (—SO$_3$H), 1°, 2° and 3° ammonium (—NR$_3^+$), nitro (—NO$_2$), or phthalamide.

Cross-Metathesis Product Comprising a Product Internal Olefin

One or more cross-metathesis products comprising a product internal olefin, wherein the product internal olefin is in the Z-configuration may be used with the invention described herein, wherein the one or more cross-metathesis products comprising a product internal olefin may be the same or different.

In one example an at least one cross-metathesis product comprising a product internal olefin, wherein the product internal olefin is in the Z-configuration may be represented by the structure of Formula (IX):

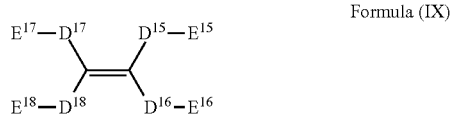

Formula (IX)

wherein:
D$^{15}$, D$^{16}$, D$^{17}$, and D$^{18}$ are independently selected from nil, CH$_2$, O, or S; and
E$^{15}$, E$^{16}$, E$^{17}$, and E$^{18}$ are independently selected from hydrogen, hydrocarbyl (e.g., C$_1$-C$_{20}$ alkyl, C$_5$-C$_{20}$ aryl, C$_5$-C$_{30}$ aralkyl, or C$_5$-C$_{30}$ alkaryl), substituted hydrocarbyl (e.g., substituted C$_1$-C$_{20}$ alkyl, C$_5$-C$_{20}$ aryl, C$_5$-C$_{30}$ aralkyl, or C$_5$-C$_{30}$ alkaryl), heteroatom-containing hydrocarbyl (e.g., C$_1$-C$_{20}$ heteroalkyl, C$_5$-C$_{20}$ heteroaryl, heteroatom-containing C$_5$-C$_{30}$ aralkyl, or heteroatom-containing C$_5$-C$_{30}$ alkaryl), and substituted heteroatom-containing hydrocarbyl (e.g., substituted C$_1$-C$_{20}$ heteroalkyl, C$_5$-C$_{20}$ heteroaryl, heteroatom-containing C$_5$-C$_{30}$ aralkyl, or heteroatom-containing C$_5$-C$_{30}$ alkaryl) and, if substituted hydrocarbyl or substituted heteroatom-containing hydrocarbyl, wherein the substituents may be functional groups ("Fn") such as halo, hydroxyl, sulfhydryl, C$_1$-C$_{24}$ alkoxy, C$_5$-C$_{24}$ aryloxy, C$_6$-C$_{24}$ aralkyloxy, C$_6$-C$_{24}$ alkaryloxy, acyl (including C$_2$-C$_{24}$ alkylcarbonyl (—CO-alkyl) and C$_6$-C$_{24}$ arylcarbonyl (—CO-aryl)), acyloxy (—O-acyl, including C$_2$-C$_{24}$ alkylcarbonyloxy (—O—CO-alkyl) and C$_6$-C$_{24}$ arylcarbonyloxy (—O—CO-aryl)), C$_2$-C$_{24}$ alkoxycarbonyl (—(CO)—O-alkyl), C$_6$-C$_{24}$ aryloxycarbonyl (—(CO)—O-aryl), halocarbonyl (—CO)—X where X is halo), C$_2$-C$_{24}$ alkylcarbonato (—O—(CO)—O-alkyl), C$_6$-C$_{24}$ arylcarbonato (—O—(CO)—O-aryl), carboxy (—COOH), carboxylato (—COO—), carbamoyl (—(CO)—NH$_2$), mono-(C$_1$-C$_{24}$ alkyl)-substituted carbamoyl (—(CO)—NH(C$_1$-C$_{24}$ alkyl)), di-(C$_1$-C$_{24}$ alkyl)-substituted carbamoyl (—(CO)—N(C$_1$-C$_{24}$ alkyl)$_2$), mono-(C$_1$-C$_{24}$ haloalkyl)-substituted carbamoyl (—(CO)—NH(C$_1$-C$_{24}$ haloalkyl)), di-(C$_1$-C$_{24}$ haloalkyl)-substituted carbamoyl (—(CO)—N(C$_1$-C$_{24}$ haloalkyl)$_2$), mono-(C$_5$-C$_{24}$ aryl)-substituted carbamoyl (—(CO)—NH-aryl), di-(C$_5$-C$_{24}$ aryl)-substituted carbamoyl (—(CO)—N(C$_5$-C$_{24}$ aryl)$_2$), di-N—(C$_1$-C$_{24}$ alkyl), N—(C$_5$-C$_{24}$ aryl)-substituted carbamoyl (—(CO)—N(C$_1$-C$_{24}$ alkyl) (C$_5$-C$_{24}$ aryl), thiocarbamoyl (—(CS)—NH$_2$), mono-(C$_1$-C$_{24}$ alkyl)-substituted thiocarbamoyl (—(CS)—NH(C$_1$-C$_{24}$ alkyl)), di-(C$_1$-C$_{24}$ alkyl)-substituted thiocarbamoyl (—(CS)—N(C$_1$-C$_{24}$ alkyl)$_2$), mono-(C$_5$-C$_{24}$ aryl)-substituted thiocarbamoyl (—(CS)—NH-aryl), di-(C$_5$-C$_{24}$ aryl)-substituted thiocarbamoyl (—(CS)—N(C$_5$-C$_{24}$ aryl)$_2$), di-N—(C$_1$-C$_{24}$ alkyl), N—(C$_5$-C$_{24}$ aryl)-substituted thiocarbamoyl (—(CS)—N(C$_1$-C$_{24}$ alkyl)(C$_5$-C$_{24}$ aryl), carbamido (—NH—(CO)—NH$_2$), cyano (—C≡N), cyanato (—O—C≡N), thiocyanato (—S—C≡N), isocyanate (—N=C=O), thioisocyanate (—N=C=S), formyl (—(CO)—H), thioformyl (—(CS)—H), amino (—NH$_2$), mono-(C$_1$-C$_{24}$ alkyl)-substituted amino (—NH(C$_1$-C$_{24}$ alkyl), di-(C$_1$-C$_{24}$ alkyl)-substituted amino (—N(C$_1$-C$_{24}$ alkyl)$_2$), mono-(C$_5$-C$_{24}$ aryl)-substituted amino (—NH(C$_5$-C$_{24}$ aryl), di-(C$_5$-C$_{24}$ aryl)-substituted amino (—N(C$_5$-C$_{24}$ aryl)$_2$), C$_2$-C$_{24}$ alkylamido (—NH—(CO)-alkyl), C$_6$-C$_{24}$ arylamido (—NH—(CO)-aryl), imino (—CR=NH where R includes without limitation hydrogen, C$_1$-C$_{24}$ alkyl, C$_5$-C$_{24}$ aryl, C$_6$-C$_{24}$ alkaryl, C$_6$-C$_{24}$ aralkyl, etc.), C$_2$-C$_{20}$ alkylimino (—CR=N (alkyl), where R includes without limitation hydrogen, C$_1$-C$_{24}$ alkyl, C$_5$-C$_{24}$ aryl, C$_6$-C$_{24}$ alkaryl, C$_6$-C$_{24}$ aralkyl, etc.), arylimino (—CR=N(aryl), where R includes without limitation hydrogen, C$_1$-C$_{20}$ alkyl, C$_5$-C$_{24}$ aryl, C$_6$-C$_{24}$ alkaryl, C$_6$-C$_{24}$ aralkyl, etc.), nitro (—NO$_2$), nitroso (—NO), sulfo (—SO$_2$—OH), sulfonato (—SO$_2$—O—), C$_1$-C$_{24}$ alkylsulfanyl (—S-alkyl; also termed "alkylthio"), C$_5$-C$_{24}$ arylsulfanyl (—S-aryl; also termed "arylthio"), C$_1$-C$_{24}$ alkylsulfinyl (—(SO)-alkyl), C$_5$-C$_{24}$ arylsulfinyl (—(SO)-aryl), C$_1$-C$_{24}$ alkylsulfonyl (—SO$_2$-alkyl), C$_1$-C$_{24}$ monoalkylaminosulfonyl (—SO$_2$—N(H) alkyl), C$_1$-C$_{24}$ dialkylaminosulfonyl (—SO$_2$—N(alkyl)$_2$), C$_5$-C$_{24}$ arylsulfonyl (—SO$_2$-aryl), boryl (—BH$_2$), borono (—B (OH)$_2$), boronato (—B(OR)$_2$ where R is alkyl or aryl), phosphono (—P(O)(OH)$_2$), phosphonato (—P(O)(O$^-$)$_2$), phosphinato (—P(O)(O$^-$)), phospho (—PO$_2$), and phosphino (—PH$_2$); and the hydrocarbyl moieties C$_1$-C$_{24}$ alkyl (preferably C$_1$-C$_{12}$ alkyl, more preferably C$_1$-C$_6$ alkyl), C$_5$-C$_{24}$ aryl (preferably C$_5$-C$_{14}$ aryl), C$_6$-C$_{24}$ alkaryl (preferably C$_6$-C$_{16}$ alkaryl), and C$_6$-C$_{24}$ aralkyl (preferably C$_6$-C$_{16}$ aralkyl); and
where if E$^{15}$ and E$^{16}$ are the same, then D$^{15}$ and D$^{16}$ must be different, and if D$^{15}$ and D$^{16}$ are the same then E$^{15}$ and E$^{16}$ must be different, and where if E$^{17}$ and E$^{18}$ are the same, then D$^{17}$ and D$^{18}$ must be different, and if D$^{17}$ and D$^{18}$ are the same then E$^{17}$ and E$^{18}$ must be different.

Moreover, in one embodiment, for at least one cross-metathesis product comprising a product internal olefin represented by the structure of Formula (IX), the functional groups may be selected from electron withdrawing groups. Examples of electron withdrawing groups of various embodiments may include, but are not limited to, aldehyde (—COH), ketone (—COR), acyl (—COR), carbonyl (—CO), carboxylic acid (—COOH), ester (—COOR), ester (—OCOR), sulfonamide (—NRSO$_2$Ar), carbamate (—NCO$_2$R), epoxide (e.g., epoxybutadiene), halides (—Cl, —F, —Br, —I), fluoromethyl (—CF$_n$), fluroaryl (e.g., —C$_6$F$_5$, p-CF$_3$C$_6$H$_4$), cyano (—CN), sulfoxide (—SOR), sulfonyl (—SO$_2$R), sulfonic acid (—SO$_3$H), phthalamide, 1, 2° and 3° ammonium (—NR$_3^+$), or nitro (—NO$_2$), wherein n is 1, 2, or 3, and R is a hydrogen, methyl, substituted C$_2$-C$_6$ alkyl, unsubstituted C$_2$-C$_6$ alkyl, substituted aryl, or unsubstituted aryl. Examples of electron withdrawing groups of various embodiments include ester (—OCOR), sulfonamide (—NRSO$_2$Ar), carbamate (—NCO$_2$R), sulfonyl (—SO$_2$R), fluoromethyl (—CF$_n$), fluroaryl (e.g., —C$_6$F$_5$, p-CF$_3$C$_6$H$_4$), epoxide (e.g., epoxybutadiene), or cyano (—CN), wherein n is 1, 2, or 3, and R is a hydrogen, methyl, substituted C$_2$-C$_6$ alkyl, unsubstituted C$_2$-C$_6$ alkyl, substituted aryl, or unsubstituted aryl. Examples of electron withdrawing groups of various embodiments include ester (—COOR), ketone (—COR), aldehyde (—COH), halides (—Cl, —F, —Br, —I), carboxylic acid (—COOH), sulfonic acid (—SO$_3$H), 1, 2° and 3° ammonium (—NR$_3^+$), nitro (—NO$_2$), or phthalamide.

In one example an at least one cross-metathesis product comprising a product internal olefin, wherein the product internal olefin is in the Z-configuration may be represented by the structure of Formula (X):

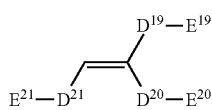

Formula (X)

wherein:

$D^{19}$, $D^{20}$, and $D^{21}$ are independently selected from nil, CH$_2$, O, or S; and $E^{19}$, $E^{20}$, and $E^{21}$ are independently selected from hydrogen, hydrocarbyl (e.g., C$_1$-C$_{20}$ alkyl, C$_5$-C$_{20}$ aryl, C$_5$-C$_{30}$ aralkyl, or C$_5$-C$_{30}$ alkaryl), substituted hydrocarbyl (e.g., substituted C$_1$-C$_{20}$ alkyl, C$_5$-C$_{20}$ aryl, C$_5$-C$_{30}$ aralkyl, or C$_5$-C$_{30}$ alkaryl), heteroatom-containing hydrocarbyl (e.g., C$_1$-C$_{20}$ heteroalkyl, C$_5$-C$_{20}$ heteroaryl, heteroatom-containing C$_5$-C$_{30}$ aralkyl, or heteroatom-containing C$_5$-C$_{30}$ alkaryl), and substituted heteroatom-containing hydrocarbyl (e.g., substituted C$_1$-C$_{20}$ heteroalkyl, C$_5$-C$_{20}$ heteroaryl, heteroatom-containing C$_5$-C$_{30}$ aralkyl, or heteroatom-containing C$_5$-C$_{30}$ alkaryl) and, if substituted hydrocarbyl or substituted heteroatom-containing hydrocarbyl, wherein the substituents may be functional groups ("Fn") such as halo, hydroxyl, sulfhydryl, C$_1$-C$_{24}$ alkoxy, C$_5$-C$_{24}$ aryloxy, C$_6$-C$_{24}$ aralkyloxy, C$_6$-C$_{24}$ alkaryloxy, acyl (including C$_2$-C$_{24}$ alkylcarbonyl (—CO-alkyl) and C$_6$-C$_{24}$ arylcarbonyl (—CO-aryl)), acyloxy (—O-acyl, including C$_2$-C$_{24}$ alkylcarbonyloxy (—O—CO-alkyl) and C$_6$-C$_{24}$ arylcarbonyloxy (—O—CO-aryl)), C$_2$-C$_{24}$ alkoxycarbonyl (—(CO)—O-alkyl), C$_6$-C$_{24}$ aryloxycarbonyl (—(CO)—O-aryl), halocarbonyl (—CO)—X where X is halo), C$_2$-C$_{24}$ alkylcarbonato (—O—(CO)—O-alkyl), C$_6$-C$_{24}$ arylcarbonato (—O—(CO)—O-aryl), carboxy (—COOH), carboxylato (—COO—), carbamoyl (—(CO)—NH$_2$), mono-(C$_1$-C$_{24}$ alkyl)-substituted carbamoyl (—(CO)—NH(C$_1$-C$_{24}$ alkyl)), di-(C$_1$-C$_{24}$ alkyl)-substituted carbamoyl (—(CO)—N(C$_1$-C$_{24}$ alkyl)$_2$), mono-(C$_1$-C$_{24}$ haloalkyl)-substituted carbamoyl (—(CO)—NH(C$_1$-C$_{24}$ haloalkyl)), di-(C$_1$-C$_{24}$ haloalkyl)-substituted carbamoyl (—(CO)—N(C$_1$-C$_{24}$ haloalkyl)$_2$), mono-(C$_5$-C$_{24}$ aryl)-substituted carbamoyl (—(CO)—NH-aryl), di-(C$_5$-C$_{24}$ aryl)-substituted carbamoyl (—(CO)—N(C$_5$-C$_{24}$ aryl)$_2$), di-N—(C$_1$-C$_{24}$ alkyl), N—(C$_5$-C$_{24}$ aryl)-substituted carbamoyl (—(CO)—N(C$_1$-C$_{24}$ alkyl)(C$_5$-C$_{24}$ aryl), thiocarbamoyl (—(CS)—NH$_2$), mono-(C$_1$-C$_{24}$ alkyl)-substituted thiocarbamoyl (—(CS)—NH(C$_1$-C$_{24}$ alkyl)), di-(C$_1$-C$_{24}$ alkyl)-substituted thiocarbamoyl (—(CS)—N(C—C$_{24}$ alkyl)$_2$), mono-(C$_5$-C$_{24}$ aryl)-substituted thiocarbamoyl (—(CS)—NH-aryl), di-(C$_5$-C$_{24}$ aryl)-substituted thiocarbamoyl (—(CS)—N(C$_5$-C$_{24}$ aryl)$_2$), di-N—(C—C$_{24}$ alkyl), N—(C$_5$-C$_{24}$ aryl)-substituted thiocarbamoyl (—(CS)—N(C$_1$-C$_{24}$ alkyl)(C$_5$-C$_{24}$ aryl), carbamido (—NH—(CO)—NH$_2$), cyano (—C≡N), cyanato (—O—C≡N), thiocyanato (—S—C≡N), isocyanate (—N=C=O), thioisocyanate (—N=C=S), formyl (—(CO)—H), thioformyl (—(CS)—H), amino (—NH$_2$), mono-(C—C$_{24}$ alkyl)-substituted amino (—NH(C—C$_{24}$ alkyl), di-(C$_1$-C$_{24}$ alkyl)-substituted amino (—N(C$_1$-C$_{24}$ alkyl)$_2$), mono-(C$_5$-C$_{24}$ aryl)-substituted amino (—NH(C$_5$-C$_{24}$ aryl), di-(C$_5$-C$_{24}$ aryl)-substituted amino (—N(C$_5$-C$_{24}$ aryl)$_2$), C$_2$-C$_{24}$ alkylamido (—NH—(CO)-alkyl), C$_6$-C$_{24}$ arylamido (—NH—(CO)-aryl), imino (—CR=NH where R includes without limitation hydrogen, C$_1$-C$_{24}$ alkyl, C$_5$-C$_{24}$ aryl, C$_6$-C$_{24}$ alkaryl, C$_6$-C$_{24}$ aralkyl, etc.), C$_2$-C$_{20}$ alkylimino (—CR=N(alkyl), where R includes without limitation hydrogen, C$_1$-C$_{24}$ alkyl, C$_5$-C$_{24}$ aryl, C$_6$-C$_{24}$ alkaryl, C$_6$-C$_{24}$ aralkyl, etc.), arylimino (—CR=N(aryl), where R includes without limitation hydrogen, C$_1$-C$_{20}$ alkyl, C$_5$-C$_{24}$ aryl, C$_6$-C$_{24}$ alkaryl, C$_6$-C$_{24}$ aralkyl, etc.), nitro (—NO$_2$), nitroso (—NO), sulfo (—SO$_2$—OH), sulfonato (—SO$_2$—O—), C$_1$-C$_{24}$ alkylsulfanyl (—S-alkyl; also termed "alkylthio"), C$_5$-C$_{24}$ arylsulfanyl (—S-aryl; also termed "arylthio"), C$_1$-C$_{24}$ alkylsulfinyl (—(SO)-alkyl), C$_5$-C$_{24}$ arylsulfinyl (—(SO)-aryl), C$_1$-C$_{24}$ alkylsulfonyl (—SO$_2$-alkyl), C$_1$-C$_{24}$ monoalkylaminosulfonyl (—SO$_2$—N(H) alkyl), C$_1$-C$_{24}$ dialkylaminosulfonyl (—SO$_2$—N(alkyl)$_2$), C$_5$-C$_{24}$ arylsulfonyl (—SO$_2$-aryl), boryl (—BH$_2$), borono (—B(OH)$_2$), boronato (—B(OR)$_2$ where R is alkyl or aryl), phosphono (—P(O)(OH)$_2$), phosphonato (—P(O)(O$^-$)$_2$), phosphinato (—P(O)(O$^-$)), phospho (—PO$_2$), and phosphino (—PH$_2$); and the hydrocarbyl moieties C$_1$-C$_{24}$ alkyl (preferably C$_1$-C$_{12}$ alkyl, more preferably C$_1$-C$_6$ alkyl), C$_5$-C$_{24}$ aryl (preferably C$_5$-C$_{14}$ aryl), C$_6$-C$_{24}$ alkaryl (preferably C$_6$-C$_{16}$ alkaryl), and C$_6$-C$_{24}$ aralkyl (preferably C$_6$-C$_{16}$ aralkyl); and where if $E^{19}$ and $E^{20}$ are the same, then $D^{19}$ and $D^{20}$ must be different, and if $D^{19}$ and $D^{20}$ are the same then $E^{19}$ and $E^{20}$ must be different; and where if $E^{21}$ is hydrogen, then $D^{21}$ cannot be nil.

Moreover, in one embodiment, for at least one cross-metathesis product comprising a product internal olefin represented by the structure of Formula (X), the functional groups may be selected from electron withdrawing groups. Examples of electron withdrawing groups of various embodiments may include, but are not limited to, aldehyde (—COH), ketone (—COR), acyl (—COR), carbonyl (—CO), carboxylic acid (—COOH), ester (—COOR), ester (—OCOR), sulfonamide (—NRSO$_2$Ar), carbamate (—NCO$_2$R), epoxide (e.g., epoxybutadiene), halides (—Cl, —F, —Br, —I), fluoromethyl (—CF$_n$), fluroaryl (e.g., —C$_6$F$_5$, p-CF$_3$C$_6$H$_4$), cyano (—CN), sulfoxide (—SOR), sulfonyl (—SO$_2$R), sulfonic acid (—SO$_3$H), phthalamide, 1, 2° and 3° ammonium (—NR$_3^+$), or nitro (—NO$_2$), wherein n is 1, 2, or 3, and R is a hydrogen, methyl, substituted C$_2$-C$_6$ alkyl, unsubstituted C$_2$-C$_6$ alkyl, substituted aryl, or unsubstituted aryl. Examples of electron withdrawing groups of various embodiments include ester (—OCOR), sulfonamide (—NRSO$_2$Ar), carbamate (—NCO$_2$R), sulfonyl (—SO$_2$R), fluoromethyl (—CF$_n$), fluroaryl (e.g., —C$_6$F$_5$, p-CF$_3$C$_6$H$_4$), epoxide (e.g., epoxybutadiene), or cyano (—CN), wherein n is 1, 2, or 3, and R is a hydrogen, methyl, substituted $C_2$-$C_6$ alkyl, unsubstituted $C_2$-$C_6$ alkyl, substituted aryl, or unsubstituted aryl. Examples of electron withdrawing groups of various embodiments include ester (—COOR), ketone (—COR), aldehyde (—COH), halides (—Cl, —F, —Br, —I), carboxylic acid (—COOH), sulfonic acid (—$SO_3H$), 1, 2° and 3° ammonium (—$NR_3^+$), nitro (—$NO_2$), or phthalamide.

In one example an at least one cross-metathesis product comprising a product internal olefin, wherein the product internal olefin is in the Z-configuration may be represented by the structure of Formula (XI):

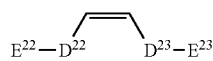

Formula (XI)

wherein:

$D^{22}$ and $D^{23}$ are independently selected from nil, $CH_2$, O, or S; and $E^{22}$ and $E^{23}$ are independently selected from hydrogen, hydrocarbyl (e.g., $C_1$-$C_{20}$ alkyl, $C_5$-$C_{20}$ aryl, $C_5$-$C_{30}$ aralkyl, or $C_5$-$C_{30}$ alkaryl), substituted hydrocarbyl (e.g., substituted $C_1$-$C_{20}$ alkyl, $C_5$-$C_{20}$ aryl, $C_5$-$C_{30}$ aralkyl, or $C_5$-$C_{30}$ alkaryl), heteroatom-containing hydrocarbyl (e.g., $C_1$-$C_{20}$ heteroalkyl, $C_5$-$C_{20}$ heteroaryl, heteroatom-containing $C_5$-$C_{30}$ aralkyl, or heteroatom-containing $C_5$-$C_{30}$ alkaryl), and substituted heteroatom-containing hydrocarbyl (e.g., substituted $C_1$-$C_{20}$ heteroalkyl, $C_5$-$C_{20}$ heteroaryl, heteroatom-containing $C_5$-$C_{30}$ aralkyl, or heteroatom-containing $C_5$-$C_{30}$ alkaryl) and, if substituted hydrocarbyl or substituted heteroatom-containing hydrocarbyl, wherein the substituents may be functional groups ("Fn") such as halo, hydroxyl, sulfhydryl, $C_1$-$C_{24}$ alkoxy, $C_5$-$C_{24}$ aryloxy, $C_6$-$C_{24}$ aralkyloxy, $C_6$-$C_{24}$ alkaryloxy, acyl (including $C_2$-$C_{24}$ alkylcarbonyl (—CO-alkyl) and $C_6$-$C_{24}$ arylcarbonyl (—CO-aryl)), acyloxy (—O-acyl, including $C_2$-$C_{24}$ alkylcarbonyloxy (—O—CO-alkyl) and $C_6$-$C_{24}$ arylcarbonyloxy (—O—CO-aryl)), $C_2$-$C_{24}$ alkoxycarbonyl (—(CO)—O-alkyl), $C_6$-$C_{24}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{24}$ arylcarbonato (—O—(CO)—O-aryl), carboxy (—COOH), carboxylato (—COO—), carbamoyl (—(CO)—$NH_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)$_2$), mono-($C_1$-$C_{24}$ haloalkyl)-substituted carbamoyl (—(CO)—NH($C_1$-$C_{24}$ haloalkyl)), di-($C_1$-$C_{24}$ haloalkyl)-substituted carbamoyl (—(CO)—N($C_1$-$C_{24}$ haloalkyl)$_2$), mono-($C_5$-$C_{24}$ aryl)-substituted carbamoyl (—(CO)—NH-aryl), di-($C_5$-$C_{24}$ aryl)-substituted carbamoyl (—(CO)—N($C_5$-$C_{24}$ aryl)$_2$), di-N—($C_1$-$C_{24}$ alkyl), N—($C_5$-$C_{24}$ aryl)-substituted carbamoyl (—(CO)—N(C—$C_{24}$ alkyl)($C_5$-$C_{24}$ aryl), thiocarbamoyl (—(CS)—$NH_2$), mono-($C_1$-$C_{24}$ alkyl)-substituted thiocarbamoyl (—(CS)—NH($C_1$-$C_{24}$ alkyl)), di-($C_1$-$C_{24}$ alkyl)-substituted thiocarbamoyl (—(CS)—N($C_1$-$C_{24}$ alkyl)$_2$), mono-($C_5$-$C_{24}$ aryl)-substituted thiocarbamoyl (—(CS)—NH-aryl), di-($C_5$-$C_{24}$ aryl)-substituted thiocarbamoyl (—(CS)—N($C_5$-$C_{24}$ aryl)$_2$), di-N—($C_1$-$C_{24}$ alkyl), N—($C_5$-$C_{24}$ aryl)-substituted thiocarbamoyl (—(CS)—N($C_1$-$C_{24}$ alkyl)($C_5$-$C_{24}$ aryl), carbamido (—NH—(CO)—$NH_2$), cyano (—C≡N), cyanato (—O—C≡N), thiocyanato (—S—C≡N), isocyanate (—N═C═O), thioisocyanate (—N═C═S), formyl (—(CO)—H), thio-formyl (—(CS)—H), amino (—$NH_2$), mono-($C_1$-$C_{24}$ alkyl)-substituted amino (—NH($C_1$-$C_{24}$ alkyl), di-($C_1$-$C_{24}$ alkyl)-substituted amino (—N($C_1$-$C_{24}$ alkyl)$_2$), mono-($C_5$-$C_{24}$ aryl)-substituted amino (—NH($C_5$-$C_{24}$ aryl), di-($C_5$-$C_{24}$ aryl)-substituted amino (—N($C_5$-$C_{24}$ aryl)$_2$), $C_2$-$C_{24}$ alkylamido (—NH—(CO)-alkyl), $C_6$-$C_{24}$ arylamido (—NH—(CO)-aryl), imino (—CR═NH where R includes without limitation hydrogen, $C_1$-$C_{24}$ alkyl, $C_5$-$C_{24}$ aryl, $C_6$-$C_{24}$ alkaryl, $C_6$-$C_{24}$ aralkyl, etc.), $C_2$-$C_{20}$ alkylimino (—CR═N(alkyl), where R includes without limitation hydrogen, $C_1$-$C_{24}$ alkyl, $C_5$-$C_{24}$ aryl, $C_6$-$C_{24}$ alkaryl, $C_6$-$C_{24}$ aralkyl, etc.), arylimino (—CR═N(aryl), where R includes without limitation hydrogen, $C_1$-$C_{20}$ alkyl, $C_5$-$C_{24}$ aryl, $C_6$-$C_{24}$ alkaryl, $C_6$-$C_{24}$ aralkyl, etc.), nitro (—$NO_2$), nitroso (—NO), sulfo (—$SO_2$—OH), sulfonato (—$SO_2$—O—), $C_1$-$C_{24}$ alkylsulfanyl (—S-alkyl; also termed "alkylthio"), $C_5$-$C_{24}$ arylsulfanyl (—S-aryl; also termed "arylthio"), $C_1$-$C_{24}$ alkylsulfinyl (—(SO)-alkyl), $C_5$-$C_{24}$ arylsulfinyl (—(SO)-aryl), $C_1$-$C_{24}$ alkylsulfonyl (—$SO_2$-alkyl), $C_1$-$C_{24}$ monoalkylaminosulfonyl (—$SO_2$—N(H) alkyl), $C_1$-$C_{24}$ dialkylaminosulfonyl (—$SO_2$—N(alkyl)$_2$), $C_5$-$C_{24}$ arylsulfonyl (—$SO_2$-aryl), boryl (—$BH_2$), borono (—B(OH)$_2$), boronato (—B(OR)$_2$ where R is alkyl or aryl), phosphono (—P(O)(OH)$_2$), phosphonato (—P(O)(O$^-$)$_2$), phosphinato (—P(O)(O$^-$)), phospho (—$PO_2$), and phosphino (—$PH_2$); and the hydrocarbyl moieties $C_1$-$C_{24}$ alkyl (preferably C—$C_{12}$ alkyl, more preferably $C_1$-$C_6$ alkyl), $C_5$-$C_{24}$ aryl (preferably $C_5$-$C_{14}$ aryl), $C_6$-$C_{24}$ alkaryl (preferably $C_6$-$C_{16}$ alkaryl), and $C_6$-$C_{24}$ aralkyl (preferably $C_6$-$C_{16}$ aralkyl); and where if $E^{22}$ is hydrogen, then $D^{22}$ cannot be nil; and where if $E^{23}$ is hydrogen, then $D^{23}$ cannot be nil.

Moreover, in one embodiment, for at least one cross-metathesis product comprising a product internal olefin represented by the structure of Formula (XI), the functional groups may be selected from electron withdrawing groups. Examples of electron withdrawing groups of various embodiments may include, but are not limited to, aldehyde (—COH), ketone (—COR), acyl (—COR), carbonyl (—CO), carboxylic acid (—COOH), ester (—COOR), ester (—OCOR), sulfonamide (—$NRSO_2Ar$), carbamate (—$NCO_2R$), epoxide (e.g., epoxybutadiene), halides (—Cl, —F, —Br, —I), fluoromethyl (—$CF_n$), fluoraryl (e.g., —$C_6F_5$, p-$CF_3C_6H_4$), cyano (—CN), sulfoxide (—SOR), sulfonyl (—$SO_2R$), sulfonic acid (—$SO_3H$), phthalamide, 1, 2° and 3° ammonium (—$NR_3^+$), or nitro (—$NO_2$), wherein n is 1, 2, or 3, and R is a hydrogen, methyl, substituted $C_2$-$C_6$ alkyl, unsubstituted $C_2$-$C_6$ alkyl, substituted aryl, or unsubstituted aryl. Examples of electron withdrawing groups of various embodiments include ester (—OCOR), sulfonamide (—$NRSO_2Ar$), carbamate (—$NCO_2R$), sulfonyl (—$SO_2R$), fluoromethyl (—$CF_n$), fluoraryl (e.g., —$C_6F_5$, p-$CF_3C_6H_4$), epoxide (e.g., epoxybutadiene), or cyano (—CN), wherein n is 1, 2, or 3, and R is a hydrogen, methyl, substituted $C_2$-$C_6$ alkyl, unsubstituted $C_2$-$C_6$ alkyl, substituted aryl, or unsubstituted aryl. Examples of electron withdrawing groups of various embodiments include ester (—COOR), ketone (—COR), aldehyde (—COH), halides (—Cl, —F, —Br, —I), carboxylic acid (—COOH), sulfonic acid (—$SO_3H$), 1, 2° and 3° ammonium (—$NR_3^+$), nitro (—$NO_2$), or phthalamide.

In another embodiment of the invention, an at least one cross-metathesis product comprising a product internal olefin, wherein the product internal olefin is in the Z-configuration, may be represented by the structure of Formula (XI), wherein: $D^{22}$ and $D^{23}$ are $CH_2$; and $E^{22}$ and $E^{23}$ are independently functional groups ("Fn") such as: acyloxy (—O-acyl, including $C_2$-$C_{24}$ alkylcarbonyloxy (—O—CO-alkyl) and $C_6$-$C_{24}$ arylcarbonyloxy (—O—CO-aryl)), $C_2$-$C_{24}$ alkylcarbonato (—O—(CO)—O-alkyl), $C_6$-$C_{24}$ arylcarbonato (—O—(CO)—O-aryl), carbamido (—NH—(CO)—NH$_2$), —NH—(CO)—NHR, —NH—(CO)—NR$^2$, $C_2$-$C_{24}$ alkylamido (—NH—(CO)-alkyl), $C_6$-$C_{24}$ arylamido (—NH—(CO)-aryl), nitro (—NO$_2$), nitroso (—NO), sulfo (—SO$_2$—OH), sulfonato (—SO$_2$—O—), $C_1$-$C_{24}$ alkylsulfinyl (—(SO)-alkyl), $C_5$-$C_{24}$ arylsulfinyl (—(SO)-aryl), $C_1$-$C_{24}$ alkylsulfonyl (—SO$_2$-alkyl), $C_1$-$C_{24}$ monoalkylaminosulfonyl (—SO$_2$—N(H) alkyl), $C_1$-$C_{24}$ dialkylaminosulfonyl (—SO$_2$—N(alkyl)$_2$), $C_5$-$C_{24}$ arylsulfonyl (—SO$_2$-aryl), phosphono (—P(O)(OH)$_2$), phosphonato (—P(O)(O$^-$)$_2$), phosphinato (—P(O)(O$^-$)), phospho (—PO$_2$), —O—P(O)(OR)$_2$, (wherein R is $C_1$-$C_{24}$ alkyl, ($C_5$-$C_{24}$ aryl), $C_6$-$C_{24}$ alkaryl, $C_6$-$C_{24}$ aralkyl), or an electron withdrawing group such as: ester (—OCOR), sulfonamide (—NRSO$_2$Ar), carbamate (—NCO$_2$R), sulfoxide (—SOR), sulfonyl (—SO$_2$R), sulfonic acid (—SO$_3$H), phthalamide, or nitro (—NO$_2$), wherein R is a hydrogen, methyl, substituted $C_2$-$C_6$ alkyl, unsubstituted $C_2$-$C_6$ alkyl, substituted aryl, or unsubstituted aryl.

In another embodiment of the invention, an at least one cross-metathesis product comprising a product internal olefin, wherein the product internal olefin is in the Z-configuration, may be represented by the structure of Formula (XI), wherein: $D^{22}$ and $D^{23}$ are CH$_2$; and $E^{22}$ and $E^{23}$ are independently electron withdrawing groups such as: ester (—OCOR), sulfonamide (—NRSO$_2$Ar), carbamate (—NCO$_2$R), sulfonyl (—SO$_2$R), sulfonic acid (—SO$_3$H), phthalamide, or nitro (—NO$_2$), wherein R is a hydrogen, methyl, substituted $C_2$-$C_6$ alkyl, unsubstituted $C_2$-$C_6$ alkyl, substituted aryl, or unsubstituted aryl.

Cyclic Olefins

In general, any cyclic olefin suitable for the metathesis reactions disclosed herein may be used, in the present invention. Such cyclic olefins may be optionally substituted, optionally heteroatom-containing, mono-unsaturated, di-unsaturated, or poly-unsaturated $C_5$ to $C_{24}$ hydrocarbons that may be mono-, di-, or poly-cyclic. The cyclic olefin may generally be any strained or unstrained cyclic olefin, provided the cyclic olefin is able to participate in a ROMP reaction either individually or as part of a cyclic olefin composition or as part of a ROMP composition. Furthermore, a plurality (a mixture) of different cyclic olefins may be used in a cyclic olefin composition or a ROMP composition. While certain unstrained cyclic olefins such as cyclohexene are generally understood to not undergo ROMP reactions by themselves, under appropriate circumstances, such unstrained cyclic olefins may nonetheless be ROMP active. For example, when present as a co-monomer in a ROMP composition, unstrained cyclic olefins may be ROMP active. Accordingly, as used herein and as would be appreciated by the skilled artisan, the term "unstrained cyclic olefin" is intended to refer to those unstrained cyclic olefins that may undergo a ROMP reaction under any conditions, or in any ROMP composition, provided the unstrained cyclic olefin is ROMP active.

In general, the cyclic olefin may be represented by the structure of Formula (A):

wherein J, $R^{A1}$, and $R^{A2}$ are as follows: $R^{A1}$ and $R^{A2}$ are selected independently from the group consisting of hydrogen, hydrocarbyl (e.g., $C_1$-$C_{20}$ alkyl, $C_5$-$C_{20}$ aryl, $C_5$-$C_{30}$ aralkyl, or $C_5$-$C_{30}$ alkaryl), substituted hydrocarbyl (e.g., substituted $C_1$-$C_{20}$ alkyl, $C_5$-$C_{20}$ aryl, $C_5$-$C_{30}$ aralkyl, or $C_5$-$C_{30}$ alkaryl), heteroatom-containing hydrocarbyl (e.g., $C_1$-$C_{20}$ heteroalkyl, $C_5$-$C_{20}$ heteroaryl, heteroatom-containing $C_5$-$C_{30}$ aralkyl, or heteroatom-containing $C_5$-$C_{30}$ alkaryl), and substituted heteroatom-containing hydrocarbyl (e.g., substituted $C_1$-$C_{20}$ heteroalkyl, $C_5$-$C_{20}$ heteroaryl, heteroatom-containing $C_5$-$C_{30}$ aralkyl, or heteroatom-containing $C_5$-$C_{30}$ alkaryl) and, if substituted hydrocarbyl or substituted heteroatom-containing hydrocarbyl, wherein the substituents may be functional groups ("Fn") such as phosphonato, phosphoryl, phosphanyl, phosphino, sulfonato, $C_1$-$C_{20}$ alkylsulfanyl, $C_5$-$C_{20}$ arylsulfanyl, $C_1$-$C_{20}$ alkylsulfonyl, $C_5$-$C_{20}$ arylsulfonyl, $C_1$-$C_{20}$ alkylsulfinyl, $C_5$-$C_{20}$ arylsulfinyl, sulfonamido, amino, amido, imino, nitro, nitroso, hydroxyl, $C_1$-$C_{20}$ alkoxy, $C_5$-$C_{20}$ aryloxy, $C_2$-$C_{20}$ alkoxycarbonyl, $C_5$-$C_{20}$ aryloxycarbonyl, carboxyl, carboxylato, mercapto, formyl, $C_1$-$C_{20}$ thioester, cyano, cyanato, thiocyanato, isocyanate, thioisocyanate, carbamoyl, epoxy, styrenyl, silyl, silyloxy, silanyl, siloxazanyl, boronato, boryl, or halogen, or a metal-containing or metalloid-containing group (wherein the metal may be, for example, Sn or Ge). $R^{A1}$ and $R^{A2}$ may itself be one of the aforementioned groups, such that the Fn moiety is directly bound to the olefinic carbon atom indicated in the structure. In the latter case, however, the functional group will generally not be directly bound to the olefinic carbon through a heteroatom containing one or more lone pairs of electrons, e.g., an oxygen, sulfur, nitrogen, or phosphorus atom, or through an electron-rich metal or metalloid such as Ge, Sn, As, Sb, Se, Te, etc. With such functional groups, there will normally be an intervening linkage Z*, such that $R^{A1}$ and/or $R^{A2}$ then has the structure —(Z*)$_n$-Fn wherein n is 1, Fn is the functional group, and Z* is a hydrocarbylene linking group such as an alkylene, substituted alkylene, heteroalkylene, substituted heteroalkene, arylene, substituted arylene, heteroarylene, or substituted heteroarylene linkage. J is a saturated or unsaturated hydrocarbylene, substituted hydrocarbylene, heteroatom-containing hydrocarbylene, or substituted heteroatom-containing hydrocarbylene linkage, wherein when J is substituted hydrocarbylene or substituted heteroatom-containing hydrocarbylene, the substituents may include one or more —(Z*)$_n$-Fn groups, wherein n is zero or 1, and Fn and Z* are as defined previously. Additionally, two or more substituents attached to ring carbon (or other) atoms within J may be linked to form a bicyclic or polycyclic olefin. J will generally contain in the range of approximately 5 to 14 ring atoms, typically 5 to 8 ring atoms, for a monocyclic olefin, and, for bicyclic and polycyclic olefins, each ring will generally contain 4 to 8, typically 5 to 7, ring atoms.

Mono-unsaturated cyclic olefins encompassed by Formula (A) may be represented by the Formula (B).

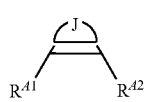

Formula (A)

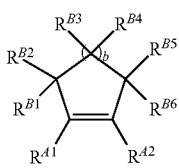

Formula (B)

wherein b is an integer generally, although not necessarily, in the range of 1 to 10, typically 1 to 5, $R^{A1}$ and $R^{A2}$ are as defined above for Formula (A), and $R^{B1}$, $R^{B2}$, $R^{B3}$, $R^{B4}$, $R^{B5}$, and $R^{B6}$ are independently selected from the group consisting of hydrogen, hydrocarbyl, substituted hydrocarbyl, heteroatom-containing hydrocarbyl, substituted heteroatom-containing hydrocarbyl and —$(Z^*)_n$-Fn where n, $Z^*$ and Fn are as defined previously, and wherein if any of the RB through $R^{B6}$ moieties is substituted hydrocarbyl or substituted heteroatom-containing hydrocarbyl, the substituents may include one or more —$(Z^*)_n$-Fn groups. Accordingly, $R^{B1}$, $R^{B2}$, $R^{B3}$, $R^{B4}$, $R^{B5}$, and $R^{B6}$ may be, for example, hydrogen, hydroxyl, $C_1$-$C_2$ alkyl, $C_5$-$C_{20}$ aryl, $C_1$-$C_{20}$ alkoxy, $C_5$-$C_{20}$ aryloxy, $C_2$-$C_{20}$ alkoxycarbonyl, $C_5$-$C_{20}$ aryloxycarbonyl, amino, amido, nitro, etc.

Furthermore, any of the $R^{B1}$, $R^{B2}$, $R^{B3}$, $R^{B4}$, $R^{B5}$, and $R^{B6}$ moieties can be linked to any of the other $R^{B1}$, $R^{B2}$, $R^{B3}$, $R^{B4}$, $R^{B5}$, and $R^{B6}$ moieties to provide a substituted or unsubstituted alicyclic group containing 4 to 30 ring carbon atoms or a substituted or unsubstituted aryl group containing 6 to 18 ring carbon atoms or combinations thereof and the linkage may include heteroatoms or functional groups, e.g., the linkage may include without limitation an ether, ester, thioether, amino, alkylamino, imino, or anhydride moiety. The alicyclic group can be monocyclic, bicyclic, or polycyclic. When unsaturated the cyclic group can contain monounsaturation or multiunsaturation, with monounsaturated cyclic groups being preferred. When substituted, the rings contain monosubstitution or multisubstitution wherein the substituents are independently selected from hydrogen, hydrocarbyl, substituted hydrocarbyl, heteroatom-containing hydrocarbyl, substituted heteroatom-containing hydrocarbyl, —$(Z^*)_n$-Fn where n is zero or 1, $Z^*$ and Fn are as defined previously, and functional groups (Fn) provided above.

Examples of monounsaturated, monocyclic olefins encompassed by Formula (B) include, without limitation, cyclopentene, cyclohexene, cycloheptene, cyclooctene, cyclononene, cyclodecene, cycloundecene, cyclododecene, tricyclodecene, tetracyclodecene, octacyclodecene, and cycloeicosene, and substituted versions thereof such as 1-methylcyclopentene, 1-ethylcyclopentene, 1-isopropylcyclohexene, 1-chloropentene, 1-fluorocyclopentene, 4-methylcyclopentene, 4-methoxy-cyclopentene, 4-ethoxy-cyclopentene, cyclopent-3-ene-thiol, cyclopent-3-ene, 4-methylsulfanyl-cyclopentene, 3-methylcyclohexene, 1-methylcyclooctene, 1,5-dimethylcyclooctene, etc.

Monocyclic diene reactants encompassed by Formula (A) may be generally represented by the Formula (C):

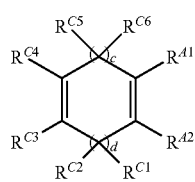

Formula (C)

wherein c and d are independently integers in the range of 1 to about 8, typically 2 to 4, preferably 2 (such that the reactant is a cyclooctadiene), $R^{A1}$ and $R^{A2}$ are as defined above for Formula (A), and $R^{C1}$, $R^{C2}$, $R^{C3}$, $R^{C4}$, $R^{C5}$, and $R^{C6}$ are defined as for $R^{B1}$ through $R^{B6}$. In this case, it is preferred that $R^{C3}$ and $R^{C4}$ be non-hydrogen substituents, in which case the second olefinic moiety is tetrasubstituted.

Examples of monocyclic diene reactants include, without limitation, 1,3-cyclopentadiene, 1,3-cyclohexadiene, 1,4-cyclohexadiene, 5-ethyl-1,3-cyclohexadiene, 1,3-cycloheptadiene, cyclohexadiene, 1,5-cyclooctadiene, 1,3-cyclooctadiene, and substituted analogs thereof. Triene reactants are analogous to the diene Formula (C), and will generally contain at least one methylene linkage between any two olefinic segments.

Bicyclic and polycyclic olefins encompassed by Formula (A) may be generally represented by the Formula (D):

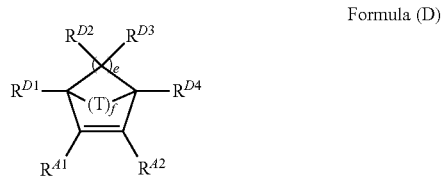

Formula (D)

wherein $R^{A1}$ and $R^{A2}$ are as defined above for Formula (A), $R^{D1}$, $R^{D2}$, $R^{D3}$, and $R^{D4}$ are as defined for RB through $R^{B6}$, e is an integer in the range of 1 to 8 (typically 2 to 4), f is generally 1 or 2; T is lower alkylene or alkenylene (generally substituted or unsubstituted methyl or ethyl), $CHR^{G1}$, $C(R^{G1})_2$, O, S, N—$R^{G1}$, P—$R^{G1}$, O=P—$R^{G1}$, $Si(R^{G1})_2$, B—$R^{G1}$, or As—$R^{G1}$ where $R^{G1}$ is alkyl, alkenyl, cycloalkyl, cycloalkenyl, aryl, alkaryl, aralkyl, or alkoxy. Furthermore, any of the $R^D$, $R^{D2}$, $R^{D3}$ and $R^{D4}$ moieties can be linked to any of the other $R^{D1}$, $R^{D2}$, $R^{D3}$, and $R^{D4}$ moieties to provide a substituted or unsubstituted alicyclic group containing 4 to 30 ring carbon atoms or a substituted or unsubstituted aryl group containing 6 to 18 ring carbon atoms or combinations thereof and the linkage may include heteroatoms or functional groups, e.g., the linkage may include without limitation an ether, ester, thioether, amino, alkylamino, imino, or anhydride moiety. The cyclic group can be monocyclic, bicyclic, or polycyclic. When unsaturated the cyclic group can contain monounsaturation or multiunsaturation, with monounsaturated cyclic groups being preferred. When substituted, the rings contain monosubstitution or multisubstitution wherein the substituents are independently selected from hydrogen, hydrocarbyl, substituted hydrocarbyl, heteroatom-containing hydrocarbyl, substituted heteroatom-containing hydrocarbyl, —$(Z^*)_n$-Fn where n is zero or 1, $Z^*$ and Fn are as defined previously, and functional groups (Fn) provided above.

Cyclic olefins encompassed by Formula (D) are in the norbornene family. As used herein, norbornene means any compound that includes at least one norbornene or substituted norbornene moiety, including without limitation norbornene, substituted norbornene(s), norbornadiene, substituted norbornadiene(s), polycyclic norbornenes, and substituted polycyclic norbornene(s). Norbornenes within this group may be generally represented by the Formula (E):

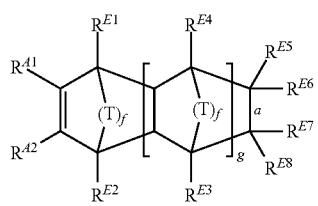

Formula (E)

wherein $R^{41}$ and $R^{42}$ are as defined above for Formula (A), T is as defined above for Formula (D), $R^{E1}$, $R^{E2}$, $R^{E3}$, $R^{E4}$, $R^{E5}$, $R^{E6}$, $R^{E7}$, and $R^{E8}$ are as defined for RB through $R^{B6}$, and "a" represents a single bond or a double bond, f is generally 1 or 2, "g" is an integer from 0 to 5, and when "a" is a double bond one of $R^E$, $R^{E6}$ and one of $R^{E7}$, $R^{E8}$ is not present.

Furthermore, any of the $R^{E5}$, $R^{E6}$, $R^{E7}$, and $R^{E8}$ moieties can be linked to any of the other $R^{E5}$, $R^{E6}$, $R^{E7}$, and $R^{E8}$ moieties to provide a substituted or unsubstituted alicyclic group containing 4 to 30 ring carbon atoms or a substituted or unsubstituted aryl group containing 6 to 18 ring carbon atoms or combinations thereof and the linkage may include heteroatoms or functional groups, e.g., the linkage may include without limitation an ether, ester, thioether, amino, alkylamino, imino, or anhydride moiety. The cyclic group can be monocyclic, bicyclic, or polycyclic. When unsaturated the cyclic group can contain monounsaturation or multiunsaturation, with monounsaturated cyclic groups being preferred. When substituted, the rings contain mono-substitution or multisubstitution wherein the substituents are independently selected from hydrogen, hydrocarbyl, substituted hydrocarbyl, heteroatom-containing hydrocarbyl, substituted heteroatom-containing hydrocarbyl, —(Z*)$_n$-Fn where n is zero or 1, Z* and Fn are as defined previously, and functional groups (Fn) provided above.

More preferred cyclic olefins possessing at least one norbornene moiety have the Formula (F):

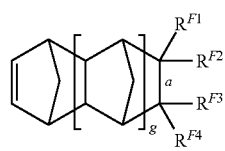

Formula (F)

wherein: $R^{F1}$, $R^{F2}$, $R^{F3}$, and $R^{F4}$ are as defined for $R^{B1}$ through $R^{B6}$ and "a" represents a single bond or a double bond, "g" is an integer from 0 to 5, and when "a" is a double bond one of $R^{F1}$, $R^{F2}$ and one of $R^{F3}$, $R^{F4}$ is not present.

Furthermore, any of the $R^{F1}$, $R^{F2}$, $R^{F3}$, and $R^{F4}$ moieties can be linked to any of the other $R^{F1}$, $R^{F2}$, $R^{F3}$ and $R^{F4}$ moieties to provide a substituted or unsubstituted alicyclic group containing 4 to 30 ring carbon atoms or a substituted or unsubstituted aryl group containing 6 to 18 ring carbon atoms or combinations thereof and the linkage may include heteroatoms or functional groups, e.g., the linkage may include without limitation an ether, ester, thioether, amino, alkylamino, imino, or anhydride moiety. The alicyclic group can be monocyclic, bicyclic, or polycyclic. When unsaturated the cyclic group can contain monounsaturation or multiunsaturation, with monounsaturated cyclic groups being preferred. When substituted, the rings contain mono-substitution or multisubstitution wherein the substituents are independently selected from hydrogen, hydrocarbyl, substituted hydrocarbyl, heteroatom-containing hydrocarbyl, substituted heteroatom-containing hydrocarbyl, —(Z*)$_n$-Fn where n is zero or 1, Z* and Fn are as defined previously, and functional groups (Fn) provided above.

Examples of cyclic olefins thus include, without limitation, dicyclopentadiene; tricyclopentadiene; dicyclohexadiene; norbornene; 5-methyl-2-norbornene; 5-ethyl-2-norbornene; 5-isobutyl-2-norbornene; 5,6-dimethyl-2-norbornene; 5-phenylnorbornene; 5-benzylnorbornene; 5-acetylnorbornene; 5-methoxycarbonylnorbornene; 5-ethoxycarbonyl-1-norbornene; 5-methyl-5-methoxy-carbonylnorbornene; 5-cyanonorbornene; 5,5,6-trimethyl-2-norbornene; cyclo-hexenylnorbornene; endo, exo-5,6-dimethoxynorbornene; endo, endo-5,6-dimethoxynorbornene; endo, exo-5-6-dimethoxycarbonylnorbornene; endo, endo-5,6-dimethoxycarbonylnorbornene; 2,3-dimethoxynorbornene; norbornadiene; tricycloundecene; tetracyclododecene; 8-methyltetracyclododecene; 8-ethyltetracyclododecene; 8-methoxycarbonyltetracyclododecene; 8-methyl-8-tetracyclo-dodecene; 8-cyanotetracyclododecene; pentacyclopentadecene; pentacyclohexadecene; higher order oligomers of cyclopentadiene such as cyclopentadiene tetramer, cyclopentadiene pentamer, and the like; and $C_2$-$C_{12}$ hydrocarbyl substituted norbornenes such as 5-butyl-2-norbornene; 5-hexyl-2-norbornene; 5-octyl-2-norbornene; 5-decyl-2-norbornene; 5-dodecyl-2-norbornene; 5-vinyl-2-norbornene; 5-ethylidene-2-norbornene; 5-isopropenyl-2-norbornene; 5-propenyl-2-norbornene; and 5-butenyl-2-norbornene, and the like. Examples of cyclic olefins include dicyclopentadiene, tricyclopentadiene, and higher order oligomers of cyclopentadiene, such as cyclopentadiene tetramer, cyclopentadiene pentamer, and the like, tetracyclododecene, norbornene, and $C_2$-$C_{12}$ hydrocarbyl substituted norbornenes, such as 5-butyl-2-norbornene, 5-hexyl-2-norbornene, 5-octyl-2-norbornene, 5-decyl-2-norbornene, 5-dodecyl-2-norbornene, 5-vinyl-2-norbornene, 5-ethylidene-2-norbornene, 5-isopropenyl-2-norbornene, 5-propenyl-2-norbornene, 5-butenyl-2-norbornene, and the like including structural isomers and/or stereoisomers, any and all of which are suitable for use in the present invention. Examples of cyclic olefins include dicyclopentadiene, tricyclopentadiene, and higher order oligomers of cyclopentadiene, such as cyclopentadiene tetramer, cyclopentadiene pentamer, and the like, tetracyclododecene, norbornene, and $C_2$-$C_{12}$ hydrocarbyl substituted norbornenes, such as 5-butyl-2-norbornene, 5-hexyl-2-norbornene, 5-octyl-2-norbornene, 5-decyl-2-norbornene, 5-dodecyl-2-norbornene, 5-vinyl-2-norbornene, 5-ethylidene-2-norbornene, 5-isopropenyl-2-norbornene, 5-propenyl-2-norbornene, 5-butenyl-2-norbornene, and the like including structural isomers and/or stereoisomers, any and all of which are suitable for use in the present invention. Examples of cyclic olefins include dicyclopentadiene, tricyclopentadiene, and higher order oligomers of cyclopentadiene, such as cyclopentadiene tetramer, cyclopentadiene pentamer, and the like, including structural isomers and/or stereoisomers, any and all of which are suitable for use in the present invention. Specifically the cyclic olefin is selected from dicyclopentadiene and tricyclopentadiene, and mixtures thereof, including structural isomers and/or stereoisomers, any and all of which are suitable for use in the present invention. Also the cyclic olefin may be a $C_5$ to $C_{24}$ cyclic hydrocarbon that contain one or more (typically 2 to 12) heteroatoms such as O, N, S, or P. For example, the cyclic olefin may be mono-, di-, or tri-cyclic. When the cyclic olefin comprises more than one ring, the rings may or may not be fused.

The cyclic olefins may also be substituted, for example, a $C_5$ to $C_{24}$ cyclic hydrocarbon wherein one or more (typically 2, 3, 4, or 5) of the hydrogens are replaced with non-hydrogen substituents. Suitable non-hydrogen substituents may be chosen from the substituents described hereinabove. For example, functionalized cyclic olefins, i.e., $C_5$ to $C_{24}$ cyclic hydrocarbons wherein one or more (typically 2, 3, 4, or 5) of the hydrogens are replaced with functional groups, are within the scope of the invention. Suitable functional groups may be chosen from the functional groups described hereinabove.

It is well understood by one of skill in the art that bicyclic and polycyclic olefins as disclosed herein may consist of a variety of structural isomers and/or stereoisomers, any and all of which are suitable for use in the present invention. Any reference herein to such bicyclic and polycyclic olefins unless specifically stated includes mixtures of any and all such structural isomers and/or stereoisomers.

Romp Compositions and Articles

ROMP compositions according to the invention, generally comprise at least one cyclic olefin, as described herein, combined with at least one olefin metathesis catalyst of the invention.

In one embodiment, the ROMP compositions according to the invention may optionally be formulated with additives. Suitable additives include, but are not limited to, gel modifiers, hardness modulators, impact modifiers, binders, crosslinkers, plasticizers, pigments, flame retardants, dyes, fibers and reinforcement materials, including sized reinforcements and substrates, such as those treated with finishes, coatings, coupling agents, film formers, lubricants, dispersants, fillers, functionalized silanes, peroxides, antioxidants, antiozonants, thixotropic agents and/or reaction inhibitors. The amount of additives present in the resin compositions may vary depending on the particular type of additive used. The concentration of the additives in the resin compositions typically ranges from, for example, 0.001-85 percent by weight, particularly, from 0.1-75 percent by weight, or even more particularly, from 2-60 percent by weight. The additives may be added to the reaction mixture in the absence of solvent, or as organic or aqueous solutions.

In one embodiment, the invention provides a method of making a ROMP composition comprising combining at least one cyclic olefin, as described herein, with at least one cyclic olefin metathesis catalyst of the invention.

Non-limiting examples of exogenous inhibitors or "gel modification additives" include water, tetrahydrofuran (THF), 2-methyltetrahydrofuran (2-Me-THF), diethyl ether ($(C_2H_5)_2O$), methyl-tert-butyl ether ($CH_3OC(CH_3)_3$), dimethoxyethane ($CH_3OCH_2CH_2OCH_3$), diglyme ($CH_3OCH_2OCH_2OCH_3$), trimethylphosphine ($PMe_3$), triethylphosphine ($PEt_3$), tributylphosphine ($PBu_3$), tri(orthotolyl)phosphine ($P$-$o$-$tolyl_3$), tri-tert-butylphosphine ($P$-tert-$Bu_3$), tricyclopentylphosphine ($PCp_3$), tricyclohexylphosphine ($PCy_3$), triisopropylphosphine ($P$-$i$-$Pr_3$), trioctylphosphine ($POct_3$), triisobutylphosphine ($P$-$i$-$Bu_3$), triphenylphosphine ($PPh_3$), tri(pentafluorophenyl)phosphine ($P(C_6F_5)_3$), methyldiphenylphosphine ($PMePh_2$), dimethylphenylphosphine ($PMe_2Ph$), diethylphenylphosphine ($PEt_2Ph$), trimethylphosphite ($P(OMe)_3$), triethylphosphite, ($P(OEt)_3$), triisopropylphosphite ($P(O$-$i$-$Pr)_3$), tributylphosphite ($P(OBu)_3$), triphenylphosphite ($P(OPh)_3$, and tribenzylphosphine ($P(CH_2Ph)_3$), 2-cyclohexenone, and triphenylphosphine oxide.

In another embodiment, ROMP compositions according to the invention may additionally comprise a hydroperoxide gel modifier. Hydroperoxide gel modifiers for use in the present invention are disclosed in International Pat. App. No. PCT/US2012/042850. Non-limiting examples of hydroperoxide gel modifiers include tert-butyl hydroperoxide, tert-amyl hydroperoxide, cumene hydroperoxide, diisopropyl benzene hydroperoxide, (2,5-dihydroperoxy)-2,5-dimethylhexane, cyclohexyl hydroperoxide, triphenylmethyl hydroperoxide, pinane hydroperoxide (e.g., Glidox® 500; LyondellBasell), and paramenthane hydroperoxide (e.g., Glidox® 300; LyondellBasell).

ROMP compositions of the invention may additionally comprise a crosslinker, for example, a crosslinker selected from dialkyl peroxides, diacyl peroxides, and peroxyacids. Examples of such crosslinkers are disclosed in U.S. Pat. No. 5,728,785.

In another embodiment, ROMP compositions of the invention may additionally comprise at least one impact modifier. Suitable impact modifiers or elastomers include without limitation natural rubber, butyl rubber, polyisoprene, polybutadiene, polyisobutylene, ethylene-propylene copolymer, styrene-butadiene-styrene triblock rubber, random styrene-butadiene rubber, styrene-isoprene-styrene triblock rubber, styrene-ethylene/butylene-styrene copolymer, styrene-ethylene/propylene-styrene copolymer, ethylene-propylene-diene terpolymers, ethylene-vinyl acetate, and nitrile rubbers. Preferred impact modifiers or elastomers are polybutadiene Diene 55AC10 (Firestone), polybutadiene Diene 55AM5 (Firestone), EPDM Royalene 301T, EPDM Buna T9650 (Bayer), styrene-ethylene/butylene-styrene copolymer Kraton G1651H, Polysar Butyl 301 (Bayer), polybutadiene Taktene 710 (Bayer), styrene-ethylene/butylene-styrene Kraton G1726M, Ethylene-Octene Engage 8150 (DuPont-Dow), styrene-butadiene Kraton D1184, EPDM Nordel 1070 (DuPont-Dow), and polyisobutylene Vistanex MML-140 (Exxon), hydrogenated styrene-ethylene/butylene-styrene copolymer Kraton G1650M, hydrogenated styrene-ethylene/butylene-styrene copolymer Kraton G1657M, and styrene-butadiene block copolymer Kraton D1101, impact modifiers according to the invention generally manufactured by Addivant™ sold under the trade names of Royaltuf® (e.g., Royaltuf® 498, Royaltuf® 485) or high performance elastomers manufactured by Kraton Polymers sold under the trade names of Kraton® (e.g., Kraton® G1650, Kraton® G1652, Kraton® FG1901, Kraton® FG1924).

In another embodiment, ROMP compositions of the invention may additionally comprise at least one antioxidant and/or antiozonant. Antioxidants and antiozonants include any antioxidant or antiozonant used in the rubber or plastics industry, including without limitation: 2,6-di-tert-butyl-4-methylphenol (BHT); styrenated phenol, such as Wingstay® S (Goodyear); 2- and 3-tert-butyl-4-methoxyphenol; alkylated hindered phenols, such as Wingstay C (Goodyear); 4-hydroxymethyl-2,6-di-tert-butylphenol; 2,6-di-tert-butyl-4-sec-butylphenol; 2,2'-methylenebis(4-methyl-6-tert-butylphenol); 2,2'-methylenebis(4-ethyl-6-tert-butylphenol); 4,4'-methylenebis(2,6-di-tert-butylphenol); miscellaneous bisphenols, such as Cyanox® 53 (Cytec Industries Inc.) and Permanax WSO; 2,2'-ethylidenebis(4,6-di-tert-butylphenol); 2,2'-methylenebis(4-methyl-6-(1-methylcyclohexyl)phenol); 4,4'-butylidenebis(6-tert-butyl-3-methylphenol); polybutylated Bisphenol A; 4,4'-thiobis(6-tert-butyl-3-methylphenol); 4,4'-methylenebis(2,6-dimethylphenol); 1,1'-thiobis(2-naphthol); methylenebridgedpolyaklylphenol, such as Ethyl antioxidant 738; 2,2'-thiobis(4-methyl-6-tert-butylphenol); 2,2'-isobutylidenebis(4,6-dimethylphenol); 2,2'-methylenebis(4-methyl-6-cyclohexylphenol); butylated reaction product of p-cresol and dicyclopentadiene, such as Wingstay L; tetrakis (methylene-3,5-di-tert-butyl-4-hydroxyhydrocinnamate) methane, i.e., Irganox® 1010 (BASF); 1,3,5-trimethyl-2,4, 6-tris(3,5-di-tert-butyl-4-hydroxybenzyl)benzene, e.g., Ethanox® 330 (Albemarle Corporation); 4,4'-methylenebis (2,6-di-tertiary-butylphenol), e.g., Ethanox 4702 or Ethanox 4710; 1,3,5-tris(3,5-di-tert-butyl-4-hydroxybenzyl)isocyanurate, i.e., Good-Rite® 3114 (Emerald Performance Materials), 2,5-di-tert-amylhydroquinone, tert-butylhydroquinone, tris(nonylphenylphosphite), bis(2,4-di-tert-butyl) pentaerythritol)diphosphite, distearyl pentaerythritol diphosphite, phosphited phenols and bisphenols, such as Naugard® 492 (Chemtura Corporation), phosphite/phenolic antioxidant blends, such as Irganox B215; di-n-octadecyl(3,5-di-tert-butyl-4-hydroxybenzyl)phosphonate, such as Irganox 1093; 1,6-hexamethylene bis(3-(3,5-di-tert-butyl-4-hydroxyphenylpropionate), such as Irganox 259, and octadecyl-3,5-di-tert-butyl-4-hydroxyhydrocinnamate, i.e., Irganox 1076, tetrakis(2,4-di-tert-butylphenyl)4,4'-biphenylylenediphosp honite, diphenylamine, and 4,4'-diemthoxydiphenylamine.

In another embodiment, resin compositions of the invention may further comprise at least one filler. Suitable fillers include, for example, metallic density modulators, microparticulate density modulators, organic fillers, inorganic fillers, such as, for example, microspheres, and macroparticulate density modulators, such as, for example, glass or ceramic beads.

In another embodiment, resin compositions of the invention may further comprise at least one reinforcing material. Suitable reinforcing materials include those that add to the strength or stiffness of a polymer composite when incorporated with the polymer. Reinforcing materials can be in the form of filaments, fibers, rovings, mats, weaves, fabrics, knitted material, cloth, glass fibers and fabrics, carbon fibers and fabrics, aramid fibers and fabrics, polyolefin fibers or fabrics (including ultrahigh molecular weight polyethylene fabrics such as those produced by Honeywell under the Spectra® trade name), and polyoxazole fibers or fabrics (such as those produced by the Toyobo Corporation under the Zylon® trade name).

ROMP compositions according to the invention may further comprise a sizing composition, or be used to provide improved adhesion to substrate materials that are sized with certain commercial silanes commonly used in the industry.

Film formers that are compatible with ROMP catalysts include epoxies, polyesters, polyurethanes, polyolefins, and/or polyvinyl acetates. Aqueous emulsions of modified epoxies, polyesters, and polyurethanes may also be used in the film former. The film former may also comprise polyolefins or polyolefin-acrylic copolymers, polyvinylacetates, modified polyvinylacetates, or polyolefin-acetate copolymers.

Nonionic lubricants may also be added to the sizing composition. Suitable nonionic lubricants that are compatible with ROMP compositions include esters of polyethylene glycols and block copolymers of ethylene oxide and propylene oxide. Suitable lubricants may contain polyethylene glycol (PEG) units with an average molecular weight between 200 and 2000, preferably between 200 and 600.

Silane coupling agent may optionally be added to the sizing composition, non-limiting examples including, methacrylate, acrylate, amino, or epoxy functionalized silanes along with alkyl, alkenyl, and norbornenyl silanes.

In another embodiment, the ROMP composition of the invention may additionally comprise at least one adhesion promoter. One class of adhesion promoters for use in the present invention are disclosed in International Pat. App. No. PCT/US2012/042850. Non-limiting examples of adhesion promoters that may be used in the present invention disclosed herein are generally compounds containing at least two isocyanate groups (such as, for example, methylene diphenyl diisocyanate and hexamethylene diisocyanate). The adhesion promoter may be a diisocyanate, triisocyanate, or polyisocyanate (i.e., containing four or more isocyanate groups). The adhesion promoter may be a mixture of at least one diisocyanate, triisocyanate, or polyisocyanate. In a more particular aspect of the invention, the adhesion promoter comprises, or is limited to, a diisocyanate compound, or mixtures of diisocyanate compounds.

Additional adhesion promoters suitable for use in the present invention comprise functionalized silanes of the formula $Fn-(A)_n-Si(Y^*)_3$, wherein $Y^*$ is selected from halide (preferably chloride) or OR; Fn is a functional group selected from acrylate, methacrylate, allyl, vinyl, alkene, cycloalkene, or norbornene; A is a divalent linking group selected from hydrocarbylene, substituted hydrocarbylene, heteroatom-containing hydrocarbylene, or substituted heteroatom-containing hydrocarbylene; n is 0 or 1; and R is selected from hydrocarbyl, substituted hydrocarbyl, heteroatom-containing hydrocarbyl, or substituted heteroatom-containing hydrocarbyl, preferably lower alkyl, more preferably methyl, ethyl, or isopropyl; and a peroxide selected from dialkyl and diaryl peroxides.

Articles may include, but are not limited to, those formed by standard manufacturing techniques including casting, centrifugal casting, pultrusion, molding, rotational molding, open molding, reaction injection molding (RIM), resin transfer molding (RTM), pouring, vacuum impregnation, surface coating, filament winding and other methods known to be useful for production of polymer articles and/or polymer composite articles. Furthermore, the compositions and articles of manufacture of the invention are not limited to a single polymer-surface interface but include also multilayers and laminates containing multiple polymer-surface interfaces. The invention is also suitable for manufacture of articles by the infusion of the resin into a porous material. Such porous materials include, but are not limited, to wood, cement, concrete, open-cell and reticulated foams and sponges, papers, cardboards, felts, ropes or braids of natural or synthetic fibers, and various sintered materials. Additionally, other manufacturing techniques include without limitation cell casting, dip casting, continuous casting, embedding, potting, encapsulation, film casting or solvent casting, gated casting, mold casting, slush casting, extrusion, mechanical foaming, chemical foaming, physical foaming, compression molding or matched die molding, spaying, spray up, Vacuum Assisted Resin Transfer Molding (VAR™), Seeman's Composite Resin Infusion Molding Process (SCRIMP), blow molding, in mold coating, in-mold painting or injection, vacuum forming, Reinforced Reaction Injection Molding (RRIM), Structural Reaction Injection Molding (SRIM), thermal expansion transfer molding (TERM), resin injection recirculation molding (RICM), controlled atmospheric pressure resin infusion (CAPRI), hand-layup. For manufacturing techniques requiring the use of a RIM or impingement style mixhead, including without limitation RIM, SRIM, and RRIM, articles of manufacture may be molded using a single mixhead or a plurality of mixheads as well as a plurality of material injection streams (e.g., two resin streams and one catalyst stream). As the invention allows for increasingly faster cycle times and increasingly higher mold temperatures using any of the aforementioned manufacturing techniques, particularly mold temperatures above 90° C., it may become necessary to mold ROMP compositions of the invention under high pressures or under vacuum to prevent defects caused by mixing issues and/or entrapped gases.

Furthermore, the present invention also allows for the making of articles of manufacture of any configuration, weight, size, thickness, or geometric shape. Examples of articles of manufacture include without limitation any molded or shaped article for use as an aerospace component, a marine component, an automotive component, a sporting goods component, an electrical component, and industrial component, medical component, dental component, or military component. In one embodiment an article may be a turbine component used on aircraft or general power generation. In one embodiment, turbine components may include without limitation one or more of an inlet, pylon, pylon fairing, an acoustic panel, a thrust reverser panel, a fan blade, a fan containment case, a bypass duct, an aerodynamic cowl, or an airfoil component. In one embodiment, an article may be a turbine blade component or may be a turbine blade. In one embodiment, an article may be a wind rotor blade, tower, spar cap, or nacelle for wind turbines. In one embodiment, an article may be an airframe component. Examples of aerospace components may include without limitation one or more of fuselage skin, wing, fairing, doors, access panel, aerodynamic control surface, or stiffener. In one embodiment an article may be an automotive component. Examples of automotive components may include without limitation one or more of body panel, fender, spoiler, truck bed, protective plate, hood, longitudinal rail, pillar, or door. Examples of industrial components may include without limitation one or more of risers platforms, impact protection structures for oil and gas; bridges, pipes, pressure vessels, power poles, coils, containers, tanks, liners, containment vessels, articles for application in corrosive environments (e.g., chlor-alkali, caustic, acidic, brine, etc.), centralizers (e.g., oilfield centralizer), electrolytic cell covers, reinforcement structures for concrete architectures and roads, or radiators. Examples of electrical components may include without limitation one or more wound articles, such as coils or electric motors, or insulating devices. In one embodiment, an article may be an eddy-current shielding component of a magnetic resonance imaging system or shielding component for any electromagnetic radiation. In one embodiment, an article may be a military component including without limitation ballistics resistant armor for personnel or vehicles, or ballistics resistant structures for protecting personnel or equipment. In one embodiment, an article may be a sporting goods component including without limitation an arrow shaft, a tennis racket frame, a hockey stick, compound bow limbs, or a golf club shaft. In one embodiment, an article may be an object used in offshore applications, where the object is at least partially coated with a ROMP composition of the invention, where the object includes but is not limited to pipes, pipelines, pipe fittings, hoses, hose fittings, tanks, containers, drums, manifolds, risers, field joints, configurations designated as Christmas trees (oil field Christmas tree, subsea Christmas tree), jumpers, spool pieces, configurations designated as pipeline end termination (PLET), configurations designated as pipeline end manifolds (PLEM), robotic parts, devices and vehicles used in sub-sea applications, configurations designated as subsea dog houses, and other sub-sea architectures and equipment. Other non-limiting examples of offshore applications include insulation materials (e.g., thermal insulation) and field joint coating material.

It will be appreciated that the temperature at which a metathesis reaction according to methods disclosed herein is conducted can be adjusted as needed over a wide range of temperatures. With highly active metathesis catalysts, olefin metathesis may occur at temperatures as low as −78° C. With increasingly latent catalysts, olefin metathesis may not be observed until temperatures of −40° C., −10° C., 0° C., 10° C., 20° C., 25° C., 35° C., 50° C., 70° C., 100° C., or 150° C. In one embodiment, the reactions are carried out at a temperature of at least about 35° C., and in another embodiment, the reactions are carried out at a temperature of at least about 50° C. In certain embodiments, a mold or preform may be filled with resin and catalyst at a temperature near room temperature (e.g., about 10-45° C., preferably 15-40° C., or more preferably 20-35° C.) and then heated over a period time to a higher temperature (e.g., about 50-200° C., or preferably 70-150° C., or more preferably 90-120° C.) to allow polymerization to complete more quickly. In certain embodiments, a mold or preform may be preheated to a temperature considerably above room temperature (e.g., about 50-250° C., or about 50-200° C., or about 50-150° C., or about 40-80° C., or about 40-60° C., or about 60-80° C., or about 50-100° C., or about 100-150° C., or about 150-200° C.) and then filled quickly with resin and catalyst to allow for fast cycle times.

EXPERIMENTAL

General Information—Materials and Methods

In the following examples, efforts have been made to ensure accuracy with respect to numbers used (e.g., amounts, temperature, etc.) but some experimental error and deviation should be accounted for. The examples are to be considered as not being limiting of the invention described herein.

All reactions involving metal complexes were conducted in oven-dried glassware under an argon or nitrogen atmosphere using standard Schlenk techniques. Chemicals and solvents were obtained from Sigma-Aldrich, Strem, Afla Aesar, Nexeo, Brenntag, AG Layne and TCI. Commercially available reagents were used as received unless otherwise noted. Silica gel was purchased from Fisher (0.040-0.063 µm, EMD Millipore).

Catalysts C627, C748-trans, C848, C727-trans, C871, C827 and C705 and sIMES were prepared using known methods disclosed in the literature.

Ultrene® 99 dicyclopentadiene (DCPD) was obtained from Cymetech Corporation. A modified DCPD base resin containing 20-25% tricyclopentadiene (and small amounts of higher cyclopentadiene homologs) (DCPD-HT) was prepared by heat treatment of Ultrene® 99 DCPD generally as described in U.S. Pat. No. 4,899,005.

$^1$H and $^{13}$C NMR spectra were recorded on a Varian 400 MHz spectrometer. Chemical shifts are reported in ppm downfield from Me$_4$Si by using the residual solvent peak as an internal standard (CDCl$_3$-(δ 7.24 ppm) and CD$_2$Cl$_2$-(δ 5.32 ppm). Spectra were analyzed and processed using Vnmr J 4.0 software.

HPLC analyses were carried out on an Agilent 1260 with the following conditions: Column—C8 (150×3 mm, 3.5 um); Mobile phase—A (CH$_3$CN/H$_2$O, 20/80), B (CH$_3$CN), 10/90 to 0/100 in 5 min.

The following abbreviations are used in the examples:
DCPD dicyclopentadiene
DCPD-HT dicyclopentadiene with 25-20% high trimer (tricyclopentadiene)
TCPD tricyclopentadiene
DCM/CH$_2$Cl$_2$ dichloromethane
N$_2$ nitrogen
CDCl$_3$ deuterated chloroform
SiO$_2$ silicagel
mL milliliter
° C. degrees Celsius
EtOAc ethyl acetate CD$_2$Cl$_2$ deuterated dichloromethane

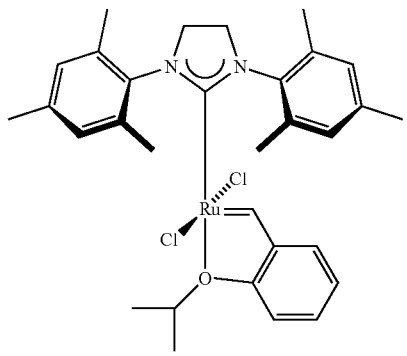

C627 [1,3-bis-(2,4,6-trimethylphenyl)-2-imidazolidinylidene]dichloro(o-isopropoxyphenylmethylene)Ruthenium(II) CAS [301224-40-8]

h hour

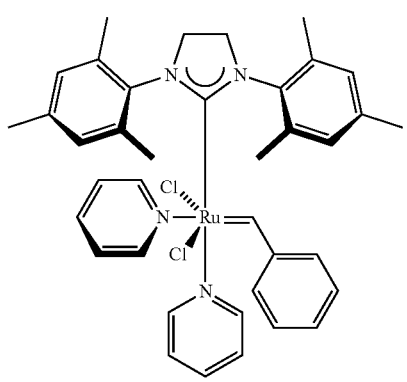

C727 [1,3-bis(2,4,6-trimethylphenyl)-2-imidazolidinylidene]dichloro (phenylmethylene)bis(pyridine)Ruthenium(II) CAS [357186-58-4] C$_6$D$_6$ deuterated benzene

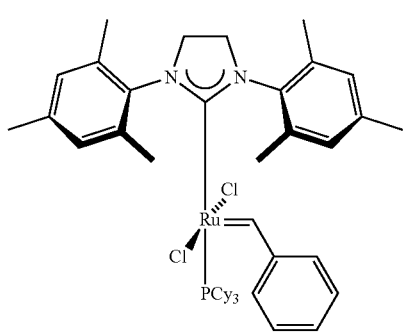

C848 [1,3-bis-(2,4,6-trimethylphenyl)-2-imidazolidinylidene] dichloro (phenylmethylene)(tricyclohexylphosphine) Ruthenium (II) CAS [246047-72-3]

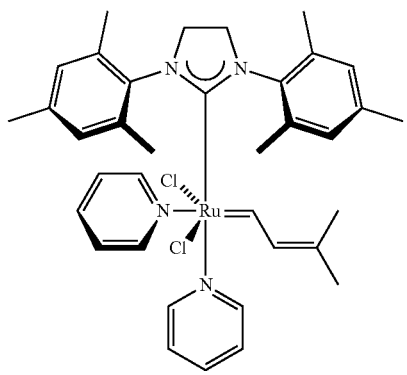

C705 [1,3-bis(2,4,6-trimethylphenyl)-2-imidazolidinylidene]dichloro(3-methyl-2-butenylidene)bis(pyridine) Ruthenium (II) CAS [507274-22-8]

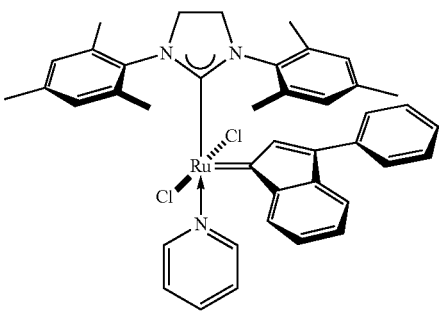

C748 [1,3-Bis(2,4,6-trimethylphenyl)-2-imidazolidinylidene]dichloro-(3-phenyl-1H-inden-1-ylidene)(pyridyl) Ruthenium (II) CAS [1031262-76-6]

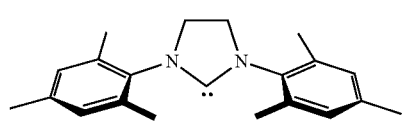

sIMes 1,3-Bis(2,4,6-trimethylphenyl)imidazolidin-2-ylidene CAS [173035-11-5]

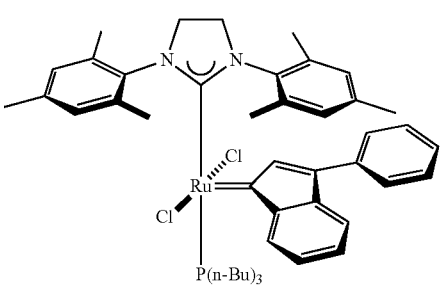

C871 [1,3-Bis(2,4,6-trimethylpheiiyl)-2-imidazolidinylidene]dichloro(3-phenylindenylidene)(tributylphosphine) Ruthenium (II) CAS [1416082-95-5]

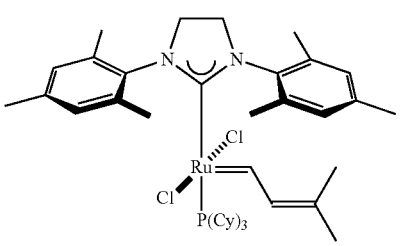

C827 [1,3-Bis-(2,4,6-trimethylphenyl)-2-imidazolidi-nylidene]dichloro (phenylmethylene)(tricyclohexylphosphine) Ruthenium (II) CAS [246047-72-3]

EXAMPLES

Example 1

RuCl$_2$(sIMes)$_2$(CHPh) (C875Bis)

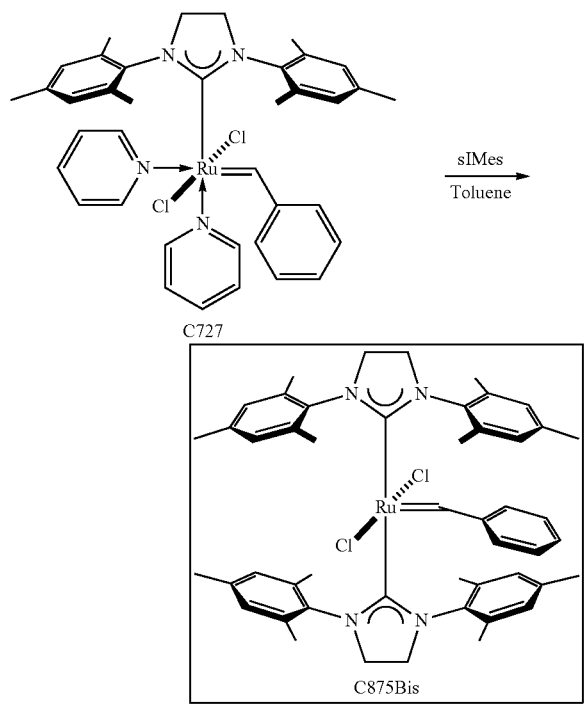

10.6 g of catalyst RuCl$_2$(sIMes)(CHPh)(Py)$_2$ (C727) (14.6 mmol) were placed in a round-bottomed flask, to which 6.7 g of sIMes (21.9 mmol) and 50 mL of anhydrous toluene were added under nitrogen. The round-bottomed flask was placed in a warm water bath at 45° C. and after 1 h, the bath was allowed to cool at room temperature. The reaction mixture was stirred for 3 additional hours and the reaction progression was followed by NMR. Since the reaction was incomplete, additional sIMes (2.0 g, 6.5 mmol) was added. The solution was stirred at room temperature for another hour. The solvent was removed under high vacuum and MeOH (degassed, 150 mL) was added to the mixture. After stirring for 10 minutes, the reaction mixture was filtered and the solid was washed with MeOH until the filtrate became colorless. The crude compound was dissolved in CH$_2$Cl$_2$, filtered on a silica gel plug, and recrystallized from CH$_2$Cl$_2$/MeOH. C875bis was obtained in 80% yield as a light brown solid. Purity: 99+% by HPLC. The NMR matched the published data.

Example 2

RuCl$_2$(sIMes)$_2$(CHCH=C(CH$_3$)$_2$) (C853Bis)

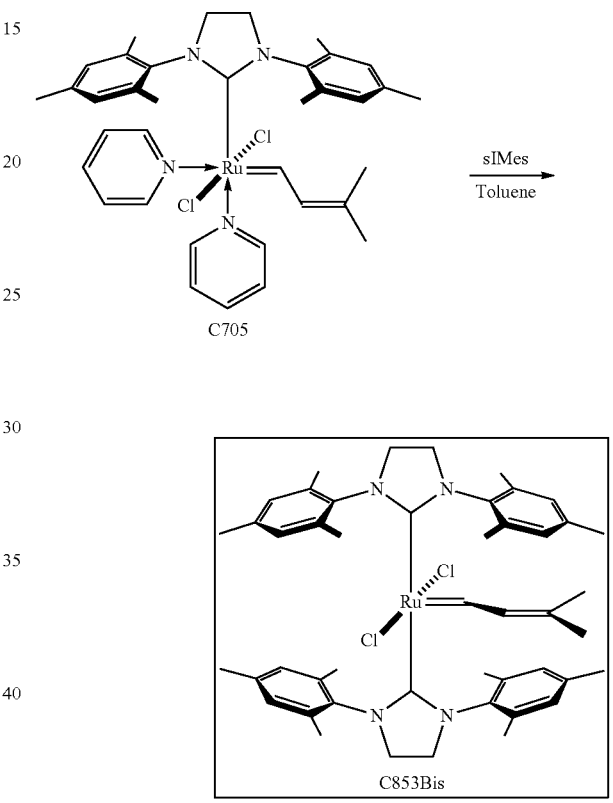

6.2 g of catalyst RuCl$_2$(sIMes)(CHCH=C(CH$_3$)$_2$)(Py)$_2$ (C705) (8.8 mmol) were placed in a round bottomed flask together with 4.0 g of sIMes (13.2 mmol) and 100 mL of anhydrous toluene, under nitrogen. After stirring the reaction mixture for 2 hours, the solvent was removed under vacuum. The residue was dissolved in degassed CH$_2$Cl$_2$ (25 mL), filtered on a silica gel plug. The filtrate was concentrated and dissolved in 100 mL of degassed MeOH, the mixture was further concentrated under vacuum until a significant amount of crystalline material crashed out of the solution. The crystals were filtered and washed with MeOH, dried under high vacuum and recrystallized from CH$_2$Cl$_2$/MeOH. C853Bis was obtained in 65% yield as an olive crystalline solid. Purity: 98+% by HPLC.

$^1$H NMR (CD$_2$Cl$_2$): δ 18.50 (d, J=10 Hz, Ru=CH, 1H), 6.94 (d, J=11 Hz), 6.71 (b, 8H), 3.49 (b, 8H), 2.7-1.9 (b, 36H), 0.78 (s, 3H), 0.48 (s, 3H).

$^{13}$C NMR (CD$_2$Cl$_2$): δ 289.39 (m, Ru=CH), 221.22, 145.87, 145.84, 138.16, 136.94, 139.0-136.5 (b), 130.43, 131.0-129.0 (b), 129.26, 52.92, (b), 27.72, 21.47, 20.26, 19.06.

Example 3

RuCl$_2$(sIMes)$_2$(Ph-Indenylidene) (C975Bis)

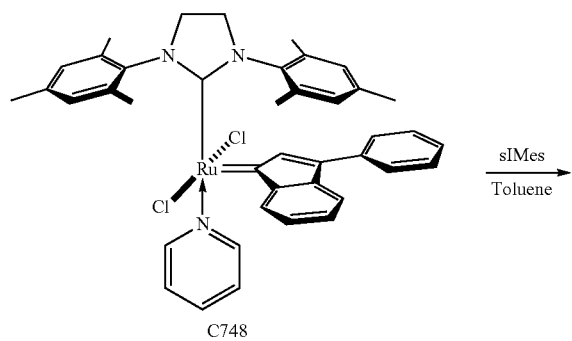

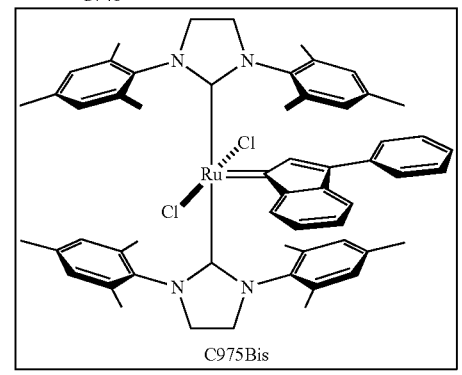

10.1 g of catalyst [RuCl$_2$(sIMes)(Phenyl-Indenylidene)(Py)]·(Py)$_{2.0}$ (C748·(Py)$_{2.0}$) (16.7 mmol) were placed in a round bottomed flask under N$_2$, together with 5.1 g of sIMes (16.7 mmol) and 40 mL of anhydrous toluene, under nitrogen. The reaction mixture was stirred for 3 hours, in a water bath at 30-50° C. and for 16 additional hours at RT. The solvent was removed under vacuum. The residue was dissolved in degassed MeOH (80 mL), filtered and the solid was washed with MeOH. The solid was dried under high vacuum, then dissolved in CH$_2$Cl$_2$/EtOAc and filtered on a silica gel plug. The filtrate was diluted with MeOH and the crystalline solid obtained was dried under vacuum. C975bis was obtained as a dark purple crystalline material in 80% yield. The NMR matched the published data.

Example 4

RuCl$_2$(sIMes)$_2$(CH-o-($^i$PrO)C$_6$H$_4$) (C933Bis)

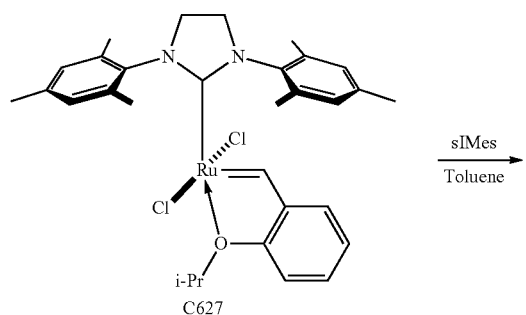

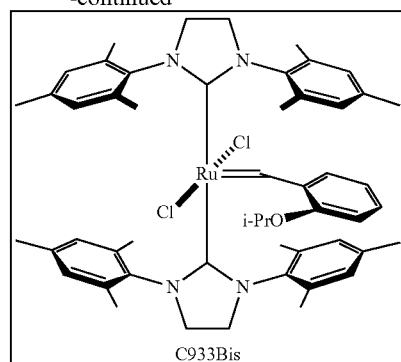

2.0 g of catalyst RuCl$_2$(sIMes)(CH-o-($^i$PrO)C$_6$H$_4$) (C627) (3.2 mmol) and 1.46 g of sIMes (4.8 mmol) were placed in a round bottomed flask under nitrogen, in 10 ml of anhydrous toluene. The reaction mixture was heated in a water bath at 45° C. and stirred for 3 h and another 16 h at room temperature. The formed suspension was filtered and washed with MeOH. C933Bis was obtained as a light pink solid in 40% yield. Purity: 99+% by HPLC.

$^1$H NMR (CD$_2$Cl$_2$): δ 20.04 (s, 1H), 8.46 (d, J=10 Hz, 1H), 7.17 (t, J=8 Hz, 1H), 7.1-6.3 (b, 6H), 6.40 (t, J=7 Hz, 1H), 6.21 (d, J=8 Hz, 1H), 6.1-5.7 (b, 2H), 4.07 (septet, J=6 Hz, 1H), 3.7-3.3 (b, 8H), 2.7-1.7 (b, 36H), 1.48 (d, J=6 Hz, 6H).

$^{13}$C NMR (CD$_2$Cl$_2$): δ 289.16 (m, Ru=CH), 220.80, 148.12, 142.58, 139.0-135.0 (b, m), 134.43, 130.15 (b), 129.33, 119.53, 119.78, 70.08, 55.0-52.0 (b), 23.40, 21.46, 19.47, 20.0-18.0 (b).

Example 5

RuCl$_2$(sTMes)$_2$(CHCH$_2$OAc) (C871Bis)

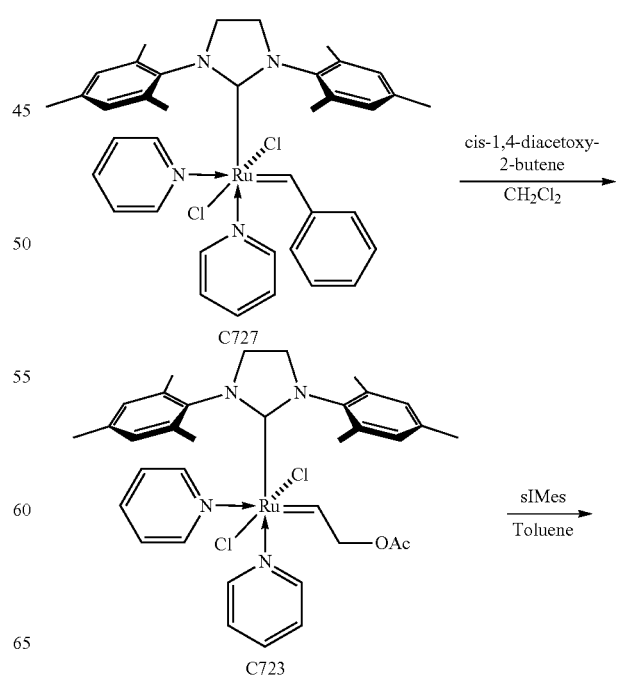

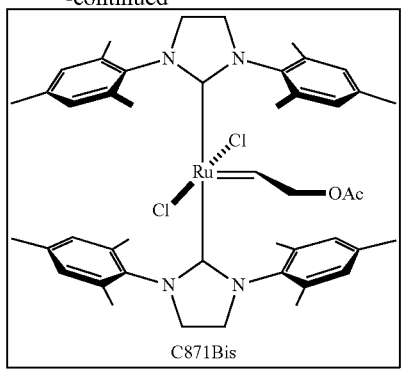

C871Bis 7.27 g of catalyst RuCl$_2$(sIMes)(CHPh)(Py)$_2$ (C727) (10 mmol) were placed in a round bottomed flask, with 100 mL of degassed CH$_2$Cl$_2$ and 8.6 g cis-1,4-diacetoxy-2-butene (50 mmol). The reaction mixture was stirred at room temperature for 1 h. The solvent was evaporated under vacuum. The crude product was dissolved in degassed heptanes, filtered and washed with heptanes. RuCl$_2$(sIMes)(CHCH$_2$OAc)(Py)$_2$ (C723) was obtained as a grey solid.

$^1$H NMR (CD$_2$Cl$_2$): δ 18.70 (t, J=4 Hz, 1H), 9.0-7.8 (b, 4H), 7.48 (b, 2H), 7.02 (b, 4H), 6.95 (s, 2H), 6.82 (s, 2H), 4.15-3.90 (m, 4H), 3.89 (d, J=4 Hz, 2H), 2.53 (s, 6H), 2.39 (s, 6H), 2.30 (s, 3H), 2.21 (s, 3H), 1.91 (s, 3H).

$^{13}$C NMR (CD$_2$Cl$_2$): δ 323.91 (Ru=CH, m), 218.40, 170.69, 150.93, 138.86, 138.68, 138.55, 137.97, 137.31, 136.68, 136.07 (b), 54.39, 52.00, 51.69, 21.48, 21.17, 21.08, 19.72, 18.96.

4.3 g of catalyst RuCl$_2$(sIMes)(CHCH$_2$OAc)(Py)$_2$ (C723) (5.9 mmol) and 3.64 g of sIMes (11.9 mmol) were mixed in a round bottomed flask in 50 mL of anhydrous toluene. The reaction mixture was stirred for 2 h after which the solvent was removed under vacuum and the residue was washed with MeOH. The obtained solid, was recrystallized from CH$_2$Cl$_2$/MeOH. C871Bis was obtained as a yellow solid with a 19% yield. HPLC Purity: 98+%.

$^1$H NMR (CDCl$_3$): δ 18.30 (t, J=3 Hz, Ru=CH, 1H), 6.85-6.65 (b, 8H), 3.6-3.4 (b, 8H), 2.90 (d, J=3 Hz, 2H), 2.6-2.0 (b, 36H), 1.79 (s, 3H).

$^{13}$C NMR (CD$_2$Cl$_2$): δ 305.42 (m, Ru=CH), 218.84, 169.99, 137.73, 130.48, 86.40, 52.51 (b), 21.64, 19.06.

Example 6

RuCl(η$_2$-sIMes)(CH-o-(i-PrO)C$_6$H$_4$)(C590)

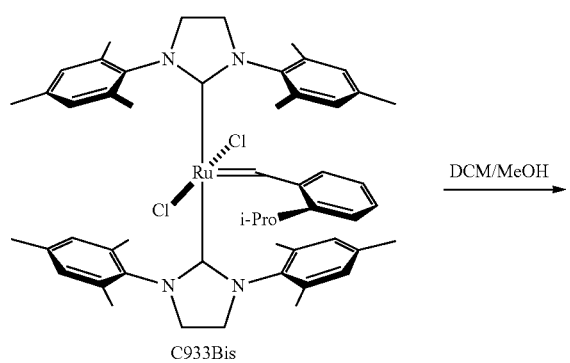

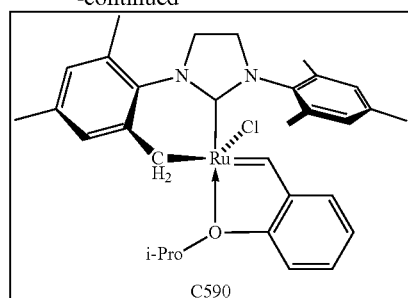

C590

6.2 g of RuCl$_2$(sIMes)$_2$(CH-o-(i-PrO)C$_6$H$_4$) (C933Bis) (6.6 mmol) were dissolved in 40 mL of DCM under nitrogen, in a 250 mL round bottomed flask. 10 mL of MeOH were added. The solution was stirred at room temperature for 3 days. A crystalline purple solid precipitated out of the solution. The mixture was filtered and the solid was washed with MeOH. The filtrate was reduced under vacuum and more solid was recovered. The solid batched were combined and dried under high vacuum for 4 hours. The structure was confirmed by X-ray crystal structure as shown in FIG. 1. 2.85 g of C590 were obtained in 73% yield.

$^1$H NMR (CDCl$_3$): δ 14.37 (s, 1H), 7.26 (m, 1H), 7.11 (s, 1H), 7.08 (s, 1H), 7.07 (s, 1H), 6.95 (s, 1H), 6.90 (d, J=8 Hz, 1H), 6.81 (s, 1H), 6.80 (s, 1H), 5.07 (m, 1H), 4.35 (m, 1H), 4.2-4.0 (m, 2H), 3.70 (m, 1H), 3.10 (d, J=7 Hz, 1H), 2.43 (s, 3H), 2.42 (s, 3H), 2.37 (s, 3H), 2.35 (s, 3H), 2.30 (s, 3H), 2.18 (d, J=7 Hz, 1H), 1.46 (m, 6H).

Catalyst Aging Experiments

Catalyst aging experiments were performed to analyze the degradation of the catalysts, in non-inert conditions at multiple temperatures and different time points. The following catalysts were studied in this experiment: C627, C933Bis, C853Bis, C827, C848, C871 and C875Bis. Five samples of each catalyst were prepared by suspending 21 mg of each catalyst in 2 g of CP70 mineral oil. Each sample was placed in a vial: the first vial was used as control, two vials were capped and the last two vials were kept open. One capped vial and one open vial of the same catalyst, were placed in an incubator heated at 25° C. and the other two vials of the same catalyst, were placed into an incubator kept at 45° C. None of the incubated vials were sparged. The samples were allowed to age in incubators, 2, 8 and 16 days. Only the control was sparged and kept in the fridge at 4° C., protected from light.

The five samples of each catalyst were removed after 2 days, 8 days and 16 days, and each time 2% weight aliquots were taken and studied in ROMP reactions.

The catalytic activity of the complexes was evaluated in ring opening metathesis polymerization (ROMP) reactions as follows. A 200 mL beaker was filled with 100 g of DCPD-24% TCPD monomer. The monomer was equilibrated to the desired temperature in an oil bath (30° C.+/−0.5 C). A J-Type thermocouple was suspended directly into the center of the monomer. 2% by weight of the catalyst under study, was then added to the monomer to form a ROMP composition. Addition of the catalyst to the monomer to form the ROMP composition denoted the start of the ROMP reaction and hence, this was time point zero. Temperature readings were recorded using the thermocouple, the exotherm peak temperature was noted in each case. A sample from each beaker was cut and used to measure the Tg by DSC.

A color change of the incubated catalyst suspension was also observed overtime. The color change was associated with degradation of the catalyst.

TABLE 1

Catalyst C933bis

|  | control | 25° C. open | 25° C. closed | 45° C. open | 45° C. closed |
|---|---|---|---|---|---|
| 2 days Peak Exotherm Temperature (° C.) | 193.6 | 190.1 | 194.8 | 193.9 | 193.3 |
| 8 days Peak Exotherm Temperature (° C.) | 194.1 | 194.1 | 194.1 | 194.1 | 194.1 |
| 16 days Peak Exotherm Temperature (° C.) | 194.4 | 194.4 | 192.1 | 190.7 | 191.4 |
| 2 days Tg (° C.) |  |  |  |  |  |
| 8 days Tg (° C.) |  | 164.6 | 164.8 | 162.8 | 165.03 |
| 16 days Tg (° C.) |  | 164.8 | 163.2 |  | 164.5 |

TABLE 2

Catalyst C853bis

|  | control | 25° C. open | 25° C. closed | 45° C. open | 45° C. closed |
|---|---|---|---|---|---|
| 2 days Peak Exotherm Temperature (° C.) |  | 191.1 | 195.9 | 193.2 | 192.2 |
| 8 days Peak Exotherm Temperature (° C.) |  | 193.4 | 194.9 | 192.6 | 193.6 |
| 16 days Peak Exotherm Temperature (° C.) |  | 194.7 | 194.7 | 195.2 | 192.8 |
| 2 days Tg (° C.) |  |  |  |  |  |
| 8 days Tg (° C.) |  |  |  |  |  |
| 16 days Tg (° C.) |  | 164.92 | 164.9 | 163.95 | 167.5 |

TABLE 3

Catalyst C827

|  | control | 25° C. open | 25° C. closed | 45° C. open | 45° C. closed |
|---|---|---|---|---|---|
| 2 days Peak Exotherm Temperature (° C.) | 193.1 | 192.4 | 192.0 | 190.4 | 189.3 |
| 8 days Peak Exotherm Temperature (° C.) | 189.4 | 188.0 | 186.6 | 178.0 | 182.0 |
| 16 days Peak Exotherm Temperature (° C.) | 192.7 | 185.0 | 109.4 | 195.2 | 142.2 |
| 2 days Tg (° C.) |  | 165.14 | 161.6 | 164.5 | 162.2 |
| 8 days Tg (° C.) |  | 152.5 | 153.6 | 120.3 | 127.6 |
| 16 days Tg(° C.) |  | 146.7 | 145.6 | 93.7 | 92.3 |

TABLE 4

Catalyst C848

|  | control | 25° C. open | 25° C. closed | 45° C. open | 45° C. closed |
|---|---|---|---|---|---|
| 0 day Peak Exotherm Temperature (° C.) | 188.0 | 188.0 | 189.0 | 186.0 | 187.0 |
| 8 days Peak Exotherm Temperature (° C.) | 183.0 | 183.0 | 180.0 | 164.0 | 173.0 |
| 16 days Peak Exotherm Temperature (° C.) | 194.1 | 150.8 | 158.8 | 113.9 | 128.3 |
| 0 day Tg (° C.) | 149.0 | 153.45 | 150.4 | 143.8 | 149.4 |
| 8 days Tg (° C.) | 130.26 | 130.26 | 131.7 | 105.5 | 98.3 |
| 16 days Tg (° C.) | 169.7 | 73.12 | 72.8 | 62.2 | 65.14 |

TABLE 5

Catalyst C871

|  | control | 25° C. open | 25° C. closed | 45° C. open | 45° C. closed |
|---|---|---|---|---|---|
| 2 days Peak Exotherm Temperature (° C.) |  | 193.7 | 193.9 | 196.8 | 196.2 |
| 16 days Peak Exotherm Temperature (° C.) |  | 194.9 | 194.2 | 194.9 | 195.2 |
| 32 days Peak Exotherm Temperature (° C.) |  | 195.3 | 195.4 | 192.4 | 192.4 |
| 2 days Tg (° C.) |  | 167.2 | 168.6 | 167.8 | 166.5 |
| 16 days Tg (° C.) |  | 165.02 | 168.3 | 164.6 | 167.8 |
| 32 days Tg (° C.) |  | 146.7 |  |  |  |

TABLE 6

Catalyst C875 bis

|  | control | 25° C. open | 25° C. closed | 45° C. open | 45° C. closed |
|---|---|---|---|---|---|
| 2 days Peak Exotherm Temperature (° C.) |  | 193.7 | 197.5 | 194.2 | 194.0 |
| 8 days Peak Exotherm Temperature (° C.) |  | 194.3 | 197.7 | 194.9 | 194.8 |
| 16 days Peak Exotherm Temperature (° C.) |  | 196.3 | 196.1 | 195.6 | 192.8 |
| 2 days Tg (° C.) |  | 167.2 | 168.9 | 169.04 | 166.9 |
| 8 days Tg (° C.) |  |  |  |  |  |
| 16 days Tg(° C.) |  | 173.35 | 167.6 | 167.4 | 168.2 |

TABLE 7

| | Catalyst C627 | | | |
|---|---|---|---|---|
| | control | 25° C. open | 25° C. closed | 45° C. open | 45° C. closed |
| 2 days Peak Exotherm Temperature (° C.) | | 193.7 | 197.5 | 194.2 | 194.0 |
| 8 days Peak Exotherm Temperature (° C.) | | 194.3 | 197.7 | 194.9 | 194.8 |
| 16 days Peak Exotherm Temperature (° C.) | | 196.3 | 196.1 | 195.6 | 192.8 |
| 2 days Tg (° C.) | | 167.2 | 168.9 | 169.04 | 166.9 |
| 8 days Tg (° C.) | | | | | |
| 16 days Tg (° C.) | 173.35 | 167.6 | 167.4 | 168.2 |

Catalysts Study

All the experiments were run with 30% Trimer-DCPD and 2 PHR antioxidant (Ethanox 4702) catalyzed at room temperature~24-27° C. Each catalyst powder was dissolved in 1 gram of DCM and then further diluted in 1 gram Crystal Plus 70FG (mineral oil) mixed with CAB-O-SIL TS-610 (fumed silica) at 2 phr catalyst carrier.

Liquid Resin DSC

The catalyzed resin (14-18 mg) was placed in hermetically sealed pan and ramped to 250° C. at 10° C./min.

| Catalyst (1 wt. %) | DSC Cure Profile | Ramp | Onset ° C. |
|---|---|---|---|
| C933bis | 30° C.-200° C. | 10° C./mins | 95.9 |
| C853bis | 30° C.-200° C. | 10° C./mins | 104.16 |
| C875bis | 30° C.-200° C. | 10° C./mins | 117.19 |

High Temperature Casting (100° C.)

The catalyzed resin was poured into an aluminum mold measuring 6×4×¼" that was preheated to a temperature of 100° C. Each part was held for 120 minutes at 100° C. and then demolded.

| Catalyst (1 wt. %) | Cure Profile | Ramp | Tg ° C. | Comments |
|---|---|---|---|---|
| C933bis | 100° C./120 mins | Mold pre-heated to temp. | 115.8* | ¼" mold |
| C853bis | 100° C./120 mins | Mold pre-heated to temp. | 166.6 | ¼" mold |
| C875bis | 100° C./120 mins | Mold pre-heated to temp. | 156.5 | ¼" mold |

*Panel had significant outgassing

High Temperature Casting (90° C.)

The catalyzed resin was poured into an aluminum mold measuring 6×4×¼" that was preheated to a temperature of 90° C. Each part was held for 120 minutes at 90° C. and then demolded.

| Catalyst (1 wt. %) | Cure Profile | Ramp | Tg ° C. | Comments |
|---|---|---|---|---|
| C933bis | 90° C./120 mins | Mold pre-heated to temp. | 144.12 | ¼" mold |
| C853bis | 90° C./120 mins | Mold pre-heated to temp. | 80.42 | ¼" mold |
| C875bis | 90° C./120 mins | Mold pre-heated to temp. | 83.88 | ¼" mold |

High Temperature Casting (80° C.)

The catalyzed resin was poured into an aluminum mold measuring 6×4×¼" that was preheated to a temperature of 80° C. Each part was held for 120 minutes at 80° C. and then demolded.

| Catalyst (1 wt. %) | Cure Profile | Ramp | Tg ° C. | Comments |
|---|---|---|---|---|
| C933bis | 80° C./120 mins | Mold pre-heated to temp. | 148.44 | ¼" mold |
| C853bis | 80° C./120 mins | Mold pre-heated to temp. | 83.7 | ¼" mold |
| C875bis | 80° C./120 mins | Mold pre-heated to temp. | n/a** | ¼" mold |

**Panel did not exotherm or cure.

Viscosity Data at 50° C.

Catalyzed resin was held at 50° C. to determine viscosity increase over time (FIG. 2).

| Catalyst (1 wt. %) | Resin Temperature | Initial Viscosity (cP) | Viscosity at 90 mins (cP) | Viscosity at 120 mins (cP) |
|---|---|---|---|---|
| C933bis | 50° C. | 14 | 300 | gelled |
| C853bis | 50° C. | 14-24 | 200 | 356 |
| C875bis | 50° C. | 14-18 | 14-18 | 18-24 |

8. The olefin metathesis catalyst according to claim 7, which is:
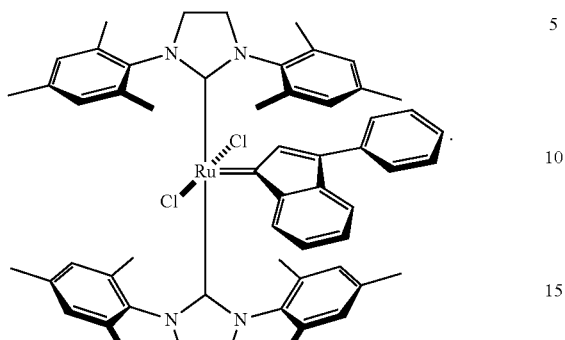

What is claimed is:

1. A olefin metathesis catalyst represented by the structure of Formula (I), $$X^3\underset{X^4}{\overset{L^4}{\underset{|}{\overset{|}{M}}}}=(C)_q=C\underset{A^2}{\overset{A^1}{\diagup}} \quad \text{Formula (I)}$$

wherein:
M is Ru;
q is 0;
$X^3$ is Cl;
$X^4$ is Cl;
$L^4$ and $L^5$ are independently $$\underset{A^3}{\overset{A^5}{\diagdown}}\underset{N}{\overset{A^6}{\diagdown}}\underset{\underset{\cdot\cdot}{N}}{\overset{A^7\diagdown A^8}{\diagup}}\underset{A^4}{,}$$

$A^3$, $A^4$, $A^{11}$ and $A^{12}$ are independently unsubstituted phenyl; phenyl substituted with at least one substituent selected from halo or $C_1$-$C_6$ alkyl; unsubstituted $C_5$-$C_{10}$ cycloalkyl; or $C_5$-$C_{10}$ substituted cycloalkyl with at least one substituent selected from halo and $C_1$-$C_6$ alkyl;

$A^5$, $A^6$, $A^7$, $A^8$, $A^9$ and $A^{10}$ are independently hydrogen, $C_1$-$C_6$ alkyl or $C_5$-$C_{10}$ aryl;

o is 1;

$A^1$ is hydrogen; and $A^2$ is phenyl, $C_1$-$C_3$ alkyl, or $C_2$-$C_4$ alkenyl, and $A^2$ is substituted with at least one substituent selected from: $C_1$-$C_6$ alkoxy (—O-alkyl), $C_2$-$C_{24}$ alkylcarbonyloxy (—O—CO-alkyl) or $C_1$-$C_6$ alkyl groups.

2. The olefin metathesis catalyst according to claim 1, wherein:

$A^5$, $A^6$, $A^7$, $A^8$ are each hydrogen;

$A^2$ is phenyl, vinyl, or $C_1$-$C_3$ alkyl and $A^2$ is substituted with at least one substituent selected from: $C_1$-$C_6$ alkoxy (—O-alkyl), $C_2$-$C_{24}$ alkylcarbonyloxy (—O—CO-alkyl) or $C_1$-$C_6$ alkyl groups; and $A^3$ and $A^4$ are each phenyl independently substituted with three moieties selected from $C_1$-$C_6$ alkyl.

3. The olefin metathesis catalyst according to claim 2, wherein:

$A^2$ is —$CH_2$-OC(O)$CH_3$, —CH=C($CH_3$)$_2$ or 2-phenyl iso-propoxy; and $A^3$ and $A^4$ are each mesityl.

4. The olefin metathesis catalyst according to claim 1, which is:

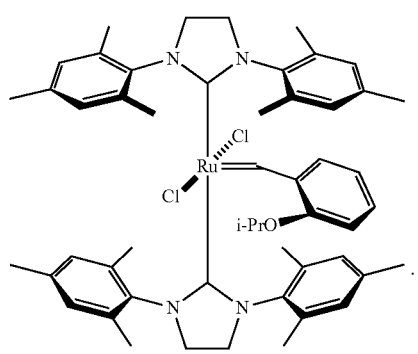

5. The olefin metathesis catalyst according to claim 1, which is:

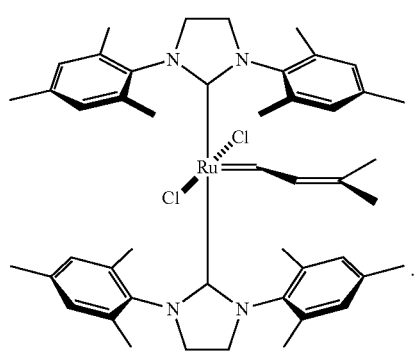

6. The olefin metathesis catalyst according to claim 1, which is:

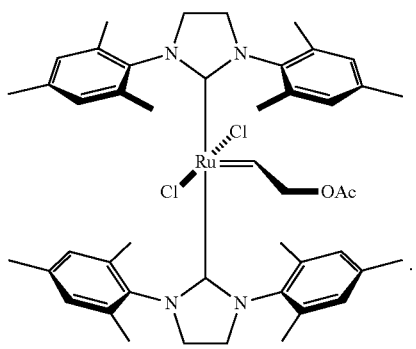

7. An olefin metathesis catalyst represented by the structure of Formula (I),

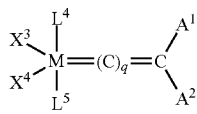

Formula (I)

wherein:

M is Ru;

q is 0;

$X^3$ is Cl;

$X^4$ is Cl;

$L^4$ and $L^5$ are independently

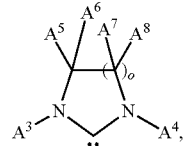

$A^3$, $A^4$, $A^{11}$ and $A^{12}$ are independently unsubstituted phenyl; phenyl substituted with at least one substituent selected from halo and $C_1$-$C_6$ alkyl; unsubstituted $C_5$-$C_{10}$ cycloalkyl; or $C_5$-$C_{10}$ substituted cycloalkyl with at least one substituent selected from halo or $C_1$-$C_6$ alkyl;

$A^5$, $A^6$, $A^7$, $A^8$, $A^9$ and $A^{10}$ are independently hydrogen, $C_1$-$C_6$ alkyl or $C_5$-$C_{10}$ aryl;

o is 1;

$A^1$ and $A^2$ together form a ring

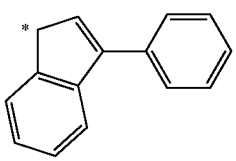 [SMILES: C1=C(c2ccccc2)c2ccccc2C1]

* position that the ring is bonded to the double bond.